US008859209B2

(12) United States Patent
Larsen

(10) Patent No.: US 8,859,209 B2
(45) Date of Patent: *Oct. 14, 2014

(54) REIMMUNIZATION AND ANTIBODY DESIGN

(75) Inventor: Janus Beierholm Larsen, Svendborg (DK)

(73) Assignee: Carviar APS, Copenhagen K (DK)

( * ) Notice: Subject to any disclaimer, the term of this patent is extended or adjusted under 35 U.S.C. 154(b) by 1200 days.

This patent is subject to a terminal disclaimer.

(21) Appl. No.: 12/299,670

(22) PCT Filed: Jan. 12, 2007

(86) PCT No.: PCT/DK2007/000018
§ 371 (c)(1),
(2), (4) Date: Apr. 13, 2009

(87) PCT Pub. No.: WO2007/079755
PCT Pub. Date: Jul. 19, 2007

(65) Prior Publication Data
US 2010/0143329 A1 Jun. 10, 2010

(30) Foreign Application Priority Data

Jan. 12, 2006 (DK) .................................. 2006 00054

(51) Int. Cl.
G01N 33/53 (2006.01)
A61K 39/395 (2006.01)
C07K 16/00 (2006.01)
C07K 16/02 (2006.01)
C40B 30/04 (2006.01)
A61K 39/00 (2006.01)
C40B 30/00 (2006.01)

(52) U.S. Cl.
CPC ........... C07K 16/00 (2013.01); A61K 2039/507 (2013.01); C07K 2317/23 (2013.01); A61K 2039/505 (2013.01); C40B 30/00 (2013.01); C07K 16/02 (2013.01); A61K 39/00 (2013.01); C40B 30/04 (2013.01); G01N 33/53 (2013.01)
USPC ....................... 435/7.1; 530/387.1; 424/130.1

(58) Field of Classification Search
None
See application file for complete search history.

(56) References Cited

U.S. PATENT DOCUMENTS

| 4,897,268 | A |  | 1/1990 | Tice et al. |  |
| 4,906,564 | A |  | 3/1990 | Lyon et al. |  |
| 5,075,109 | A |  | 12/1991 | Tice et al. |  |
| 5,510,240 | A |  | 4/1996 | Lam et al. |  |
| 6,024,958 | A | * | 2/2000 | Lehner et al. | 424/190.1 |
| 6,617,114 | B1 |  | 9/2003 | Fowlkes et al. |  |
| 2002/0028917 | A1 | * | 3/2002 | Gee et al. | 530/388.1 |
| 2002/0058031 | A1 | * | 5/2002 | Tung et al. | 424/140.1 |
| 2002/0168684 | A1 |  | 11/2002 | Comb et al. |  |
| 2003/0212258 | A1 | * | 11/2003 | Su et al. | 530/350 |
| 2004/0115215 | A1 | * | 6/2004 | Williams | 424/184.1 |
| 2005/0090434 | A1 | * | 4/2005 | Morris et al. | 514/12 |
| 2006/0115485 | A1 | * | 6/2006 | Losonsky et al. | 424/159.1 |
| 2006/0153865 | A1 | * | 7/2006 | Maksyutov et al. | 424/188.1 |
| 2006/0198849 | A1 |  | 9/2006 | Paau et al. |  |

FOREIGN PATENT DOCUMENTS

| WO | WO 96/22530 | 7/1996 |
| WO | WO 00/14536 | 3/2000 |
| WO | WO 03/089471 | 10/2003 |
| WO | WO 2004083246 | 9/2004 |
| WO | WO 2004/106384 | 12/2004 |
| WO | WO 2005/003174 | 1/2005 |
| WO | WO 2005/005481 | 1/2005 |
| WO | WO 2006/117007 | 11/2006 |
| WO | WO 2007/124755 | 11/2007 |

OTHER PUBLICATIONS

Castro et al. "Snake venom thrombin-like enzymes: from reptilase to now" CMLS, Cell. Mol. Life. Scie. 61 (2004), 843-856.*
Stills "Adjuvants and antibody production: dispelling the myths associated with Freund's complete and other adjuvants" ILAR Journal, 46(3), 2005, pp. 280-293.*
Warren Gallagher, "FTIR analysis of protein structure" pp. 1-8.*
Yang et al. Neutralizing epitope mapping of six beta1-bungarotoxin monoclonal antibodies and its application in beta1-bungarotoxin peptide vaccine design, Biochem J (1998), 330, 497-503.*
Hermes, Why did my chickesn stops laying? PNW 565, 2003, pp. 1-2.*
Koga et al. "Sucrose-dependent Cell Adherence and Cariogenicity of Serotype c Streptococcus mutans" Journal of General Microbiology (1986), 132, 2873-2883.*
Cook, Carrie L. et al., "Simple Purification Methods for an αGalactose-Specific Antibody from Chicken Eggs," 2001, Journal of Bioscience and Bioengineering, vol. 91, No. 3, p. 305-310.
Fang, Xiangming et al., "Polyclonal Gene-Specific IgY Antibodies for Proteomics and Abundant Plasma Protein Depletion," 2003, Frontiers of Pharmaceuticals and Biotechnology, vol. 4, p. 1-23.

(Continued)

Primary Examiner — Daniel E Kolker
Assistant Examiner — James Rogers
(74) Attorney, Agent, or Firm — McLane, Graf, Raulerson & Middleton, PA

(57) ABSTRACT

The present invention relates to methods for harvesting of antibodies from an antibody library. The antibodies are harvested by utilizing a certain epitope that is analogous to the epitope of the antigen used for immunization but that may differ in global physical and biochemical properties allowing the production of antibodies against antigens that normally can not be utilized as immunizing agents. The present invention furthermore relate to fields of use for harvested antigens in industry, agriculture and healthcare.

96 Claims, No Drawings

(56) References Cited

OTHER PUBLICATIONS

Gassmann, Max et al., "Efficient production of chicken egg yolk antibodies against a conserved mammalian protein," 1990, Fed. of American Soc. For Experimental Biology, vol. 4, p. 2528-2532.

Goldring et al., "Raising Antibodies in Chickens Against Primaquine Pyrimethamine, Dapsone, Tetracycline, and Doxycycline", 2005, Immunological Investigations, vol. 34, pp. 101-114.

Hanly, Carey W. et al., "Review of Polyclonal Antibody Production Procedures in Mammals and Poultry," 1995, ILAR Journal, vol. 37, No. 3, p. 93-118.

Nielsen, B. Rye et al., "Reagin Production in Mice: Effect of Subcutaneous and Oral Sensitization with Untreated Bovine Milk and Homogenized Bovine Milk," 1989, In Vivo, 3: p. 271-274.

Poulsen, O.M., et al., "Effect of homogenization and pasteurization on the allergenicity of bovine milk analysed by a murine anaphylactic shock model," 1987 Clinical Allergy, vol. 17, p. 449-458.

Narat, Mojca, "Production of Antibodies in Chickens," 2003, Food Technol. Biotechnol., 41 (3), p. 259-267.

Schade, Rüdiger, et al., "The Production of Avian (Egg Yolk) Antibodies: IgY," 1996, ATLA, 24, p. 925-934.

Hau, Jann (ed.), Handbook of Laboratory Animal Science vol. 1: Essential Principles and Practices, Second Edition, Chapter 16, "Production of Polyclonal and Monoclonal Antibodies," © 1997-2009, Culinary and Hospitality Industry Publications Services, p. 392-408.

Hendriksen et al. "Production of Polyclonal and Monoclonal Antibodies", Handbook of Laboratory Animal Science, Second Edition, Chapter 16, 2003 by CRC Press LLC.

Polson et al. "Antibodies to Proteins from Yolk of Immunized Hens", Immunological Communications, 9(5), 495-514 (1980); 1980 by Marcel Dekker Inc.

Jüngling et al. "Chicken Egg Antibodies for Prophylaxis and Therapy of Infectious Intestinal Diseases", J. Vet. Med. B 38, 373-381 (1991); 1991 Paul Parey Scientific Publishers, Berlin and Hamburg, ISSN 0931-1793.

Tini, et al. "Generation and Application of Chicken Egg-Yolk Antibodies", Comparative Biochemistry and Physiology Part A 131 (2002) 569-574, 2002 Elsevier Science Inc.

Zhang, Peng, et al. "Direct Interaction of Proliferating Cell Nuclear Antigen with the p125 Catalytic Subunit of Mammalian DNA Polymerase Delta", The Journal of Biological Chemistry, vol. 274, No. 38, Issue of Sep. 17, 1999, pp. 26647-26653.

\* cited by examiner

REIMMUNIZATION AND ANTIBODY DESIGN

FIELD OF THE INVENTION

The present invention relates to methods for the production and harvesting of specific antibodies from a pool of existing antibodies and manufacturing of new antibodies based on existing antibodies through epitope alteration and/or conversion of an existing antibody to another in order to improve existing vaccines.

BACKGROUND OF INVENTION

Polyclonal antibodies are conventionally obtained by the time consuming method of immunizing a suitable host, usually a mammalian animal, with a composition comprising the molecule of interest as an antigen and a suitable adjuvant. The antibody may be e.g. a chemical compound or a peptide where the latter may be chosen from a peptide library containing a great number of peptides having a systematic combination of amino acids.

Several weeks subsequent to immunization, antibodies generated by several B cell clones, hence the term polyclonal, specific to the antigen can be harvested by bleeding the animal and collecting the serum. Polyclonal antibodies may bind different parts of the antigen although individual polyclonal antibodies may bind virtually the same parts of an antigen with different affinities.

Polyclonal antibodies are typically obtained from mammalian host animals such as rats, mice, goats, horses, sheep, rabbits, pigs and others. A large amount of experimental animals are used to generate different antibodies—one animal is used per antigen. The animal will experience discomfort associated with the immunization and in particular the bleeding procedures. It is expensive and laborious to obtain antibodies specific to a large number of different antigens, since a similar large amount of animals is required.

On one occasion however, the possibility of immunizing individual animals with more than one antigen has been discussed in connection with a semi-automated method of hybridoma generation using mice immunized with multiple antigens and a novel antigen microarray assay (Proteomics 5: 4070-4081, 2005 and WO 03089471). In this document, mice were immunized with 10 μg of 5-10 different protein antigens having sizes ranging from about 12 to about 48 kDa in order to solve the bottleneck problem in providing monoclonal antibodies to proteins encoded by the human genome. In the discussion of the scientific paper it is stated that "It is also possible that increasing the number of immunogens for each animal may ultimately lower the number of positive clones in any one fusion. Indeed, subsequent production runs within our laboratory have shown that five antigens per animal are optimal". A major problem associated with immunizing with more than one antigen is, according to WO 03089471, immunodominance. In order to circumvent this problem, the animal was injected with several antigen boosters. Immunization with more than one antigen is not recommended, apart from perhaps in special cases involving automated procedures for generating mice monoclonal hybridoma B cell lines, in which case it is recommended to immunize with no more than 5-10 different purified protein antigens. In the patent application it is also suggested that that immunization might be carried out with up to 50 different antigens. However, no specific examples demonstrate that this approach will work with a reasonable expectation of success.

Conventionally obtained antibodies have several other drawbacks in addition to being relatively expensive and time consuming to produce. It may e.g. be difficult to obtain a sufficient response toward mammalian antigens. In general, the large degree of conservation of immunoglobulin structure, immunoglobulin receptor structures, etc. among mammals does in many cases give rise to inaccurate test results when using mammalian antibodies for e.g. detecting mammalian antigens. Also, the problems with protein A/protein G binding, interference with rheumatoid factor, and activation of mammalian complement are often encountered when using mammalian antibodies and mammalian antigens.

In The FASEB Journal 4:2528-2532, 2001 it is disclosed that by immunizing a chicken during a 20 day period with a total amount of about 30-300 μg antigen, an immune response could be detected about 2-3 weeks later. It is concluded that the egg yolk is a convenient source of polyclonal antibodies because:

- the quantity of antigen needed is much lower compared to rabbits,
- birds produce antibodies against highly conserved mammalian antigens,
- the use of complete Freunds adjuvant leads to very high and long lasting titers of yolk antibodies, starting as early as 16 days after the first immunization,
- the purification of antibodies is simple and quick, and a purity of 90% is easily attained by PEG precipitation,
- chicken are inexpensive to keep and easy to handle,
- chicken antibodies are acid- and heat-resistant and therefore might be orally applied to prevent or to cure intestinal diseases of young animals or humans.

The document does not however, discuss if specific antibodies can be generated in a much faster and much more inexpensive way.

It is thus known that a number of advantages are associated with obtaining antibodies in a non-invasive way from eggs from an immunized chicken rather than collecting blood from an immunized mammal. However, the time required for generating antibodies is not dramatically reduced when using hen/chicken antibodies. And also, a large amount of birds are used to generate antibodies in cases where a large amount of different antigens are used. The available literature in this field does not provide any suggestions for providing specific antibodies in a dramatically faster and more inexpensive way.

In Handbook of Laboratory Animal Science, Second Edition, Vol 1, Jann Hau e.g. it is disclosed that "For each antigen, there is a dose called the "window of immunogenicity." Too much or too little antigen may induce suppression, sensitization, tolerance, or other unwanted immunomodulation[7]. Very low doses (<1 to 5 μg) are used to induce hypersensitivity (allergy) and should be avoided in immunization of animals, particularly because booster injections may result in anaphylactic shock in the animals."

There exists a dogma within the field of immunology that repeated immunizations with low doses of allergen may result in anaphylactic shock and that it is not possible to immunize animals with a large amount of antigens.

SUMMARY OF INVENTION

Antibodies have been raised in animal hosts for decades using one antigen per animal. In the invention disclosed however, a large numbers of antigen specific antibodies can be obtained by immunizing a host with a large number of antigens. Thus, a scientific dogma and a technical prejudice have been overcome by successfully immunizing animals with a large number of antigens.

Normally, affinity chromatography is used for capturing antigen by means of immobilized antibodies. By reversing this principle, the possibility of isolating antigen specific antibodies from an antibody library arises. It follows that the likelihood of isolating polyclonal antibodies specific to any antigen increases with increasing number of different antigens used for immunization. The current invention herein discloses a tool for providing harvesting and isolating antibodies from a generated antibody library. Said antibody library is preferably a polyclonal antibody library generated by immunization of a vertebrate organism using a pool of antigens such as a library of primary antigens. The vertebrate organism is preferably a hen of the species *Gallus gallus*. The library of primary antigens may comprise a multitude of compounds, preferably peptides that are capable of raising an immunogenic response in the host animal in combination with the carriers and adjuvants with which the library of primary antigens is co-immunized. Immunization of a host using said library of primary antigens bring about an immune response resulting in the generation of a large number of polyclonal antibodies, each specific towards a certain epitope of a primary antigen.

The present invention discloses a method for harvesting these antibodies using a secondary antigen, which may or may not differ in global structure from said primary antigen, nonetheless having an epitope coordinating the same paratope on the antibody as the primary antigen used for immunization. The method furthermore comprises immobilization of said secondary antigen on a surface that subsequently is brought into contact with the generated antibody library whereupon complexes between antigen and antibody will form. Unspecifically bound antibodies are removed by washing whereafter antibodies specifically bound to the immobilized secondary antigens are recovered and utilized to for research and industry and in the treatment of diseases and disorders.

Finally, the present invention relates to the products resulting from the various methods.

DEFINITIONS

Adjuvant: Any substance whose admixture with an administered immunogenic determinant/antigen increases or otherwise modifies the immune response to said determinant.

Amino acid: Any synthetic or naturally occurring amino carboxylic acid, including any amino acid occurring in peptides and polypeptides including proteins and enzymes synthesized in vivo. Natural amino acids comprise an amino terminal part ($NH_2$) and a carboxy terminal part (COOH) separated by a central part comprising a carbon atom, or a chain of carbon atoms, comprising at least one side chain or functional group. $NH_2$ refers to the amino group present at the amino terminal end of an amino acid or peptide, and COOH refers to the carboxy group present at the carboxy terminal end of an amino acid or peptide. The generic term amino acid comprises both natural and non-natural amino acids. Natural amino acids of standard nomenclature as listed in J. Biol. Chem., 243:3552-59 (1969) and adopted in 37 C.F.R., section 1.822(b)(2) belong to the group of amino acids listed in Table 2 herein below. Non-natural amino acids are those not listed in Table 2. Examples of non-natural amino acids are those listed e.g. in 37 C.F.R. section 1.822(b)(4), all of which are incorporated herein by reference. Further examples of non-natural amino acids are listed herein below. Amino acid residues described herein can be in the "D" or "L" isomeric form.

TABLE 2

Natural amino acids and their respective codes.

| Symbols | | |
|---|---|---|
| 1-Letter | 3-Letter | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| U | Sec | selenocysteine |
| O | Pyl | pyrrolysine |

Amino acid residue: the term "amino acid residue" is meant to encompass amino acids, either standard amino acids, non-standard amino acids or pseudo-amino acids, which have been reacted with at least one other species, such as 2, for example 3, such as more than 3 other species. In particular amino acid residues may comprise an acyl bond in place of a free carboxyl group and/or an amine-bond and/or amide bond in place of a free amine group. Furthermore, reacted amino acids residues may comprise an ester or thioester bond in place of an amide bond Amino acid precursor: Moiety capable of generating an amino acid residue following incorporation of the precursor into a peptide.

Antibody: Immunoglobulin molecule or immunologically active portion thereof, i.e. molecules that contain an "antigen binding site" or paratope. Immunoglobulins may be natural or wholly or partially synthetically produced. All fragments and derivatives thereof which maintain specific binding ability are also included in the term. The term also covers any polypeptide having a binding domain which is homologous or largely homologous, such as at least 95% identical, to an immunoglobulin binding domain. These polypeptides may be derived from natural sources, or partly or wholly synthetically produced. An antibody may be monoclonal or polyclonal. The antibody may be a member of any immunoglobulin class, including IgY, IgG, IgM, IgA, IgD, and IgE. Derivatives of the IgY class, however, are preferred in the present invention. An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

Antibody fragment: refers to any derivative of an antibody which is less than full-length. Preferably, the antibody fragment retains at least a significant portion of the full-length antibody's specific binding ability. Examples of antibody fragments include, but are not limited to, Fab, Fab', F(ab')$_2$, scFv, Fv, dsFv diabody, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids. Antibody is used interchangeably herein with fragments thereof capable of binding an antigen and the term antibody generally also covers antigen binding fragments of the antibody.

Antigen: Any substance that can bind to a specific antibody.

Boost: To boost by a booster shot or dose is to give an additional dose of an immunizing agent, such as a vaccine, given at a time after the initial dose to sustain the immune response elicited by the previous dose of the same agent.

Bursa of Fabricius: A thymus-like specialized lymphoid gland in birds that is an outgrowth of the cloaca and the site of hematopoiesis and B cell maturation in birds. It is thus the residence of antibody producing B cells.

Conjugated: An association formed between an immunogenic determinant and a carrier. The association may be a physical association generated e.g. by the formation of a chemical bond, such as e.g. a covalent bond, formed between the immunogenic determinant and the carrier.

Carriers: Entity or compound to which antigens are coupled to aid in the induction of an immune response.

Chemistry:

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical.

Where the term "alkyl" is used, either alone or within other terms such as "haloalkyl" and "alkylsulfonyl", it embraces linear or branched radicals having one to about twenty carbon atoms or, preferably, one to about twelve carbon atoms. Preferred alkyl radicals are "lower alkyl" radicals having one to about ten carbon atoms, such as lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Branched chain isomers of straight chain alkyl groups, include, but are not limited to, the following which are provided by way of example: —$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_3)(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)CH(CH_3)_2$, —$CH(CH_2CH_3)CH(CH_3)CH(CH_3)(CH_2CH_3)$, and others. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "alkenyl" embraces linear or branched radicals having at least one carbon-carbon double bond of two to about twenty carbon atoms, such as from two to about twelve carbon atoms, for example from two to about eight carbon atoms. Preferred alkyl radicals are "lower alkenyl" radicals having two to about six carbon atoms. Examples of such radicals include ethenyl, n-propenyl, butenyl, and the like. When substituted, the "alkenyl" or "lower alkenyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "halo" means halogens such as fluorine, chlorine, bromine or iodine atoms. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" preferably embraces radicals having 1-6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The "haloalkyl" or "lower haloalkyl" can optionally be further substituted. When further substituted, the "haloalkyl" or "lower haloalkyl" can further comprise one or more radicals selected from the group of radicals consisting of hydroxy, primary amine, carboxy, acid chloride, sulfonyl chloride, sulphonate, nitro, cyano, isothiocyanate, phosphonyl, sulphonyl, sulfamyl, carbonyl, and thiolyl.

The term "hydroxyalkyl" embraces linear or branched alkyl radicals having from one to about ten carbon atoms any one of which may be substituted with one or more hydroxyl radicals. Hydroxyalkyl radicals can be "lower hydroxyalkyl" radicals preferably having one to six carbon atoms and one or more hydroxyl radicals. Examples of such radicals include hydroxymethyl, hydroxyethyl, hydroxypropyl, hydroxybutyl and hydroxyhexyl. The "hydroxyalkyl" or "lower hydroxyalkyl" can optionally be further substituted. When further substituted, the "hydroxyalkyl" or "lower hydroxyalkyl" can further comprise one or more radicals selected from the group of radicals consisting of primary amine, carboxy, acid chloride, sulfonyl chloride, sulphonate, nitro, cyano, isothiocyanate, halogen, phosphonyl, sulphonyl, sulfamyl, carbonyl, and thiolyl.

The terms "alkoxy" and "alkoxyalkyl" embrace linear or branched oxy-containing radicals each having alkyl portions of one to about ten carbon atoms, such as methoxy radical. Alkoxy radicals can be "lower alkoxy" radicals having one to six carbon atoms.

Examples of such radicals include methoxy, ethoxy, propoxy, butoxy and tert-butoxy. The term "alkoxyalkyl" also embraces alkyl radicals having two or more alkoxy radicals attached to the alkyl radical, that is, to form monoalkoxyalkyl and dialkoxyalkyl radicals. Alkoxyalkyl radicals can be "lower alkoxyalkyl" radicals having one to six carbon atoms and one or two alkoxy radicals. Examples of such radicals include methoxymethyl, methoxyethyl, ethoxyethyl, methoxybutyl and metoxypropyl. The alkyl in said "alkoxyalkyl" can be substituted with one or more of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. When e.g. the above "alkoxyl" or "alkoxyalkyl" radicals are substituted with one or more halo atoms, such as fluoro, chloro or bromo, "haloalkoxy" or "haloalkoxyalkyl" radicals are provided.

Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one, two or three rings wherein such rings may be attached together in a pendent manner or may be fused. When substituted, "aryl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "aryl" include aromatic radicals such as phenyl, pentafluorphenyl, naphthyl, tetrahydronaphthyl, indane and biphenyl.

The term "heterocyclic" embraces saturated, partially saturated and unsaturated heteroatom-containing ring-shaped radicals, where the heteroatoms may be selected from nitrogen, sulfur and oxygen. When substituted, "heterocyclic" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of saturated heterocyclic radicals include e.g. saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g. thiazolidinyl, etc.]. Examples of partially saturated heterocyclic radicals include dihydrothiophene, dihydropyran, dihydrofuran and dihydrothiazole.

The term "heteroaryl" embraces unsaturated heterocyclic radicals. When substituted, "heteroaryl" can comprise one or more radicals selected from the group of radicals consisting of hydroxy, primary amine, secondary amine, carboxy, acid chloride, sulfonyl chloride, sulphonate, nitro, cyano, isothiocyanate, halogen, phosphonyl, sulphonyl, sulfamyl, carbonyl, and thiolyl. Examples of unsaturated heterocyclic radicals, also termed "heteroaryl" radicals, include e.g. unsaturated 5 to 6 membered heteromonocyclic group containing 1 to 4 nitrogen atoms, for example, pyrrolyl, pyrrolinyl, imidazolyl, pyrazolyl 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term "heteroaryl" or "unsaturated heterocyclic radical" also embraces radicals where heterocyclic radicals are fused with aryl radicals. Examples of such fused bicyclic radicals include benzofuran, benzothiophene, and the like. Said "heterocyclic group" can be substituted with one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl, said substitution generating a substituted "heteroaryl", optionally a substituted "heteroaryl" fused with an "aryl" radical which can be substituted or un-substituted. When substituted, the "aryl" is substituted as described herein above. Preferred heterocyclic radicals include five to ten membered fused or unfused radicals. More preferred examples or heteroaryl radicals include benzofuryl, 2,3-dihydrobenzofuryl, benzotrienyl, indolyl, dihydroindolyl, chromanyl, benzopyran, thiochromanyl, benzothiopyran, benzodioxolyl, benzodioxanyl, pyridyl, thienyl, thiazolyl, oxazolyl, furyl, and pyrazinyl.

The term "sulfonyl", whether used alone or linked to other terms such as alkylsulfonyl, denotes respectively divalent radicals —SO$_2$—.

"Alkylsulfonyl" embraces alkyl radicals attached to a sulfonyl radical, where alkyl can be substituted is defined as above. Alkylsulfonyl radicals can be "lower alkylsulfonyl" radicals having one to six carbon atoms. Examples of such lower alkylsulfonyl radicals include methylsulfonyl, ethylsulfonyl and propylsulfonyl.

The term "arylsulfonyl" embraces aryl radicals as defined above, including substituted aryl radicals, attached to a sulfonyl radical. Examples of such radicals include phenylsulfonyl.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—SO$_2$NH$_2$).

The terms "N-alkylaminosulfonyl" and "N,N-dialkylaminosulfonyl" denote sulfamyl radicals substituted respectively, with one alkyl radical, or two alkyl radicals, optionally substituted alkyl radicals as described herein above. Akylaminosulfonyl radicals can be "lower alkylaminosulfonyl" radicals having one to six carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical, optionally substituted aryl and/or alkyl radicals as described herein above. N-alkyl-N-arylaminosulfonyl radicals can be "lower N-alkyl-N-arylsulfonyl" radicals having alkyl radicals of one to six carbon atoms. Examples of such lower N-alkyl-N-aryl aminosulfonyl radicals include N-methylphenylaminosulfonyl and N-ethyl-phenylaminosulfonyl.

The terms "carboxy" or "carboxyl", whether used alone or with other terms, such as "carboxyalkyl", denotes —CO$_2$H.

The term "carboxyalkyl" or "alkanoyl" embraces radicals having a carboxy radical as defined above, attached to an alkyl radical as described herein above. When substituted, the "alkyl" or "lower alkyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples of "carboxyalkyl" radicals include formyl, acetyl, propionyl(propanoyl), butanoyl(butyryl), isobutanoyl(isobutyryl), valeryl (pentanoyl), isovaleryl, pivaloyl, hexanoyl or the like.

The term "carbonyl", whether used alone or with other terms, such as "alkylcarbonyl", denotes —(C═O)—.

The term "alkylcarbonyl" embraces radicals having a carbonyl radical substituted with an alkyl radical. Alkylcarbonyl radicals can be "lower alkylcarbonyl" radicals having from one to six carbon atoms. Examples of such radicals include methylcarbonyl and ethylcarbonyl. When substituted, the "alkyl" or "lower alkyl" of the "alkylcarbonyl" can comprise one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, and thiolyl.

The term "alkylcarbonylalkyl", denotes an alkyl radical substituted with an "alkylcarbonyl" radical as described herein above. Both the alkyl and the alkylcarbonyl can be substituted as described herein above.

The term "alkoxycarbonyl" means a radical containing an alkoxy radical, as defined above, attached via an oxygen atom to a carbonyl radical. "Lower alkoxycarbonyl" embraces alkoxy radicals preferably having from one to six carbon atoms. Examples of "lower alkoxycarbonyl" ester radicals include substituted or unsubstituted methoxycarbonyl, ethoxycarbonyl, propoxycarbonyl, butoxycarbonyl and hexyloxycarbonyl.

The term "alkoxycarbonylalkyl" embraces radicals having "alkoxycarbonyl", as defined above substituted to an optionally substituted alkyl radical. Alkoxycarbonylalkyl radicals can be "lower alkoxycarbonylalkyl" having lower alkoxycarbonyl radicals as defined above attached to one to six carbon atoms. Examples of such lower alkoxycarbonylalkyl radicals include methoxycarbonylmethyl, tert-butoxycarbonylethyl, and methoxycarbonylethyl.

The term "aminocarbonyl" when used by itself or with other terms such as "aminocarbonylalkyl", "N-alkylaminocarbonyl", "N-arylaminocarbonyl, "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(═O)NH$_2$.

The terms "N-alkylaminocarbonyl" and "N,N-dialkylaminocarbonyl" denote aminocarbonyl radicals which have been substituted with one alkyl radical and with two alkyl radicals, respectively. The alkyl radicals can be substituted as described herein above. "Lower alkylaminocarbonyl" comprises lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical, wherein such radicals can be substituted as described herein above.

The term "aminocarbonylalkyl" embraces optionally substituted alkyl radicals substituted with aminocarbonyl radicals.

The term "N-cycloalkylaminocarbonyl" denotes aminocarbonyl radicals which have been substituted with at least one optionally substituted cycloalkyl radical. "Lower cycloalkylaminocarbonyl" comprises lower cycloalkyl radicals of three to seven carbon atoms, attached to an aminocarbonyl radical.

The term "aminoalkyl" embraces alkyl radicals substituted with one or more amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl.

The term "alkylaminoalkyl" embraces aminoalkyl radicals having the nitrogen atom substituted with an optionally substituted alkyl radical.

The term "amidino" denotes an —C(═NH)—NH$_2$ radical.

The term "cyanoamidino" denotes an —C(═N—CN)—NH$_2$ radical.

The term "heterocyclicalkyl" embraces heterocyclic-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Heterocyclicalkyl radicals can be "lower heterocyclicalkyl" radicals preferably having from one to six carbon atoms and a heterocyclic radical. Examples include such radicals as pyrrolidinylmethyl, pyridylmethyl and thienylmethyl.

The term "aralkyl" embraces aryl-substituted alkyl radicals. The alkyl radicals can themselves be substituted by one or more radicals selected from the group of radicals consisting of hydroxy, primary amino, carboxy, acid chloride, sulfonyl chloride, sulphonate, nitro, cyano, isothiocyanate, halogen, phosphonyl, sulphonyl, sulfamyl, carbonyl, and thiolyl. Aralkyl radicals can be "lower aralkyl" radicals having aryl radicals attached to alkyl radicals having from one to six carbon atoms. Examples of such radicals include benzyl, diphenylmethyl, triphenylmethyl, phenylethyl and diphenylethyl.

The aryl in said aralkyl may be additionally substituted with halo, alkyl, alkoxy, halkoalkyl and haloalkoxy. The terms benzyl and phenylmethyl are interchangeable.

The term "cycloalkyl" embraces radicals having three to ten carbon atoms. Cycloalkyl radicals can be "lower cycloalkyl" radicals having three to seven carbon atoms. Examples include radicals such as cyclopropyl, cyclobutyl, cyclopentyl, cyclohexyl and cycloheptyl. The "cycloalkyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl.

The term "cycloalkenyl" embraces unsaturated cyclic radicals having three to ten carbon atoms. The "cycloalkenyl" can optionally be substituted by one or more radicals selected from the group of radicals consisting of hydroxy, primary amine, carboxy, acid chloride, sulfonyl chloride, sulphonate, nitro, cyano, isothiocyanate, halogen, phosphonyl, sulphonyl, sulfamyl, carbonyl, and thiolyl. Examples include cyclobutenyl, cyclopentenyl, cyclohexenyl and cycloheptenyl, which can optionally be substituted as described above.

The term "alkylthio" embraces radicals containing a linear or branched alkyl radical, of one to ten carbon atoms, attached to a divalent sulfur atom. An example of "alkylthio" is methylthio, (CH$_3$—S—). The alkyl radical can be substituted as described herein above.

The term "alkylsulfinyl" embraces radicals containing a linear or branched alkyl radical, of one to ten carbon atoms, attached to a divalent —S(═O)— atom. The alkyl radical can be substituted as described herein above.

The term "aminoalkyl" embraces alkyl radicals substituted with amino radicals. The alkyl radicals can be further substituted by one or more radicals selected from the group of radicals consisting of hydroxy, carboxy, acid chloride, sulfonyl chloride, sulphonate, nitro, cyano, isothiocyanate, halogen, phosphonyl, sulphonyl, sulfamyl, carbonyl, and thiolyl. Aminoalkyl radicals can be "lower aminoalkyl" having from one to six carbon atoms. Examples include aminomethyl, aminoethyl and aminobutyl which can optionally be further substituted as described above.

The term "alkylaminoalkyl" embraces aminoalkyl radicals having the nitrogen atom substituted with at least one alkyl radical. Alkylaminoalkyl radicals can be "lower alkylaminoalkyl" having one to six carbon atoms attached to a lower aminoalkyl radical as described above. The alkyl radical can be substituted as described herein above.

The terms "N-alkylamino" and "N,N-dialkylamino" denote amino groups which have been substituted with one alkyl radical and with two alkyl radicals, respectively. The alkyl radical can be substituted as described herein above. Alkylamino radicals can be "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "arylamino" denotes amino groups which have been substituted with one or two aryl radicals, such as N-phenylamino. The "arylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The term "aralkylamino" denotes amino groups which have been substituted with one or two aralkyl radicals, such as N-benzylamino. The "aralkylamino" radicals may be further substituted on the aryl ring portion of the radical. Substitutions can include one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

The terms "N-alkyl-N-arylamino" and "N-aralkyl-N-alkylamino" denote amino groups which have been substituted with one aralkyl and one alkyl radical, or one aryl and one alkyl radical, respectively, to an amino group. The aralkyl and/or alkyl and/or aryl radicals can be substituted as described herein above.

The terms "N-arylaminoalkyl" and "N-aralkylaminoalkyl" denote amino groups which have been substituted with one aryl radicals or one aralkyl radical, respectively, and having the amino group attached to an alkyl radical. The aralkyl and/or alkyl and/or aryl radicals can be substituted as described herein above. Arylaminoalkyl radicals can be "lower arylaminoalkyl" having the arylamino radical attached to one to six carbon atoms. Examples of such radicals include N-phenylaminomethyl and N-phenyl-N-methylaminomethyl.

The terms "N-alkyl-N-arylaminoalkyl", and "N-aralkyl-N-alkylaminoalkyl" denote N-alkyl-N-arylamino and N-alkyl-N-aralkylamino groups, respectively, and having the amino group attached to alkyl radicals which can be substituted as described herein above.

The term "acyl", whether used alone, or within a term such as "acylamino", denotes a radical provided by the residue after removal of hydroxyl from an organic acid.

The term "acylamino" embraces an amino radical substituted with an acyl group. An examples of an "acylamino" radical is acetylamino or acetamido ($CH_3C(=O)-NH-$) where the amine may be further substituted with alkyl, aryl or aralkyl, wherein said alkyl, aryl or aralkyl can be substituted as described herein above.

The term "arylthio" embraces aryl radicals of six to ten carbon atoms, attached to a divalent sulfur atom. The aryl can be substituted as described herein above. An example of "arylthio" is phenylthio.

The term "aralkylthio" embraces aralkyl radicals as described above, attached to a divalent sulfur atom. The aralkyl radicals can be further substituted as described herein above. An example of "aralkylthio" is benzylthio.

The term "aryloxy" embraces aryl radicals, as defined above, attached to an oxygen atom. The aryl can be substituted as described herein above. Examples of such radicals include phenoxy.

The term "aralkoxy" embraces oxy-containing aralkyl radicals attached through an oxygen atom to other radicals. The aralkyl can be substituted as described herein above. Aralkoxy radicals can be "lower aralkoxy" radicals having phenyl radicals attached to lower alkoxy radical as described above.

The term "haloaralkyl" embraces aryl radicals as defined above attached to haloalkyl radicals. The aryl can be further substituted as described herein above.

The term "carboxyhaloalkyl" embraces carboxyalkyl radicals as defined above having halo radicals attached to the alkyl portion. The alkyl portion can be further substituted as described herein above.

The term "alkoxycarbonylhaloalkyl" embraces alkoxycarbonyl radicals as defined above substituted on a haloalkyl radical. The haloalkyl radical can be further substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "aminocarbonylhaloalkyl" embraces aminocarbonyl radicals as defined above substituted on an optionally substituted haloalkyl radical wherein the alkyl is substituted by one or more of hydroxy, amino, carboxy, acid chloride, sulfonyl chloride, sulphonate, nitro, cyano, isothiocyanate, phosphonyl, sulphonyl, sulfamyl, carbonyl, and thiolyl.

The term "alkylaminocarbonylhaloalkyl" embraces alkylaminocarbonyl radicals as defined above substituted on an optionally substituted haloalkyl radical as described above.

The term "alkoxycarbonylcyanoalkenyl" embraces alkoxycarbonyl radicals as defined above, and a cyano radical, both substituted on an optionally substituted alkenyl radical.

The term "carboxyalkylaminocarbonyl" embraces aminocarbonyl radicals substituted with carboxyalkyl radicals, as defined above. The carboxyalkyl can be further substituted. Substitutions can include one or more of hydroxy, amino, acid chloride, sulfonyl chloride, sulphonate, nitro, cyano, isothiocyanate, halogen, phosphonyl, sulphonyl, sulfamyl, carbonyl, and thiolyl.

The term "aralkoxycarbonylalkylaminocarbonyl" embraces aminocarbonyl radicals substituted with aryl-substituted alkoxycarbonyl radicals, as defined above.

The term "cycloalkylalkyl" embraces cycloalkyl radicals having three to ten carbon atoms attached to an alkyl radical, as defined above. Cycloalkylalkyl radicals can be "lower cycloalkylalkyl" radicals having cycloalkyl radicals attached to lower alkyl radicals as defined above. Examples include radicals such as cyclopropylmethyl, cyclobutylmethyl, and cyclohexylethyl.

The term "aralkenyl" embraces optionally substituted aryl radicals attached to alkenyl radicals having two to ten carbon atoms, such as phenylbutenyl, and phenylethenyl or styryl. When substituted the aryl can be substituted with one or more of hydroxy, amino, carboxy, acid chloride, sulfonyl chloride, sulphonate, nitro, cyano, isothiocyanate, halogen, phosphonyl, sulphonyl, sulfamyl, carbonyl, and thiolyl.

Co-immunization: Immunization by means of separate and/or sequential administration to an individual of an immunogenic determinant and a carrier.

"Conditions suitable for binding": means those conditions (in terms of salt concentration, pH, detergent, polypeptide concentration, temperature, etc.) which allow for binding to occur between a ligand and its binding partner in solution i.e. the binding between an antigen and an antibody. Preferably, the conditions are not so lenient that a significant amount of nonspecific binding occurs.

Derivative: refers to polypeptides derived from naturally occurring compounds by chemical modifications such as ubiquitination, labelling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

Epitope: A specific site on a protein to which only certain antibodies bind.

Host: as used herein is any species immunized and used for the production of an antibody library according to the present invention. The term includes any animal, mammalian or vertebrate. Herein the preferred host is an avian species and preferably a female of the species.

Immunization: Process of inducing an immunological response in an organism.

Immunological response: Response to an immunogenic composition comprising an immunogenic determinant. An immune response involves the development in the host of a cellular- and/or antibody-mediated response to the administered composition or vaccine in question. An immune response generally involves the action of one or more of i) the antibodies raised, ii) B cells, iii) helper T cells, iv) suppressor T cells, and v) cytotoxic T cells, directed specifically to an immunogenic determinant present in an administered immunogenic composition.

Immunogenic composition: Composition capable of raising an immunological response in an individual.

Immunogenic: Functionality associated with an entity capable of eliciting an immunological response.

Immunostimulating effect: Functionality associated with an entity capable of eliciting an enhanced immune response. An enhanced immune response will be understood within the meaning of the observed difference in the immune response measured as an enhancement of an antibody production and/or a cytotoxic T-cell activity, or otherwise registered, when an immunogenic composition is administered in the presence or absence, respectively, of the entity. An immunogenic composition comprising the entity will be understood as being a composition according to the present invention.

Individual: Any species or subspecies of bird, mammal, fish, amphibian, or reptile. The term includes human and animal species, such as farm animals. By the term "farm animal" is meant animals bred on farms mainly for production purposes, for example for the production of meat, milk, eggs or wool. Examples of farm animals include cattle, pigs, sheep, goat, poultry, such as turkey, chickens or ducks.

Isolated: used in connection with, polypeptides, and antibodies disclosed herein 'isolated' refers to these having been identified and separated and/or recovered from a component of their natural, typically cellular, environment. Nucleic acids, polypeptides, and antibodies of the invention are preferably isolated, and vaccines and other compositions of the invention preferably comprise isolated nucleic acids, polypeptides or isolated antibodies.

Isolated polypeptide: a protein, or a variant or fragment thereof, which constitutes 90% or more of the protein contents of a given preparation as evaluated by standard methods known in the art of protein chemistry.

A polypeptide "fragment", "portion", or "segment": is a stretch of amino acid residues of at least about 5 amino acids, often at least about 7 amino acids, typically at least about 9 to 13 amino acids, such as at least about 17 or more amino acids in various embodiments. To be active, any polypeptide, peptide or polypeptide fragment must have sufficient length to display biologic and/or immunologic activity on their own, or when conjugated to a carrier.

Library: a plurality of entities such as antigens or antibodies

Ligand: In biochemistry, a ligand is an effector, a molecule that binds to a site on a macromolecule's surface by intermolecular forces, thereby changing the chemical conformation of the macromolecule. Once a molecule's conformation has changed, its ability to function in other chemical reactions is altered. This binding is usually a reversible reaction, i.e. it can be undone. Actual coordinate covalent bonds between a ligand and its target molecule are rare in biological systems. Ligands include substrates, inhibitors, activators, and neurotransmitters. Herein an antigen is a ligand to an antibody.

Monoclonal antibody: (mAB) A single type of antibody that is directed against a specific epitope (antigen, antigenic determinant) and is produced by a single clone of B cells or a single hybridoma cell line, which is formed by the fusion of a lymphocyte cell with a myeloma cell. Some myeloma cells synthesize single antibodies naturally.

Non-natural amino acid: Any amino acid not included in Table 2 herein above. Non-natural amino acids include, but are not limited to modified amino acids, pseudo-amino acids, L-amino acids, and stereoisomers of D-amino acids.

Non-standard amino acid: a non-standard amino acid is capable of being incorporated into a peptide or peptide like structure by translation mediated by a ribosome. A non-standard amino acid according to the present invention is any amino acid comprising an amino group and a carboxyl group separated by an α-carbon. The amino acid may for example be selected from the group consisting of, Aib, Nal, Sar, Orn, Lysine analogues DAP and DAPA or any of the amino acids described in U.S. Pat. No. 5,573,905. Furthermore, non-standard amino acids may be any of the above mentioned or any standard amino acids which further comprises one or more moieties selected from the group consisting of hydroxyl, bromo, fluoro, chloro, iodo, mercapto, thio, cyano, alkylthio, heterocycle, aryl, heteroaryl, carboxyl, carboalkoyl, alkyl, alkenyl, nitro, amino, alkoxyl and/or amido. The non-standard amino acid is capable of being incorporated into a peptide or peptide like structure by translation mediated by a wt, mutant, modified or recombinant ribosome.

Normal physiological condition: means conditions that are typical inside a living organism or a cell. While it is recognized that some organs or organisms provide extreme conditions, the intra-organismal and intracellular environment normally varies around pH 7 (i.e., from pH 6.5 to pH 7.5), contains water as the predominant solvent, and exists at a temperature above 0° C. and below 50° C. It will be recognized that the concentration of various salts depends on the organ, organism, cell, or cellular compartment used as a reference.

Nucleic acid: A chain or sequence of nucleotides that convey genetic information. In regards to the present invention the nucleic acid is a deoxyribonucleic acid (DNA).

Nucleic acid construct: A genetically engineered nucleic acid. A (nucleic acid) construct typically comprises several elements such as genes or fragments of same, promoters, enhancers, terminators, polyA tails, linkers, markers or others.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Peptide: Plurality of covalently linked amino acid residues defining a sequence and linked by amide bonds. The term is used analogously with oligopeptide and polypeptide. The amino acids may be both natural amino acids and non-natural amino acids, including any combination thereof. The natural and/or non-natural amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Peptide library: A library of peptides of similar lengths covering all the possible combinations of the containing moieties. A peptide library may also be a library comprising e.g. a specific fraction of an amino acid sequence from a number of different proteins with known sequences.

Pharmaceutical carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Plurality: At least two.

Polyclonal antibody: Polyclonal antibodies are a pool of immunoglobulins which arise from more than one clone of B-lymphocyte cells Polypeptide derivatives: polypeptides derived from naturally occurring XXX by chemical modifications such as ubiquitination, labelling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

Primary antigen: Any substance inducing an immunological response and also bind to a specific antibody. The primary antigen is preferably a synthetic peptide present in a peptide library.

Pseudo-amino acid: an entity comprising a substituted amino group or/and carboxyl group separated by an α-carbon or α-amine capable of being incorporated into a peptide by ribosomes. For example, a pseudo amino acid may comprise a thiol group and a carboxyl group separated by an α-carbon resulting in a thioester bond in the backbone.

Residue: A polymer comprises a sequence of covalently linked residues, wherein each residue comprises a functional group.

Secondary antigen: Any substance that can bind to a specific antibody of the generated antibody library according to the present invention.

Surfactant: A surface active agents capable of reducing the surface tension of a liquid in which it is dissolved. A surfactant is a compound containing a polar group which is hydrophilic and a non polar group which is hydrophobic and often composed of a fatty chain.

Vaccine/immunization cocktail/immunogenic composition: A substance or composition capable of inducing an immune response in an animal/host. An immune response being, an immune response (humoral/antibody and/or cellular) inducing memory in an organism, resulting in the generation of antibodies against the introduced agents/antigens. The composition may comprise one or more of the following: antigen(s), carriers, adjuvants and pharmaceutical carriers.

Variant: a variant of a given reference nucleic acid or polypeptide refers to a nucleic acid or polypeptide that displays a certain degree of sequence homology to said reference nucleic acid or polypeptide but is not identical to said reference nucleic acid or polypeptide.

DETAILED DESCRIPTION OF THE INVENTION

The present invention relates to a novel method for harvesting antibodies from a library of generated antibodies in a prompt and inexpensive manner.

Prior to the construction of the antibody library, one or more libraries of primary antigens are synthesized. If the primary antigen library is a peptide library this may be performed by random peptide synthesis. Subsequently the primary antigens may be coupled to a carrier optionally in combination with one or more adjuvants and used for the immunization of the host animals, preferably the hens of an avian species.

Antigen Library

It is an object of the present invention that the plurality of avian species each is immunized with a plurality of antigens, herein referred to as a primary antigen library. The primary antigens of the library may or may not be coupled to a carrier as described herein. The average numbers of primary antigens within such a library is in the range of from 2 to 100000.

A primary antigen library may be a peptide library constructed randomly by solid-phase-synthesis with controlled coupling to either tert-butyl-oxy-carbonyl (BOC) groups or Fluorenyl-methoxy-carbonyl (FMOC). Instead of producing the single peptides individually, they are all produced simultaneously. Peptides will be produced to cover all possible domains. This means that modified moieties such as glycosylated and phosphorylated moieties/amino acids also are represented. Employing the random coupling between the amino acids the peptides are produced fast, cheap and divided into smaller groups. A smaller group refers as an example to 10.000 antigens. A group can be generated by excluding certain moieties or modifications from the reaction.

A way of carrying out the present invention is to synthesize a peptide library with peptides of similar lengths covering all the possible combinations of the moieties disclosed in the above. Peptide synthesis may take place in solution or on a solid phase. A peptide library with peptides of a length of e.g. 6 of the 20 most often naturally occurring amino acids will thus in theory have $20^6$ different ways of combining the amino acids, and thus up to $20^6$ different peptides. The peptide library may also be a library comprising e.g. a specific fraction of the amino acid sequence from a number of different proteins with known sequences. The peptides must have lengths of at least 5 amino acids in order to be able to bind to the hypervariable loops of the Fab fragment of the antibody.

It follows that peptide libraries may also be prepared using more or less than the 20 most often occurring natural amino acids—in which case of course the theoretical number of different combinations will vary accordingly. Any of the above defined antigens comprising any of the above defined moieties with any of the above defined modifications may be combined to form part of the antigen library. Any of the resulting combinations may or may not be coupled to a carrier according to the above prior to immunization (with or without further mixing with an adjuvant).

Host

The host is the animal or individual used for the generation of the antibody libraries according to the present invention. The host may be an animal from the vertebrate phyla. Preferred animals are animals from either the mammalian or the avian orders. Avian animals are particularly preferred. Birds from the Galliformes order are most preferred. The Galliformes order of birds includes grouse, ptarmigan, capercaillie, partridges, pheasants, quails, turkeys and peacocks. These are mainly grain-eating, heavy-bodied, ground-nesting birds, capable of only short, rapid flights. The cocks are usually more colourful than the hens. A preferred bird according to the present invention is a *Gallus gallus* domestica either in the adult stage or as a chicken at the age of at least 17-19 weeks. Especially preferred are the females of any of the above mentioned avian species. Birds used for immunization should have an age of at least 17 weeks, preferably at least 19 weeks.

The hen of *Gallus gallus* domestica is ideal because it can produce about 1500 mg antibodies per month (about 50-100 mg antibodies per egg (AOEA 24: 925-934, 1996). In fact, antibodies can be obtained in a non-invasive manner from the chicken during the entire egg-laying period. Usually, about 2-10% of the antibodies are antigen specific (AOEA 24: 925-934, 1996). The percentage of antigen specific antibodies may be even higher as a response to immunization with a multitude of antigens.

It is an important aspect of the present invention to immunize a plurality of hosts for the production of antibody libraries. Therefore, the number of host, especially avian organisms, immunized is about 1000, such as about 2000, for example about 3000, such as about 4000, for example about 5000, such as about 5500, for example about 6000, such as about 6500, for example about 7000, such as about 75000, for example about 8000, such as about 8500, for example about 9000, such as about 9500, for example about 10000, such as about 10500, for example about 11000, such as about 115000, for example about 12000, such as about 12500, for example about 13000, such as about 13500, for example about 14000, such as about 14500, for example about 15000, such as about 16000, for example about 17000, such as about 18000, for example about 19000, such as about 20000, for example about 21000, such as about 22000, for example about 23000, such as about 24000, for example about 25000, such as about 26000, for example about 27000, such as about 28000, for example about 29000, such as about 30000, for example about 31000, such as about 32000, for example about 33000, such as about 34000, for example about 35000, such as about 36000, for example about 37000, such as about 38000, for example about 39000, such as about 40000, for example about 41000, such as about 42000, for example about 43000, such as about 44000, for example about 45000, such as about 50000.

Preferably, any number of hosts from 10 to 100000 is immunized. More preferably the number of hosts is between 100 and 50000, such as between 200 and 40000, 300 and 10000, 400 and 9000, 500 and 8000, 600 and 7000, 800 and 6000, 900 and 5500, 1000 and 5000.

Method of Immunization

Immunogenic compositions according to the invention may be administered to a host in effective amounts resulting in the optimum production of antibodies. The effective amount may vary according to a variety of factors such as the host's condition, weight, and age. Other factors include the mode of administration.

The immunogenic compositions may be provided to the individual by a variety of routes such as subcutaneous, topical, oral and intramuscular. Administration of pharmaceutical compositions is accomplished orally or parenterally. Methods of parenteral delivery include topical, intra-arterial (directly to the tissue), intramuscular, subcutaneous, intramedullary, intrathecal, intraventricular, intravenous, intraperitoneal, or intranasal administration. The present invention also has the objective of providing suitable topical, oral, systemic and parenteral pharmaceutical formulations for use in the methods of prophylaxis and treatment of the vaccine composition.

For example, the immunogenic compositions can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the vaccine, comprising any of the herein described compounds can be employed as a prophylactic or therapeutic agent. Also any and all conventional dosage forms that are known in the art to be appropriate for formulating injectable immunogenic peptide composition are encompassed, such as lyophilised forms and solutions, suspensions or emulsion forms containing, if required, conventional pharmaceutically acceptable carriers, diluents, preservatives, adjuvants, buffer components, etc.

Preferred modes of administration of the immunogenic composition according to the invention include, but are not limited to systemic administration, such as intravenous or subcutaneous administration, intradermal administration, intramuscular administration, intranasal administration, oral administration, rectal administration, vaginal administration, pulmonary administration and generally any form of mucosal administration. Furthermore, it is within the scope of the present invention that the means for any of the administration forms mentioned in the herein are included in the present invention.

Preferably, the method of administration involves injection. The animals may be immunized with the antigens intramuscularly, intrasplenically, intravenously, intraperitoneally, intradermally or subcutaneously or by any other suitable means. Most preferably the chickens kept under field conditions are immunized in the breast musculature with a pistol. This spares the chicken for a slow and stressing immunization. In the laboratory, chickens most preferably are vaccinated subcutaneously in the neck.

An immunogenic composition according to the present invention can be administered once, or any number of times such as two, three, four or five times. Administering the composition more than once has the effect of boosting the resulting immune response. The composition can further be boosted by administering it in a form or body part different from the previous administration. The booster shot is either a homologous or a heterologous booster shot. A homologous booster shot is a where the first and subsequent administrations comprise the same compositions and more specifically the same antigens and adjuvants. A heterologous booster shot is where identical antigen libraries are comprised in different compositions, i.e. different adjuvants and carriers.

The total number of immunizations will depend upon the type and dose of the antigen, as well as on the particular adjuvant and carrier employed. In a preferred embodiment, at least two administrations are given, such as 3, 4, 5, 6, 7, 8, 9, 10 or more administrations. If the antibody titres begin to decrease, further booster immunizations can be given.

It falls within the scope of the present invention that the means and modes of administration of the immunogenic composition are adapted to the host. A preferred recipient of the vaccine is an avian, such as a chicken of the species *Gallus gallus*.

An embodiment of the present invention includes an immunogenic composition further comprising a second active ingredient. The second active ingredient is selected from, but not limited the group of antibiotics, chemotherapeutics, anti-allergenics, cytokines, complement factors and co-stimulatory molecules of the immune system, any compound or supplement which may be of benefit to the host organism.

The total amount of peptide employed for each immunization may likewise vary. Amounts of about 1, 2, 3, 4, 5, 6, 7, 8, 9, 10, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 µg are preferably used in a single immunization. But amounts of about 1, 2, 3, 4, 5, 6, 7, 8, 9, 10, 15, 20, 25, 50, 75, 100, 125, 150, 175, 200, 250, or 500 mg may also be used in a single immunization.

The method of any of claims 1 to 106 further comprising administering said different antigens to said avian organism(s) in the presence of one or more carrier(s) covalently or non-covalently attached to at least some of said antigens.

The amount of different peptide antigens used for immunization of the animal is at least 15. As the aim of the present invention is to provide tools for rapidly isolating antigen specific antibodies, it is advantageous to immunize with even more antigens, as the likelihood thus increases of obtaining antibodies with specificity to most antigens. It is therefore preferable to immunize with at least about 25, 50, 51, 60, 70, 80, 90, 100, 150, 200, 250, 500, 1000, 5000, 10000, 50000, 100000, 500000, 1000000, or 5000000 different antigens. It is most preferable to immunize with a synthetically synthesized peptide library comprising, in theory, $20^6$ or more different peptide combinations.

The Antibody Library

The present invention relates to novel methods for harvesting antibodies from a library of generated antibodies in a prompt and inexpensive manner. Prior to the construction of the antibody library, one or more libraries of primary antigens have been synthesized as well as immunization of a plurality of avian organisms both methods described herein above.

According to theory, a complete antibody library will contain approximately $5.8 \times 10^6$ different antibodies as defined by different binding domains. This number is the result of the number of possible combinations of the variable regions, heavy and light chains of the antibodies. From this number, the antibody binding domains that recognize species specific sequences must be subtracted, since a species normally does not produce antibodies against itself. The exact number that has to be subtracted is unknown. It is expected that the immune system of an avian species reacts against at least 1.000 of 10.000 introduced primary antigens. Similar reactions are observed when animals react against different diseases at the same time. During immunization about 1 in 1000 lymphoid cells are activated. The chicken immune system contains approximately $10^9$ lymphoid cells, and as one in a thousand in theory should be activated, 1.000.000 cells are predicted to be able to react to a maximal stimulus. This is enough for reaction against 10.000 antigens.

The immunized birds are used for antibody production for an extended period of time such as about one year during which egg-laying is at its maximum. After this period, the birds are sacrificed and their bursas of Fabricius are harvested. This organ is a specialized organ that is the site of hematopoiesis in birds, which is the residence of the antibody producing B cells. These antibody producing cells may be fused to a myeloma cell line, thus creating a hybridoma cell line that produces specific antibodies. As each individual B cell and its immediate derivates—a specific B cell clone—only produce one type of antibody, these hybridoma cells are the source of monoclonal antibodies. In this manner monoclonal antibodies can be harvested and pooled into a library of monoclonal antibodies.

A further advantage of using avian species for the rapid production of antibody libraries, both poly- and monoclonal, is the avian specific immunoglobulin molecule, IgY. Although the terms IgG and IgY are commonly interchanged when speaking of chicken immunoglobulin, the accepted term is IgY. Chicken IgY is the functional equivalent to mammalian IgG. Immunoglobulins from chicken and other avian species bear some resemblance to mammalian IgG, but also display some unique structural and functional characteristics that distinguish them from IgG. Of similarities the following can be mentioned: IgY is divalent, degraded by papain to yield divalent Fab fragment and may be labelled i.e. enzyme-labeled, biotinylated and gold-labeled by standard procedures. It is found in the serum of chicken and is passed from the mother chicken to the embryo via the egg yolk, imparting a high concentration of chicken IgY to developing embryo. The "Y" in IgY comes from "yolk" and is the main antibody component in the egg yolk. Each yolk can yield 100-150 mg of antibody. As a measure of the amount of antibodies that may be produced according to the present invention, consider the following: A chicken produces around 100 mg IgY/egg, which corresponds to 30 g IgY per year. Depending on the number of birds immunized, kilograms of polyclonal antibodies may thus be harvested. Furthermore, the IgY molecule is more stable than the traditionally used IgG molecules and IgY has less cross-reactivity toward mammalian proteins. IgY binds neither rheumatoid factors nor Fc-receptors or proteins A or G, therefore the chicken's antibodies are unlikely to produce false positive reactions in certain immunochemical assays. Also, unlike mice, rabbits or other mammals, hens elicit a strong antibody response against highly conserved mammalian protein sequences, and the IgY antibodies can be obtained without sacrificing or bleeding the animal.

Primary and Secondary Antigens

From the antibody libraries generated, antibodies specific for virtually any antigen can be isolated. Antigen utilised as baits for retracting certain antibodies from said antibody library, is referred to as secondary antigen. The properties of the secondary antigens do not have to reflect those of the primary antigens used during immunization except for the presence of an analogous epitope in both primary and secondary antigens.

As the number of antibodies of varying specificity is high, any compound may find its complementary antibody comprised within the library. In this manner, antibodies specific to compounds that otherwise may not or can not be used for immunization, such as for example toxic substances, may be found. Specific antibodies can be harvested from the library according to the methods described herein below. Both primary and secondary antigens according to the present invention are preferably of peptide origin with a length of at least 5 amino acids, and may be derived either from natural sources, produced by recombinant methods, or synthesized artificially—or any mixtures thereof.

The primary and secondary antigens of the present invention share certain similarities but also differ in many aspects. Primary and secondary antigens according to the present invention are both defined as antigens with a length in the range of from 5 moieties as defined in the above to preferably less than 10000 moieties. The length of the primary and secondary antigens may thus be at least 6, 7, 8, 9, 10, 11, 12, 13, 14, 15, 16, 17, 18, 19, or 20 moieties or amino acid residues long, or at least 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 525, 550, 575, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, 9500 or 10000 moieties in length. Preferably, the primary and secondary antigens are between 5 and 500 moieties in length or any interval comprised therein, such as between, 5 and 400, 5 and 300, 5 and 200, 5 and 100, 5 and 50, 5 and 45, 5 and 40, 5 and 35, 5 and 30, 5 and 25, 5 and 24, 5 and 23, 5 and 22, 5 and 21, 5 and 20, 5 and 19, 5 and 18, 5 and 17, 5 and 16, 5 and 15, 5 and 14, 5 and 13, 5 and 12, 5 and 11, 5 and 10, 5 and 9, 5 and 8, 5 and 7 or 6 moieties in length. The primary and secondary antigens may furthermore be of a length in the range of from 10 to 20, 10 to 30, 10 to 40, 10 to 50, 10 to 60, 10 to 70, 10 to 80, 10 to 90, 10 to 100, 10 to 125, 10 to 150, 10 to 175, 10 to 200 moieties in length or from 15 to 20, 15 to 25, 15 to 30, 15 to 40, 15 to 50, 15 to 60, 15 to 70, 15 to 80, 15 to 90, 15 to 100, 15 to 125, 15 to 150, 15 to 175, 15 to 200, 20 to 50, 20 to 75, 20 to 100, 20 to 200, 20 to 250, 20 to 300, 20 to 350, 20 to 400 or more in length.

Certain differences can exist in the properties of primary and secondary antigens.

The primary antigens of the present invention are typically comprised in a library of antigens, meaning that there are more than 2 antigens present. Furthermore it can be a mix of antigens and/or peptides of different lengths, i.e. there may be short antigens and/or peptides present with a length as short as 5 moieties as well as longer antigens. Some or all of the antigens/peptides may also be in the form of peptides/polypeptides or proteins being either denatured or in their naturally folded form. It follows that proteins can be obtained from either a natural source or they can be recombinantly produced and subsequently purified. In addition the primary antigens comprise compounds capable of eliciting an immune response in an organism, said organism preferably being an avian. Examples of compounds thus included are natural and non-natural amino acid residues and combinations of these as natural amino acids only, as non-natural amino acids only or combination of either together into peptides or peptide-like compounds. Among the non-natural amino acids are the "unnatural" amino acids described by Mendel et al., (Annu. Rev. Biophys. Biomol. Struct. 1995 24:435-62—the document is hereby incorporated by reference and of special relevance for the present invention are the amino acids illustrated in FIG. 3 of said document). Be noted, that among these non-natural amino acids are acids, that do not comprise an amino ($-NH_2$) group, these are also included as moieties of the present invention. Preferably, the moieties of the present invention are naturally occurring amino acids.

The secondary antigen can possess similar chemical, biological and physical properties as the primary antigens, nevertheless it may differ in peptide length in the range of from 1 amino acid residues to preferably less than 10000 amino acid residues, such as from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, for example from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, such as from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, such as from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, for example from 2 to less than 5000 amino acid residues, for example from 2 to less than 1000 amino acid residues, such as from 2 to less than 900 amino acid residues, for example from 2 to less than 800 amino acid residues, such as from 2 to less than 700 amino acid residues, for example from 2 to less than 600 amino acid residues, such as from 2 to less than 500 amino acid residues, for example from 2 to less than 400 amino acid residues, such as from 2 to less than 300 amino acid residues, for example from 2 to less than 200 amino acid residues, such as from 2 to less than 100 amino acid residues, for example from 2 to less than 90 amino acid residues, such as from 2 to less than 80 amino acid residues, for example from 2 to less than 70 amino acid residues, such as from 2 to less than 60 amino acid residues, for example from 2 to less than 50 amino acid residues, such as from 2 to less than 40 amino acid residues, for example from 2 to less than 35 amino acid residues, such as from 2 to less than 30 amino acid residues, for example from 2 to less than 29 amino acid residues, such as from 2 to less than 28 amino acid residues, for example from 2 to less than 27 amino acid residues, such as from 2 to less than 26 amino acid residues, for example from 2 to less than 25 amino acid residues, such as from 2 to less than 24 amino acid residues, for example from 2 to less than 23 amino acid residues, such as from 2 to less than 22 amino acid residues, for example from 2 to less than 21 amino acid residues, such as from 2 to less than 30 amino acid residues, for example from 2 to less than 29 amino acid residues, such as from 2 to less than 28 amino acid residues, for example from 2 to less than 27 amino acid residues, such as from 2 to less than 26 amino acid residues, for example from 2 to less than 25 amino acid residues, such as from 2 to less than 24 amino acid residues, for example from 2 to less than 23 amino acid residues, such as from 2 to less than 22 amino acid residues, for example from 2 to less than 21 amino acid residues, such as from 2 to less than 20 amino acid residues, for example from 2 to less than 19 amino acid residues, such as from 2 to less than 18 amino acid residues, for example from 2 to less than 17 amino acid residues, such as from 2 to less than 16 amino acid residues, for example from 2 to less than 15 amino acid residues, such as from 2 to less than 14 amino acid residues, for example from 2 to less than 13 amino acid residues, such as from 2 to less than 12 amino acid residues, for example from 2 to less than 11 amino acid residues, such as from 2 to less than 10 amino acid residues, such as from 3 to less than 5000 amino acid residues, for example from 3 to less than 1000 amino acid residues, such as from 3 to less than 900 amino acid residues, for example from 3 to less than 800 amino acid residues, such as from 3 to less than 700 amino acid residues, for example from 3 to less than 600 amino acid residues, such as from 3 to less than 500 amino acid residues, for example from 3 to less than 400 amino acid residues, such as from 3 to less than 300 amino acid residues, for example from 3 to less than 200 amino acid residues, such as from 3 to less than 100 amino acid residues, for example from 3 to less than 90 amino acid residues, such as from 3 to less than 80 amino acid residues, for example from 3 to less than 70 amino acid residues, such as from 3 to less than 60 amino acid residues, for example from 3 to less than 50 amino acid residues, such as from 3 to less than 40 amino acid residues, for example from 3 to less than 35 amino acid residues, such as from 3 to less than 30 amino acid residues, for example from 3 to less than 29 amino acid residues, such as from 3 to less than 28 amino acid residues, for example from 3 to less than 27 amino acid residues, such as from 3 to less than 26 amino acid residues, for example from 3 to less than 25 amino acid residues, such as from 3 to less than 24 amino acid residues, for example from 3 to less than 23 amino acid residues, such as from 3 to less than 22 amino acid residues, for example from 3 to less than 21 amino acid residues, such as from 3 to less than 30 amino acid residues, for example from 3 to less than 29 amino acid residues, such as from 3 to less than 28 amino acid residues, for example from 3 to less than 27 amino acid residues, such as from 3 to less than 26 amino acid residues, for example from 3 to less than 25 amino acid residues, such as from 3 to less than 24 amino acid residues, for example from 3 to less than 23 amino acid residues, such as from 3 to less than 22 amino acid residues, for example from 3 to less than 21 amino acid residues, such as from 3 to less than 20 amino acid residues, for example from 3 to less than 19 amino acid residues, such as from 3 to less than 18 amino acid residues, for example from 3 to less than 17 amino acid residues, such as from 3 to less than 16 amino acid residues, for example from 3 to less than 15 amino acid residues, such as from 3 to less than 14 amino acid residues, for example from 3 to less than 13 amino acid residues, such as from 3 to less than 12 amino acid residues, for example from 3 to less than 11 amino acid residues, such as from 4 to less than 5000 amino acid residues, for example from 4 to less than 1000 amino acid residues, such as from 4 to less than 900 amino acid residues, for example from 4 to less than 800 amino acid residues, such as from 4 to less than 700 amino acid residues, for example from 4 to less than 600 amino acid residues, such as from 4 to less than 500 amino acid residues, for example from 4 to less than 400 amino acid residues, such as from 4 to less than 300 amino acid residues, for example from 4 to less than 200 amino acid residues, such as from 4 to less than 100 amino acid residues, for example from 4 to less than 90 amino acid residues, such as from 4 to less than 80 amino acid residues, for example from 4 to less than 70 amino acid residues, such as from 4 to less than 60 amino acid residues, for example from 4 to less than 50 amino acid residues, such as from 4 to less than 40 amino acid residues, for example from 4 to less than 35 amino acid residues, such as from 4 to less than 30 amino acid residues, for example from 4 to less than 29 amino acid residues, such as from 4 to less than 28 amino acid residues, for example from 4 to less than 27 amino acid residues, such as from 4 to less than 26 amino acid residues, for example from 4 to less than 25 amino acid residues, such as from 4 to less than 24 amino acid residues, for example from 4 to less than 23 amino acid residues, such as from 4 to less than 22 amino acid residues, for example from 4 to less than 21 amino acid residues, such as from 4 to less than 30 amino acid residues, for example from 4 to less than 29 amino acid residues, such as from 4 to less than 28 amino acid residues, for example from 4 to less than 27 amino acid residues, such as from 4 to less than 26 amino acid residues, for example from 4 to less than 25 amino acid residues, such as from 4 to less than 24 amino acid residues, for example from 4 to less than 23 amino acid residues, such as from 4 to less than 22 amino acid residues, for example from 4 to less than 21 amino acid residues, such as from 4 to less than 20 amino acid residues, for example from 4 to less than 19 amino acid residues, such as from 4 to less than 18 amino acid residues, for example from 4 to less than 17 amino acid residues, such as from 4 to less than 16 amino acid residues, for example from 4 to less than 15 amino acid residues, such as from 4 to less than 14 amino acid residues, for example from 4 to less than 13 amino acid residues, such as from 4 to less than 12 amino acid residues, for example from 4 to less than 11 amino acid residues, such as from 5 to less than 5000 amino acid residues, for example from 5 to less than 1000 amino acid residues, such as from 5 to less than 900 amino acid residues, for example from 5 to less than 800 amino acid residues, such as from 5 to less than 700 amino acid residues, for example from 5 to less than 600 amino acid residues, such as from 5 to less than 500 amino acid residues, for example from 5 to less than 400 amino acid residues, such as from 5 to less than 300 amino acid residues, for example from 5 to less than 200 amino acid residues, such as from 5 to less than 100 amino acid residues, for example from 5 to less than 90 amino acid residues, such as from 5 to less than 80 amino acid residues, for example from 5 to less than 70 amino acid residues, such as from 5 to less than 60 amino acid residues, for example from 5 to less than 50 amino acid residues, such as from 5 to less than 40 amino acid residues, for example from 5 to less than 35 amino acid residues, such as from 5 to less than 30 amino acid residues, for example from 5 to less than 29 amino acid residues, such as from 5 to less than 28 amino acid residues, for example from 5 to less than 27 amino acid residues, such as from 5 to less than 26 amino acid residues, for example from 5 to less than 25 amino acid residues, such as from 5 to less than 24 amino acid residues, for example from 5 to less than 23 amino acid residues, such as from 5 to less than 22 amino acid residues, for example from 5 to less than 21 amino acid residues, such as from 5 to less than 30 amino acid residues, for example from 5 to less than 29 amino acid residues, such as from 5 to less than 28 amino acid residues, for example from 5 to less than 27 amino acid residues, such as from 5 to less than 26 amino acid residues, for example from 5 to less than 25 amino acid residues, such as from 5 to less than 24 amino residues, for example from 5 to less than 23 amino acid residues, such as from 5 to less than 22 amino acid residues, for example from 5 to less than 21 amino acid residues, such as from 5 to less than 20 amino acid residues, for example from 5 to less than 19 amino acid residues, such as from 5 to less than 18 amino acid residues, for example from 5 to less than 17 amino acid residues, such as from 5 to less than 16 amino acid residues, for example from 5 to less than 15 amino acid residues, such as from 5 to less than 14 amino acid residues, for example from 5 to less than 13 amino acid residues, such as from 5 to less than 12 amino acid residues, for example from 5 to less than 11 amino acid residues, such as from 6 to less than 5000 amino acid residues, for example from 6 to less than 1000 amino acid residues, such as from 6 to less than 900 amino acid residues, for example from 6 to less than 800 amino acid residues, such as from 6 to less than 700 amino acid residues, for example from 6 to less than 600 amino acid residues, such as from 6 to less than 500 amino acid residues, for example from 6 to less than 400 amino acid residues, such as from 6 to less than 300 amino acid residues, for example from 6 to less than 200 amino acid residues, such as from 6 to less than 100 amino acid residues, for example from 6 to less than 90 amino acid residues, such as from 6 to less than 80 amino acid residues, for example from 6 to less than 70 amino acid residues, such as from 6 to less than 60 amino acid residues, for example from 6 to less than 50 amino acid residues, such as from 6 to less than 40 amino acid residues, for example from 6 to less than 35 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 20 amino acid residues, for example from 6 to less than 19 amino acid residues, such as from 6 to less than 18 amino acid residues, for example from 6 to less than 17 amino acid residues, such as from 6 to less than 16 amino acid residues, for example from 6 to less than 15 amino acid residues, such as from 6 to less than 14 amino acid residues, for example from 6 to less than 13 amino acid residues, such as from 6 to less than 12 amino acid residues, for example from 6 to less than 11 amino acid residues, such as from 7 to less than 5000 amino acid residues, for example from 7 to less than 1000 amino acid residues, such as from 7 to less than 900 amino acid residues, for example from 7 to less than 800 amino acid residues, such as from 7 to less than 700 amino acid residues, for example from 7 to less than 600 amino acid residues, such as from 7 to less than 500 amino acid residues, for example from 7 to less than 400 amino acid residues, such as from 7 to less than 300 amino acid residues, for example from 7 to less than 200 amino acid residues, such as from 7 to less than 100 amino acid residues, for example from 7 to less than 90 amino acid residues, such as from 7 to less than 80 amino acid residues, for example from 7 to less than 70 amino acid residues, such as from 7 to less than 60 amino acid residues, for example from 7 to less than 50 amino acid residues, such as from 7 to less than 40 amino acid residues, for example from 7 to less than 35 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 20 amino acid residues, for example from 7 to less than 19 amino acid residues, such as from 7 to less than 18 amino acid residues, for example from 7 to less than 17 amino acid residues, such as from 7 to less than 16 amino acid residues, for example from 7 to less than 15 amino acid residues, such as from 7 to less than 14 amino acid residues, for example from 7 to less than 13 amino acid residues, such as from 7 to less than 12 amino acid residues, for example from 7 to less than 11 amino acid residues, such as from 8 to less than 5000 amino acid residues, for example from 8 to less than 1000 amino acid residues, such as from 8 to less than 900 amino acid residues, for example from 8 to less than 800 amino acid residues, such as from 8 to less than 700 amino acid residues, for example from 8 to less than 600 amino acid residues, such as from 8 to less than 500 amino acid residues, for example from 8 to less than 400 amino acid residues, such as from 8 to less than 300 amino acid residues, for example from 8 to less than 200 amino acid residues, such as from 8 to less than 100 amino acid residues, for example from 8 to less than 90 amino acid residues, such as from 8 to less than 80 amino acid residues, for example from 8 to less than 70 amino acid residues, such as from 8 to less than 60 amino acid residues, for example from 8 to less than 50 amino acid residues, such as from 8 to less than 40 amino acid residues, for example from 8 to less than 35 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 20 amino acid residues, for example from 8 to less than 19 amino acid residues, such as from 8 to less than 18 amino acid residues, for example from 8 to less than 17 amino acid residues, such as from 8 to less than 16 amino acid residues, for example from 8 to less than 15 amino acid residues, such as from 8 to less than 14 amino acid residues, for example from 8 to less than 13 amino acid residues, such as from 8 to less than 12 amino acid residues, for example from 8 to less than 11 amino acid residues, such as from 9 to less than 5000 amino acid residues, for example from 9 to less than 1000 amino acid residues, such as from 9 to less than 900 amino acid residues, for example from 9 to less than 800 amino acid residues, such as from 9 to less than 700 amino acid residues, for example from 9 to less than 600 amino acid residues, such as from 9 to less than 500 amino acid residues, for example from 9 to less than 400 amino acid residues, such as from 9 to less than 300 amino acid residues, for example from 9 to less than 200 amino acid residues, such as from 9 to less than 100', amino acid residues, for example from 9 to less than 90 amino acid residues, such as from 9 to less than 80 amino acid residues, for example from 9 to less than 70 amino acid residues, such as from 9 to less than 60 amino acid residues, for example from 9 to less than 50 amino acid residues, such as from 9 to less than 40 amino acid residues, for example from 9 to less than 35 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 20 amino acid residues, for example from 9 to less than 19 amino acid residues, such as from 9 to less than 18 amino acid residues, for example from 9 to less than 17 amino acid residues, such as from 9 to less than 16 amino acid residues, for example from 9 to less than 15 amino acid residues, such as from 9 to less than 14 amino acid residues, for example from 9 to less than 13 amino acid residues, such as from 9 to less than 12 amino acid residues, for example from 9 to less than 11 amino acid residues, such as from 10 to less than 5000 amino acid residues, for example from 10 to less than 1000 amino acid residues, such as from 10 to less than 900 amino acid residues, for example from 10 to less than 800 amino acid residues, such as from 10 to less than 700 amino acid residues, for example from 10 to less than 600 amino acid residues, such as from 10 to less than 500 amino acid residues, for example from 10 to less than 400 amino acid residues, such as from 10 to less than 300 amino acid residues, for example from 10 to less than 200 amino acid residues, such as from 10 to less than 100 amino acid residues, for example from 10 to less than 90 amino acid residues, such as from 10 to less than 80 amino acid residues, for example from 10 to less than 70 amino acid residues, such as from 10 to less than 60 amino acid residues, for example from 10 to less than 50 amino acid residues, such as from 10 to less than 40 amino acid residues, for example from 10 to less than 35 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 20 amino acid residues, for example from 10 to less than 19 amino acid residues, such as from 10 to less than 18 amino acid residues, for example from 10 to less than 17 amino acid residues, such as from 10 to less than 16 amino acid residues, for example from 10 to less than 15 amino acid residues, such as from 10 to less than 14 amino acid residues, for example from 10 to less than 13 amino acid residues, such as from 10 to less than 12 amino acid residues, such as from 11 to less than 5000 amino acid residues, for example from 11 to less than 1000 amino acid residues, such as from 11 to less than 900 amino acid residues, for example from 11 to less than 800 amino acid residues, such as from 11 to less than 700 amino acid residues, for example from 11 to less than 600 amino acid residues, such as from 11 to less than 500 amino acid residues, for example from 11 to less than 400 amino acid residues, such as from 11 to less than 300 amino acid residues, for example from 11 to less than 200 amino acid residues, such as from 11 to less than 100 amino acid residues, for example from 11 to less than 90 amino acid residues, such as from 11 to less than 80 amino acid residues, for example from 11 to less than 70 amino acid residues, such as from 11 to less than 60 amino acid residues, for example from 11 to less than 50 amino acid residues, such as from 11 to less than 40 amino acid residues, for example from 11 to less than 35 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 20 amino acid residues, for example from 11 to less than 19 amino acid residues, such as from 11 to less than 18 amino acid residues, for example from 11 to less than 17 amino acid residues, such as from 11 to less than 16 amino acid residues, for example from 11 to less than 15 amino acid residues, such as from 11 to less than 14 amino acid residues, for example from 11 to less than 13 amino acid residues, such as from 12 to less than 5000 amino acid residues, for example from 12 to less than 1000 amino acid residues, such as from 12 to less than 900 amino acid residues, for example from 12 to less than 800 amino acid residues, such as from 12 to less than 700 amino acid residues, for example from 12 to less than 600 amino acid residues, such as from 12 to less than 500 amino acid residues, for example from 12 to less than 400 amino acid residues, such as from 12 to less than 300 amino acid residues, for example from 12 to less than 200 amino acid residues, such as from 12 to less than 100 amino acid residues, for example from 12 to less than 90 amino acid residues, such as from 12 to less than 80 amino acid residues, for example from 12 to less than 70 amino acid residues, such as from 12 to less than 60 amino acid residues, for example from 12 to less than 50 amino acid residues, such as from 12 to less than 40 amino acid residues, for example from 12 to less than 35 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 20 amino acid residues, for example from 12 to less than 19 amino acid residues, for example from 12 to less than 18 amino acid residues, for example from 12 to less than 17 amino acid residues, such as from 12 to less than 16 amino acid residues, for example from 12 to less than 15 amino acid residues, such as from 12 to less than 14 amino acid residues, such as from 13 to less than 5000 amino acid residues, for example from 13 to less than 1000 amino acid residues, such as from 13 to less than 900 amino acid residues, for example from 13 to less than 800 amino acid residues, such as from 13 to less than 700 amino acid residues, for example from 13 to less than 600 amino acid residues, such as from 13 to less than 500 amino acid residues, for example from 13 to less than 400 amino acid residues, such as from 13 to less than 300 amino acid residues, for example from 13 to less than 200 amino acid residues, such as from 13 to less than 100 amino acid residues, for example from 13 to less than 90 amino acid residues, such as from 13 to less than 80 amino acid residues, for example from 13 to less than 70 amino acid residues, such as from 13 to less than 60 amino acid residues, for example from 13 to less than 50 amino acid residues, such as from 13 to less than 40 amino acid residues, for example from 13 to less than 35 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 20 amino acid residues, for example from 13 to less than 19 amino acid residues, such as from 13 to less than 18 amino acid residues, for example from 13 to less than 17 amino acid residues, such as from 13 to less than 16 amino acid residues, for example from 13 to less than 15 amino acid residues, such as from 14 to less than 5000 amino acid residues, for example from 14 to less than 1000 amino acid residues, such as from 14 to less than 900 amino acid residues, for example from 14 to less than 800 amino acid residues, such as from 14 to less than 700 amino acid residues, for example from 14 to less than 600 amino acid residues, such as from 14 to less than 500 amino acid residues, for example from 14 to less than 400 amino acid residues, such as from 14 to less than 300 amino acid residues, for example from 14 to less than 200 amino acid residues, such as from 14 to less than 100 amino acid residues, for example from 14 to less than 90 amino acid residues, such as from 14 to less than 80 amino acid residues, for example from 14 to less than 70 amino acid residues, such as from 14 to less than 60 amino acid residues, for example from 14 to less than 50 amino acid residues, such as from 14 to less than 40 amino acid residues, for example from 14 to less than 35 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 20 amino acid residues, for example from 14 to less than 19 amino acid residues, such as from 14 to less than 18 amino acid residues, for example from 14 to less than 17 amino acid residues, such as from 14 to less than 16 amino acid residues, such as from 15 to less than 5000 amino acid residues, for example from 15 to less than 1000 amino acid residues, such as from 15 to less than 900 amino acid residues, for example from 15 to less than 800 amino acid residues, such as from 15 to less than 700 amino acid residues, for example from 15 to less than 600 amino acid residues, such as from 15 to less than 500 amino acid residues, for example from 15 to less than 400 amino acid residues, such as from 15 to less than 300 amino acid residues, for example from 15 to less than 200 amino acid residues, such as from 15 to less than 100 amino acid residues, for example from 15 to less than 90 amino acid residues, such as from 15 to less than 80 amino acid residues, for example from 15 to less than 70 amino acid residues, such as from 15 to less than 60 amino acid residues, for example from 15 to less than 50 amino acid residues, such as from 15 to less than 40 amino acid residues, for example from 15 to less than 35 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 20 amino acid residues, for example from 15 to less than 19 amino acid residues, such as from 15 to less than 18 amino acid residues, for example from 15 to less than 17 amino acid residues, such as from 16 to less than 5000 amino acid residues, for example from 16 to less than 1000 amino acid residues, such as from 16 to less than 900 amino acid residues, for example from 16 to less than 800 amino acid residues, such as from 16 to less than 700 amino acid residues, for example from 16 to less than 600 amino acid residues, such as from 16 to less than 500 amino acid residues, for example from 16 to less than 400 amino acid residues, such as from 16 to less than 300 amino acid residues, for example from 16 to less than 200 amino acid residues, such as from 16 to less than 100 amino acid residues, for example from 16 to less than 90 amino acid residues, such as from 16 to less than 80 amino acid residues, for example from 16 to less than 70 amino acid residues, such as from 16 to less than 60 amino acid residues, for example from 16 to less than 50 amino acid residues, such as from 16 to less than 40 amino acid residues, for example from 16 to less than 35 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 20 amino acid residues, for example from 16 to less than 19 amino acid residues, such as from 16 to less than 18 amino acid residues, such as from 17 to less than 5000 amino acid residues, for example from 17 to less than 1000 amino acid residues, such as from 17 to less than 900 amino acid residues, for example from 17 to less than 800 amino acid residues, such as from 17 to less than 700 amino acid residues, for example from 17 to less than 600 amino acid residues, such as from 17 to less than 500 amino acid residues, for example from 17 to less than 400 amino acid residues, such as from 17 to less than 300 amino acid residues, for example from 17 to less than 200 amino acid residues, such as from 17 to less than 100 amino acid residues, for example from 17 to less than 90 amino acid residues, such as from 17 to less than 80 amino acid residues, for example from 17 to less than 70 amino acid residues, such as from 17 to less than 60 amino acid residues, for example from 17 to less than 50 amino acid residues, such as from 17 to less than 40 amino acid residues, for example from 17 to less than 35 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 20 amino acid residues, for example from 17 to less than 19 amino acid residues, such as from 18 to less than 5000 amino acid residues, for example from 18 to less than 1000 amino acid residues, such as from 18 to less than 900 amino acid residues, for example from 18 to less than 800 amino acid residues, such as from 18 to less than 700 amino acid residues, for example from 18 to less than 600 amino acid residues, such as from 18 to less than 500 amino acid residues, for example from 18 to less than 400 amino acid residues, such as from 18 to less than 300 amino acid residues, for example from 18 to less than 200 amino acid residues, such as from 18 to less than 100 amino acid residues, for example from 18 to less than 90 amino acid residues, such as from 18 to less than 80 amino acid residues, for example from 18 to less than 70 amino acid residues, such as from 18 to less than 60 amino acid residues, for example from 18 to less than 50 amino acid residues, such as from 18 to less than 40 amino acid residues, for example from 18 to less than 35 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 20 amino acid residues, such as from 19 to less than 5000 amino acid residues, for example from 19 to less than 1000 amino acid residues, such as from 19 to less than 900 amino acid residues, for example from 19 to less than 800 amino acid residues, such as from 19 to less than 700 amino acid residues, for example from 19 to less than 600 amino acid residues, such as from 19 to less than 500 amino acid residues, for example from 19 to less than 400 amino acid residues, such as from 19 to less than 300 amino acid residues, for example from 19 to less than 200 amino acid residues, such as from 19 to less than 100 amino acid residues, for example from 19 to less than 90 amino acid residues, such as from 19 to less than 80 amino acid residues, for example from 19 to less than 70 amino acid residues, such as from 19 to less than 60 amino acid residues, for example from 19 to less than 50 amino acid residues, such as from 19 to less than 40 amino acid residues, for example from 19 to less than 35 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues.

Furthermore, the primary and secondary antigens of the present invention may differ in sequence homology. The homology between amino acid sequences may be calculated using well known algorithms such as for example any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90. The differences in sequence between the primary and secondary antigen may comprise substitution of one or more amino acid residues for another from the naturally occurring or unnaturally occurring amino acids. The naturally occurring amino acids of the invention may be synthetically prepared and linked or may be the result of proteolytic cleavage of any type of protein that may be isolated from any type of organism. An aspect of the present invention relates to antigens and/or proteins derived from organisms. These organisms may be any organism, such as pathogenic or non-pathogenic organisms. Especially if pathogenic organisms are used as a source of primary antigens, they may be inactivated or killed prior to use by heat inactivation, autoclaving or any other means known to the art. Naturally occurring peptides may furthermore be mutated by the substitution, addition or deletion of naturally or un-naturally occurring amino acid residues. Especially substitutions may be benign, meaning that an amino acid residue is exchanged for an amino acid residue of the same type such as the original. As an example: The amino acids Asp, Glu, Lys, Arg, His, Asn, Gln, Ser, Thr, Tyr, and Cys all have polar chains and thus exchanging one of these for another would constitute a benign substitution. Examples of various groups of amino acids that are related by the nature of their side chains apart from the above-mentioned are: Amino acids having non-polar side chains (Gly, Ala, Val, Leu, Ile, Phe, Trp, Pro, and Met), amino acids having aliphatic side chains (Gly, Ala Val, Leu, Ile), amino acids having cyclic side chains (Phe, Tyr, Trp, His, Pro), amino acids having aromatic side chains (Phe, Tyr, Trp), amino acids having acidic side chains (Asp, Glu), amino acids having basic side chains (Lys, Arg, His), amino acids having amide side chains (Asn, Gln), amino acids having hydroxy side chains (Ser, Thr), amino acids having sulphur-containing side chains (Cys, Met), neutral, weakly hydrophobic amino acids (Pro, Ala, Gly, Ser, Thr), hydrophilic, acidic amino acids (Gln, Asn, Glu, Asp), and hydrophobic amino acids (Leu, Ile, Val). Differences between primary and secondary antigens may furthermore comprise substitution or substitutions of one or more moieties such as and not limited to any of the above defined groups or from the groups of non-natural or non-standard amino acids. Non-natural amino acids comprise any amino acid not included in table 2 herein above. Non-natural amino acids include, but are not limited to modified amino acids, pseudo-amino acids, L-amino acids, and stereoisomers of D-amino acids. Non-standard amino acids are amino acids capable of being incorporated into a peptide or peptide like structure by translation mediated by a ribosome that, according to the present invention, is any amino acid comprising an amino group and a carboxyl group separated by an α-carbon. The amino acid may for example be selected from the group consisting of, Aib, Nal, Sar, Orn, Lysine analogues DAP and DAPA or any of the amino acids described in U.S. Pat. No. 5,573,905. Furthermore, non-standard amino acids may be any of the above mentioned or any standard amino acids which further comprises one or more moieties selected from the group consisting of hydroxyl, bromo, fluoro, chloro, iodo, mercapto, thio, cyano, aikylthio, heterocycle, aryl, heteroaryl, carboxyl, carboalkoyl, alkyl, alkenyl, nitro, amino, alkoxyl and/or amido. The non-standard amino acid is capable of being incorporated into a peptide or peptide like structure by translation mediated by a wt, mutant, modified or recombinant ribosome.

In yet another embodiment of the present invention the primary and secondary antigens may differ in sequence such as substituting one or more amino acids for one or more amino acids respectively, substituting and substituted amino acids differing in e.g. hydrophilic or hydropathic indices that are within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted. The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference). The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982). The amino acid hydrophilicity values are: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5) histidine (−0.5); cysteine (−1.0);

methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In another embodiment of the present invention the primary and secondary antigens may differ in secondary structure comprising for example length and arrangement of alpha-helices, $3_{10}$-helices, π-helices, beta-strands, beta-sheets, beta-hairpins loops, N-terminal and C-terminal stretches of amino acids and loops connecting said secondary structure elements. Furthermore the primary and secondary antigens may differ in fold and tertiary and quaternary structural arrangement of primary and secondary structural elements.

In another embodiment of the present invention the moieties of the primary and secondary antigens differ in post translational modifications. The said modifications occur after the translation of the mRNA into protein within a cell. All of the mentioned modifications may be performed synthetically on any of the moieties of the invention. The modifications of the present invention include but are not limited to modifications involving the addition of functional group such as: acetylation (the addition of an acetyl group, usually at the N-terminus of the protein), alkylation (the addition of an alkyl group (e.g. methyl, ethyl), especially methylation (the addition of a methyl group, usually at lysine or arginine residues), biotinylation (acylation of conserved lysine residues with a biotin appendage), glutamylation (covalent linkage of glutamic acid residues to tubulin and some other proteins), glycylation (covalent linkage of one to more than 40 glycine residues to the tubulin C-terminal tail), glycosylation (the addition of a glycosyl group typically to either asparagine, hydroxylysine, serine, or threonine, resulting in a glycoprotein) isoprenylation (the addition of an isoprenoid group e.g. farnesol and geranylgeraniol), lipoylation (attachment of a lipoate functionality), phosphopantetheinylation (the addition of a 4'-phosphopantetheinyl moiety from coenzyme A, as in fatty acid, polyketide, non-ribosomal peptide and leucine biosynthesis), phosphorylation (the addition of a phosphate group to any residue, but typically to serine, tyrosine, threonine or histidine), sulfation (the addition of a sulfate group to a tyrosine), selenation and C-terminal amidation. Preferably, the moieties of the present invention are modified by phosphorylation, sulfation, glycosylation, methylation, amino acid conjugation, glutathione conjugation and/or acetylation. Any moiety may thus be modified at least once with any of the above mentioned modifications. And any peptide or peptide-like compound may comprise none, 1, 2, 3, 4, 5, 6, 7, 8, 9, 10, 11, 15, 20 or more modifications or any number herein between or above. Other modifications may be the addition of other proteins or peptides such as ISGylation (the covalent linkage to the ISG15 protein (Interferon-Stimulated Gene 15)), SUMOylation (the covalent linkage to the SUMO protein (Small Ubiquitin-related MOdifier)), ubiquitination (the covalent linkage to the protein ubiquitin), or may involve a change of the chemical nature of amino acids, such as citrullination/deimination (the conversion of arginine to citrulline), deamidation (the conversion of glutamine to glutamic acid or asparagine to aspartic acid) or modifications may involve structural changes such as disulfide bridges (the covalent linkage of two cysteine amino acids), proteolytic cleavage (cleavage of a protein at a peptide bond). Preferably, the moieties of the present invention are modified by ubiquitination, deamidation or the formation of disulfide bridges. These modifications may be singularly appearing or repeatedly appearing together with any of the above mentioned modifications.

By peptide is meant any plurality of individual moieties as are comprised in the above definition, occasionally these will be referred to as peptide-like compounds in the present text. Thus any type of bond may link the individual moieties of above, not only peptide bonds. Examples of bonds linking moieties of the present invention are: peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds and imide bonds. Any of the bonds of the above may be used as the only type of bond within the peptide, or two or more such as three or more different types of bonds may be comprised within a peptide-like compound. Preferably, the bonds connecting the moieties of the invention are peptide bonds, imine bonds and imide bonds, and most preferably peptide bonds.

In yet another embodiment of the present invention the primary and secondary antigen may differ in domain composition such as comprising an α-peptide domain, a β-peptide domain, a γ-peptide domain, an ω-peptide domain, a mono-, di- and tri-substituted α-peptide domain, a mono-, di- and tri-substituted β-peptide domain, a mono-, di- and tri-substituted γ-peptide domain, a mono-, di- and tri-substituted ω-peptide domain, a peptide domain wherein the amino acid residues are in the L-form, a peptide domain wherein the amino acid residues are in the D-form, a peptide domain wherein the amino acid residues are both in the L-form and in the D-form, a vinylogous peptide domain, a glyco-peptide domain, a vinylogous sulfonamide peptide domain, a polysulfonamide domain, a conjugated peptide domain and a conjugated peptide domain comprising one or more functional group(s), such as one or more prosthetic group(s).

In yet another embodiment of the present invention said antigens may differ in peptide linkage by specific linkers forming di-, tri-, tetra-, penta-, hexa-, hepta-, octa-, nona- or deca-polypeptides or larger peptide polymers.

In a further embodiment of the present invention said primary and secondary antigens may differ in their adjuvants and/or their carrier(s). Adjuvants are also known as pharmaceutical carriers, or functional equivalents hereof and may be included in the immunization solution containing the primary antigens in order to enhance the specific immune response. Thus, it is particularly important to identify an adjuvant that when combined with the primary antigen results in an immunization composition capable of inducing a strong specific immunological response. Functionally equivalent carriers are capable of presenting the same immunogenic determinant in essentially the same steric conformation when used under similar conditions. Functionally equivalent adjuvants are capable of providing similar increases in the efficacy of the composition when used under similar conditions. Preferably, the immunogenic compositions of the present invention comprise potent, nontoxic adjuvants that will enhance and/or modulate the immunogenicity of immunogenic determinants including antigenic determinants including haptenic determinants represent one group of preferred adjuvants. In addition, such adjuvants preferably also elicit an earlier, more potent, or more prolonged immune response. An embodiment of the present invention relates to an immunization composition comprising an adjuvant. In a preferred embodiment the vaccine composition is suitable for administration to an avian subject, thus a preferred adjuvant is suitable for administration to a chicken or hen as defined in the above. Adjuvants pertaining to the present invention may be grouped according to their origin, be it mineral, bacterial, plant, synthetic, or host product. The first group under this classification is the mineral adjuvants, such as aluminium compounds. Antigens precipitated with aluminium salts or antigens mixed with or adsorbed to performed aluminium compounds have been used extensively to augment immune responses in animals and humans. Aluminium particles have been demonstrated in regional lymph nodes of rabbits seven days following immunization, and it may be that another significant function is to direct antigen to T cell containing areas in the nodes themselves. Adjuvant potency has been shown to correlate with intimation of the draining lymph nodes. While many studies have confirmed that antigens administered with aluminium salts lead to increased humoral immunity, cell mediated immunity appears to be only slightly increased, as measured by delayed-type hypersensitivity. Aluminium hydroxide has also been described as activating the complement pathway. This mechanism may play a role in the local inflammatory response as well as immunoglobulin production and B cell memory. Furthermore, aluminium hydroxide can protect the antigen from rapid catabolism. Primarily because of their excellent record of safety, aluminium compounds are presently the only adjuvants used in humans.

Another large and important group of adjuvants that may be used in conjunction with primary or secondary antigens of the present invention are that of bacterial origin. Adjuvants with bacterial origins can be purified and synthesized (e.g. muramyl dipeptides, lipid A) and host mediators have been cloned (Interleukin 1 and 2). The last decade has brought significant progress in the chemical purification of several adjuvants of active components of bacterial origin: *Bordetella pertussis, Mycobacterium tuberculosis*, lipopoly-saccharide, Freund's Complete Adjuvant (FCA) and Freund's Incomplete Adjuvant (Difco Laboratories, Detroit, Mich.) and Merck Adjuvant 65 (Merck and Company, Inc., Rahway, N.J.). Additionally suitable adjuvants in accordance with the present invention are e.g. Titermax Classical adjuvant (SIGMA-ALDRICH), ISCOMS, Quil A, ALUN, see U.S. Pat. No. 58,767 and U.S. Pat. No. 5,554,372, Lipid A derivatives, choleratoxin derivatives, HSP derivatives, LPS derivatives, synthetic peptide matrixes, GMDP, and other as well as combined with immunostimulants (U.S. Pat. No. 5,876,735).

*B. pertussis* is of interest as an adjuvant in the context of the present invention due to its ability to modulate cell-mediated immunity through action on T-lymphocyte populations. For lipopolysaccharide and Freund's Complete Adjuvant, adjuvant active moieties have been identified and synthesized which permit study of structure-function relationships. These are also considered for inclusion in immunogenic compositions according to the present invention. Lipopolysaccharide and its various derivatives, including lipid A, have been found to be powerful adjuvants in combination with liposomes or other lipid emulsions. It is not yet certain whether derivatives with sufficiently low toxicity for general use in humans can be produced. Freund's Complete Adjuvant is the standard in most experimental studies.

Mineral oil may be added to the immunogenic composition in order to protect the antigen from rapid catabolism. Many other types of materials can be used as adjuvants in immunogenic compositions according to the present invention. They include plant products such as saponin, animal products such as chitin and numerous synthetic chemicals. Adjuvants according to the present invention can also been categorized by their proposed mechanisms of action. This type of classification is necessarily somewhat arbitrary because most adjuvants appear to function by more than one mechanism. Adjuvants may act through antigen localization and delivery, or by direct effects on cells making up the immune system, such as macrophages and lymphocytes. Another mechanism by which adjuvants according to the invention enhance the immune response is by creation of an antigen depot. This appears to contribute to the adjuvant activity of aluminium compounds, oil emulsions, liposomes, and synthetic polymers. The adjuvant activity of lipopolysaccharides and muramyl dipeptides appears to be mainly mediated through activation of the macrophage, whereas *B. pertussis* affects both macrophages and lymphocytes. Further examples of adjuvants that may be useful when incorporated into immunogenic compositions according to the present invention are described in U.S. Pat. No. 5,554,372. Useful adjuvants useful may thus be mineral salts, such as aluminium hydroxide and aluminium or calcium phosphates gels, oil emulsions and surfactant based formulations such as MF59 (microfluidised detergent stabilised oil in water emulsion), QS21 (purified saponin), AS02 (SBAS2, oil-in-water emulsion+monophosphoryl lipid A (MPL)+QS21), Montanide ISA 51 and ISA-720 (stabilised water in oil emulsion), Adjuvant 65 (containing peanut oil, mannide monooleate and aluminium monostearate), RIBI ImmunoChem Research Inc., Hamilton, Utah), particulate adjuvants, such as virosomes (unilamellar liposomal vesicles incorporating influenza haemagglutinin), AS04 (Al salt with MPL), ISCOMS (structured complex of saponins and lipids (such as cholesterol), polyactide co-glycolide (PLG), microbial derivatives (natural and synthetic) such as monophosphoryl lipid A (MPL), Detox (MPL+*M. Phlei* cell wall skeleton), AGP (RC-529 (synthetic acylated monosaccharide)), DC_chol (lipoidal immunostimulators able to self organise into liposomes), OM-174 (lipid A derivative), CpG motifs (synthetic oligonucleotides containing immunostimulatory CpG motifs), modified bacterial toxins, LT and CT, with non-toxic adjuvant effects, Endogenous human immunomodulators, e.g., hGM-CSF or hIL-12 or Immudaptin (C3d tandem array), inert vehicles such as gold particles. Additional examples of adjuvants comprise: Immunostimulatory oil emulsions (for example, water-in-oil, oil-in-water, water-in-oil-in-water such as e.g. Freund's incomplete adjuvant such as Montainde®, Specol, mineral salts such e.g. as $Al(OH)_3$, $AlPO_4$, microbial products, Saponins such as Qual A, synthetic products, as well as adjuvant formulations, and immune stimulatory complexes (ISCOMs) and cytokines, heat-inactivated bacteria/components, nanobeads, LPS, LTA. A list of other commonly used adjuvants is disclosed on pages 6-8 in WO 03089471, the list being hereby incorporated by reference. Immunogenic compositions according to the invention may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are exemplary appropriate diluents. Preferably, the compositions are formulated as a lyophilisate using appropriate excipient solutions (e.g., sucrose) as diluents. The immunogenic compositions of the present invention may furthermore comprise pharmaceutical carriers. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Immunization of the animal may be carried out with adjuvants and/or pharmaceutical carriers. An adjuvant is any substance that enhances the immune response to an antigen with which it is mixed. The antigen may also be mixed with two or more different adjuvants prior to immunization. Adjuvants are generally included in the immunogenic compositions in an amount according to the instructions of the manufacturer. If the adjuvant is Specol an amount of e.g. 1:1 compared to the antigen/carrier mixture or antigen mixture alone may be added to the immunogenic composition. Preferably, the adjuvants of the present invention are Freunds complete adjuvant, Freunds incomplete adjuvant, Specol, Titermax Gold, Alhydrogel, Gerbu Adjuvant 100, Diluvac Forte and Super Adjuvant as defined in the Examples. More preferably, the adjuvants are Freunds complete adjuvant, Freunds incomplete adjuvant, Specol, Titermax Gold, and Super Adjuvant. With these preferred adjuvants, antibodies may be harvested after only about two weeks, instead after three to six weeks. The primary and the secondary antigens of the present invention may differ in one or more of the abovementioned adjuvant compositions.

A further embodiment of the present invention is the option of a difference in carrier of the primary and secondary antigens. Conjugation to a carrier is important because the primary and secondary antigens, peptides and peptide-like compounds may be small molecules and small molecules alone do not tend to be immunogenic, thus possibly eliciting a weak immune response. Hence a carrier would be of great benefit in especially the primary antigen formulations. A carrier typically contains many epitopes that stimulate T-helper cells, which help induce the B-cell response. The carrier may be present independently of an adjuvant (please see in the below). The purpose of conjugation and/or co-immunization of an antigen/immunogenic determinant and a carrier can be e.g. to increase the molecular weight of the antigen in order to increase the activity or immunogenicity of the determinant, to confer stability to the determinant, to increase the biological activity of the determinant, or to increase its serum half-life. The carrier protein may be any conventional carrier including any protein suitable for presenting immunogenic determinants. Conventional carrier proteins include, but are not limited to, keyhole limpet hemocyanin, serum proteins such as transferrin, bovine serum albumin, or human serum albumin, an ovalbumin, immunoglobulins, or hormones, such as insulin. While any suitable pharmaceutical carrier known to those of ordinary skill in the art may be employed in the immunogenic and pharmaceutical compositions of this invention, the type of pharmaceutical carrier will vary depending on the mode of administration and whether a sustained release administration is desired. For parenteral administration, such as subcutaneous injection, the pharmaceutical carrier may e.g. comprise water, saline, alcohol, fat, a wax or a buffer. For oral administration, any of the above pharmaceutical carriers or a solid pharmaceutical carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as pharmaceutical carriers for the pharmaceutical compositions of this invention. Suitable biodegradable microspheres are disclosed, for example, in U.S. Pat. No. 4,897,268 and U.S. Pat. No. 5,075,109.

The primary antigen may be encapsulated within the biodegradable microsphere or associated with the surface of the microsphere. Primary antigens within the scope of the present invention could be conjugated by any method known to the person skilled in the art. For example they could be conjugated by a physical association generated by for example the formation of a chemical bond, such as for example a covalent bond, formed between compounds to be conjugated. Compounds could be conjugated for example by an oxidative induced cross-link, such as mild oxidative induced cross-link catalyzed by long-time expo-sure to atmospheric air, such as an over-night exposure. Alternatively, compounds could be conjugated using a chemical cross-linking reagent. Examples of chemical cross-linking reagents are glutaraldehyde, charbodiimid or formaldehyde. The present invention provides embodiments comprising primary and secondary antigens which both may be non-conjugated, an immunogenic composition wherein said antigen is conjugated and an immunogenic composition wherein said antigens are a mixture of are non-conjugated and conjugated antigens. Many different carriers can be used for coupling to antigens, especially to synthetic peptides. The most commonly utilised carriers here fore are keyhole limpet hemacyanin (KLH) and bovine serum albumin (BSA). The higher immunogenicity of KLH often makes it the preferred choice. Another advantage of choosing KLH over BSA is that BSA is used as a blocking agent in many experimental assays. Because antisera raised against peptides conjugated to BSA will also contain antibodies to BSA, false positives may result. Although KLH is large and immunogenic, it may precipitate during cross-linking, making it difficult to handle in some cases. Ovalbumin (OVA) is another useful carrier protein. It is a good choice as a second carrier protein when verifying whether antibodies are specific for the peptide alone and not the carrier. Rabbit Serum Albumin (RSA) may be used when the antibody response to the carrier protein must be kept to a minimum. Rabbits immunized with RSA conjugate are less likely to raise antibodies to the carrier, as the RSA is recognized as "self." If the RSA conjugate were injected into another host, the protein would not be recognized as self. The same principle, of course, applies when immunizing with chicken-derived carriers in chicken. An example of a chicken derived carrier is CSA (Chicken Serum Albumin). By using CSA (Chicken Serum Albumin) or beads an immune response against the carrier may be avoided, thereby optimising the productivity of the chicken immune response. It is important to recognise that the immune system reacts to the peptide-protein carrier as a whole and that there will be a portion of response directed against the conjugated peptide as well as the linker and the carrier. When screening by ELISA it is advisable to use a peptide conjugate prepared using a different carrier. This is not necessary if performing ELISA assays where the plates are coated directly with unconjugated peptide. Thus examples of carriers include, but are not limited to BSA, CSA, SA, KLH, Beads or other carrier-systems. Suitable carriers will be of protein origin in most cases. In some cases however, the carrier may be of non-protein origin such as e.g. polymers comprising carbohydrates, etc. Preferably either CSA or beads are used to avoid immune response against the carrier. The coupling can be made by glutaraldehyde, MBS or other coupling methods. Glutaraldehyde couples between free amino groups ($-NH_2$) and cysteine. The ratio between peptide and carrier has to be exact to avoid over-coupling. By decreasing the pH to a value lower than the pK value of the amino acids coupling to the side chains is avoided. Correction has to be made for sequences containing cysteine. It may not be necessary to conjugate relatively large primary antigen peptides with a carrier in order to obtain an immune response. Primary antigens of peptidic nature with a length of at least 50 moieties/amino acids and more, preferably with a length of at least 100 moieties or at least 150 moieties may not need carrier conjugation in order to function as immunogens in the present invention. It is however advisable to conjugate all primary antigens with carrier molecules disregard the size of the primary antigen(s).

The Method of Harvesting Antibodies from an Antibody Library

The secondary antigen against which one desires an antibody (i.e. with binding specificity towards) is isolated or in the case of peptide based secondary antigens synthesised in e.g. an *E. coli* or cell free expression system. Synthesised antigenic peptide is purified by subsequent steps of e.g. affinity chromatography, ion exchange chromatography and reversed phase HPLC. Pure secondary antigen peptide is covalently coupled either to as carrier as described herein above or to e.g. a CNBr-sepharose resin that subsequently can be transferred into a column of appropriate volume. The library of antibodies constructed as described is passed through the column whereupon the resin-coupled homogenous antigen population and the antibody-containing library solution interact.

The method described can also be performed in batch where after the resin is separated and removed from the library solution by centrifugation.

The non-covalently bound antibodies in the column or batch preparation are subsequently eluted using a gradient of decreasing values of pH or increasing concentrations of salt. Hence, antibodies of first low, subsequently medium and finally high affinity will be eluted from the column and eluted and collected in order of affinity. The concentration of the eluting antibodies is monitored using a UV detector operating at a wavelength of 280 nm. The desired antibody, it being of high, medium or low affinity according to ones needs, is now available as an isolated product. In order to dissociate antibodies with extreme affinities to an antigen, antibody-bound beads may (after or before pH/salt elution) be transferred to a flow chamber where sound pulses (sonication) will release the most tightly bound antibodies from the antigens. The flowthrough is dialysed against a physiological buffer. Any covalently coupled antigen-resin slurry can be regenerated and reused.

In an alternative embodiment, the secondary antigen, against which a specific antibody is desired, is synthesized and coupled to a polystyrene coated aluminium rod subsequent to epoxy coating of said rod which is immersed into a buffer solution whereafter the secondary antigen is added to said buffer solution. An interaction between the antigen(s) and antibodies will take place. The antigen is covalently bound to the pole, and to the antibody by non-covalent bonds such as hydrogen bonds, van der Waals bonds, ionic bonds, dipole-dipol and hydrophobic interactions, wherefore the bond between the antigen and antibody is broken first. The vessel containing the secondary antigen and the coated rod is centrifuged in a suited tube whereafter the rod is washed to facilitate supernatant removal. The secondary antigen-coated rod can subsequently be used for antibody harvesting. This procedure is performed in such a way that the rod is immersed into antibody library containing tank and incubated. Upon use of bacterial or virus secondary antigens the rod is preferably covered with a porous membrane to prevent debris-contamination of the antibody tank, yet allowing antibodies to pass. The rod is removed from the tank subsequent to incubation and unspecifically bound antibodies are washed away. Weakly bound antibodies are dissociated from their corresponding antigen by immersing the rod in a weakly acidic solution. This step is repeated with solutions of gradually lower pH until all antibodies have dissociated from the rod. By using different dissociation or elution conditions, This procedure renders specific antibody aliquots of distinct affinities that allows an approximate quantification of the binding affinity of the antibody for its binding partner. Elution agents that may be used include chaotropic agents such as guanidine hydrochloride or urea at concentrations between 10 µM and 8 M or ethylene glycol in an aqueous solution of 0.01% to 100% w/v. Elutions may also be carried out using aqueous or non-aqueous solutions of glycine. Elutions may be carried out using aqueous or non aqueous solutions of triethylamine between 1 µM and a saturated solution, preferably 100 mM, at a pH of between pH 8 and pH 13, preferably pH 11.5.

Wash buffer aliquots are pooled and dialysed for reuse in the antibody library that can be reused as a source of specific antibodies repeatedly, in theory an indefinite number of times. It follows, that it is much faster to isolate antigen specific antibodies from an antibody library which in theory comprises antibodies that have antibody binding capability to virtually any antigen—rather than immunizing the animal and waiting weeks to months for a specific antibody response. Thus the present invention provides a method of obtaining specific polyclonal and/or monoclonal antibodies in a much faster and significantly less expensive way than is currently employed.

Storage and Shipping of Antibody Libraries and Harvested Antibodies

Ideally, the antibodies are pooled and stored until a time where it is desired to isolate antigen specific antibodies. Antibodies can be stored at subzero degrees (e.g. liquid nitrogen, −70° C., or −20° C.). However, if the library is used for frequent isolation of antigen specific antibodies, it may be preferable to avoid freezing by storing the library at temperatures of about 0, 1, 2, 3, 4, 5, 6, 7, 8, 9, or 10° C. Even though antibodies tend to be stable, repeated freeze/thaw circles may result in some degree of protein denaturation of the antibodies.

Antibodies according to the invention may furthermore be stored in the presence of one or more additives such as: antibiotics, anti-fungal compounds, antifreeze (e.g. glycerol), and buffer solutions. A preferred additive is $NaN_3$— preferably 0.1% $NaN_3$ in PBS. Antibodies may even be stored at room temperature, preferably in the presence of preservatives, for relatively short period of times such as e.g. two weeks or less, preferably one week or less. This might be convenient e.g. in case of transport of antibodies via shipping, mailing, etc.

In a preferred embodiment, antibodies are collected from the animal after a period of at least 14 days, since this period of time is usually required to induce a detectable immune response in e.g. a chicken subsequent to immunization.

The present invention furthermore relates to antibodies obtainable by the methods herein.

Additional Embodiments

Another central aspect of the present invention relates to the use of antibody libraries being specific to a multitude of antigens. In particular, the present invention thus relates to a method of isolating antigen specific antibodies, wherein the method comprises the following steps:
  immobilizing the antigen,
  contacting the antibody library with the immobilized antigen under conditions suitable for an antigen:antibody binding to take place,
  removing unbound antibody, and
  recovering antigen specific antibodies.

An antibody library obtained after immunizing an animal with a peptide library generated by random synthesis thus provides a unique possibility of isolating antibodies with specificity to an antigen within a very short period of time—in theory within few hours.

Various methods of immobilizing the antigen can be employed in connection with isolation of antigen specific antibodies. A preferred solid phase is CNBr carrier. A preferred coupling is Epoxy coupling, since this approach is relatively cheap. Ultrasound sonication or acidic conditions may e.g. be used for breaking the antigen:antibody binding in order to recover antigen specific antibodies. In general, various methods of coupling proteins to a carrier and subsequently breaking protein:protein interactions are well known in the art.

Finally, the present invention relates to antibodies obtainable by the methods herein.

The bonds between antigens and antibodies are dependent on hydrogen bonds, hydrophobic interactions, electrostatic forces and van der Waals forces with dissociation constants extending from $10^{-5}$ M to more than $10^{-12}$ M. Dissociation constants are affected by temperature, pH and solvent. Apart from an affinity of an antibody for a ligand, the overall stability of an antibody-ligand complex is also determined by the valency of the antigen and antibody and the structural arrangement of the interacting parts.

Monoclonal antibodies can be raised by fusion of B lymphocytes with immortal cell cultures to produce hybridomas. Hybridomas will produce many copies of the exact same antibody—an essential feature in the development of antibodies for diagnostic applications. As monoclonal antibodies react with one epitope on the antigen, they are more vulnerable to the loss of epitope through chemical treatment of the antigen than are polyclonal antibodies. This can be offset by pooling two or more monoclonal antibodies to the same antigen.

The specificity of monoclonal antibodies makes them extremely efficient for binding of antigen within a mixture of related molecules, such as in the case of affinity purification. Also, as compared to polyclonal antibodies, the homogeneity of monoclonal antibodies is very high. Accordingly, if experimental conditions are kept constant, results from monoclonal antibodies will be highly reproducible.

Use of Antibodies

It is an aspect of the present invention to use the antibodies harvested from said antibody library using the methods of the present invention. Antibodies can be used to target all diseases caused by bacteria, viruses, parasites, chemicals or other agents which crosses the gastrointestinal tract of an individual, such as a human or animal species. The bacteria are hindered in proliferation and the severity and course of the disease is decrease by the antibodies.

In an embodiment of the present invention the harvested antibodies are utilised in the treatment of gasterointestinal disorders and diseases causing diarrhoea in domestic pigs (*Sus scrofa domesticus*). Targets for said antibodies include but are not limited to *Clostridia, Cocciciosis, Colibacillosis* (*E. Coli*), PED, PRRS, Rotavirus and TGE.

In another embodiment of the present invention said antibodies are utilised to treat widespread agents causing diarrhoea in humans such as *Campylobacter jejuni, Salmonella, Shigella* and *E. Coli.*

In yet another embodiment chicken egg yolk antibodies of the present invention can be used as therapeutics for preventing and treating a variety of enteric diseases by targeting for example Human Rotavirus (HRV), the major causative agent of severe diarrhoea worldwide. In developing countries, rotavirus infection may cause up to one million deaths each year, accounting for an estimated 20-25% of all deaths due to diarrhoea and 6% of all deaths among children less than five years old. Another common target of the present invention is the enterotoxigenic *Escherichia coli*, which especially is seen in children in developing countries and in travelers to these countries. The type of *E. coli* to target varies from area to area and from country to country. Another group to target is the Human Caliciviruses (HCV). The most frequent source of infection appears to be contaminated food/beverages, which may cause up to 90% of food-related gastroenteritis outbreaks. Others to be mentioned are: the dysentery causing bacteria from the Shigella family, which spreads through contaminated fod and water when either is swallowed; the bacterium *Vibrio Cholerae* causing cholera. This agent is rare in Western countries but more common in travelers and related to contaminated water; *Campylobacter, Salmonella* spp.; *Staphylococcus aureus; Pseudomonas aeruginosa*; and the protozoans *Cryptosporidium* and *Giardia lamblia.*

Another application for the present invention is prophylaxis or treatment of gastrointestinal disorders in animals including Rotaviruses in domestic animals including but not limited to pigs, calves, lambs/sheep, dogaand cats. Coronaviruses causing diarrhoea in domestic animals is also a target object of the present invention including but not limited to Transmissible Gastro Enteritis (TGE) and Porcine Epidemic Diarrhoea Virus (PEDV) in pigs, the neonatal calf diarrhoea coronavirus (NCDCV), Bovine coronavirus (BCV), canine coronaviruses (CCoV), feline coronaviruses, Enterotoxigenic *E. coli* (ETEC), Parvovirus, *Cryptosporidium, Giardia, Salmonella* and *Campylobacter.*

In yet another embodiment of the present invention IgY antibodies are used as an additive to mouth rinse or toothpaste to prevent and control plaque and the subsequent oral health problems associated with plaque accumulation. This includes antibodies against *Streptococcus mutans* serotype c, which seems to be the principal causative bacterium of dental caries in human. IgY antibodies in mouth rinse can also be used in the treatment of patients with cystic fibrosis (CF). CF patients have abnormally thick mucus in the lungs, which leads to respiratory infections, which are the major causes of morbidity and mortality in these patients. The most common causes for infection in the lungs of the CF patient are *Staphylococcus aureus, Haemophilus influenzae* and *Pseudomonas aeruginosa* (PA).

It is an object of the present invention to use IgY antibodies as an additive to nasal spray to prevent or treat upper respiratory infections.

Yet another application area of the present invention is to utilise specific IgY molecules in the immobilisation of any possible antigen including and not limited to chemicals, toxins, organic poisons and polluting agents.

In a further embodiment of the present invention said antibodies are coupled to coal-filters for use in the treatment of waste water or gas purification. Likewise the antibodies could be used in sensors for detection of chemicals including and not limited to testing of water supplies, testing of chemicals and polluting agents in seawater and lakes, detection of explosive and drug testing.

In a further embodiment of the present technique of harvesting specific antibodies said antibodies be used to target objects such as but not limited to cancer tumours, human immunodeficiency virus and rhino (common cold) virus.

EXAMPLES

Example 1

Synthesis of Peptide Libraries

A library of peptides with a length of 6 amino acids and of 15 amino acids was synthesized using standard methods. The 20 most commonly occurring (excl. selenocysteine and pyrrolysine) natural amino acids were employed in each reaction and the library thus synthesized at least in theory comprises $20^6$ or $20^{15}$, respectively, different peptides.

Example 2

Antigen Coupling

Method 1:

Peptides to be used as antigens are coupled to a carrier. In this method the peptide sequence must contain at least one cysteine residue or an amino group in order for the cross linking agent (MBS) to efficiently couple the peptides to the carrier protein Keyhole Limpet Hemocyanin (KLH). In this example, a cysteine residue was added to the peptides as the seventh residue before carrier conjugation.

Sephadex G-25 fine beads were swelled overnight in 5 ml buffer (0.1 M $NaH_2PO_4$ pH 6.0) per gram of dry beads at room temperature. The swelled resin was washed 4 times using 0.1 M NaH2PO4 pH 6.0 and poured into a 130×20 mm column. The column was subsequently equilibrated with 15 ml of 0.1 M NaH2PO4 pH 6.0 and the resin was allowed to settle.

4 mg KLH was dissolved in 0.3 ml of 0.1 M NaH2PO4 pH 6.0. 1 mg m-Maleimidobenzoyl-N-Hydroxysuccinimide ester (MBS) in 150 µl of Dimethylformamide (DMF) was added drop-wise to the KLH solution under stirring. The KLH/DMF mixture was incubated at room temperature for 30 min on a rotating mixer.

1 ml of 0.1 M NaH2PO4 pH 6.0 was added to the KLH-MBS conjugate followed by thorough mixing. The mixture was subsequently loaded onto the Sephadex G-25 column. 0.1 M NaH2PO4 pH 6.0 was used as column buffer.

1 ml fractions were collected by gravity flow in 1.5 ml tubes. The fractions comprising the KLH-MBS conjugate (monitored at 280 nm) were pooled in a 15 ml conical tube.

200 µl of Dimethylformamide (DMF), 1 ml of peak fractions at 280 nm pH 6.0, and 5 mg of the cysteine-containing peptide were mixed.

The peptide solution was mixed with the KLH-MBS conjugate and incubated for 12 to 16 hr at room temperature on a rotating mixing wheel.

The KLH-MBS-peptide conjugate was dialyzed for 24 hr at 4° C. against 1 liter of PBS including two changes of buffer. Molecular weight cut off of the dialysis tube was 3,500.

Method 2:

By using Chicken Serum Albumin (CSA) or beads for coupling of the antigens an immune response against the carrier is avoided, thereby optimizing the productivity of the chicken immune response. The coupling between the peptides and the carrier is Mediated by glutaraldehyde, which couples free amino groups (—NH2) and cysteines. The ratio between peptide and carrier has to be exact to avoid overcoupling. By decreasing the pH to a value lower than the pK value of the amino acid residues, coupling to the side chains of the amino acid residues is avoided. Corrections in this calculation have to be made for sequences containing cysteine.

1. 1.5 mg/ml of peptide in PBS (Phosphate Buffered Saline).
2. CSA carrier protein is added in the ratio of 1-2 mol of peptide per 50 amino acids in the carrier. Mix by magnetic stirring under ventilated conditions.
3. While stirring add 0.2% glutaraldehyde in PBS, at a ratio of 1 ml glutaraldehyde/PBS per 20 µmol peptide/protein solution.
4. Incubate 1 hour at room temperature.
5. Add 1 M glycerine in PBS, pH 7.2, to a final concentration of 200 mM. Stir for 1 hour.
6. Separate the peptide-carrier from unbound peptide by dialysis against PBS. 4 changes of buffer each 2 hours.

Example 3

Immunization

Method 1:

20 and 35 weeks old fowls of the "white Italian" race were immunized on day 0, 10, 20, 100 and 200. Blood samples and eggs were taken on day 0, 7, 14, 21, 28, 35, 42, 49 and antibody concentration (IgY) was measured using ELISA techniques (se in the below).

The composition used for each immunization was: 10 µg KLH-peptide dissolved in 0.01 M NaCl buffer (pH 7.2) to a volume of 500 µl and 500 µl Specol to a total volume of 1 ml.

Method 2:

The chickens are immunized in the breast musculature with a pistol. The animals are immunized at day 1, 10 and subsequently every $4^{th}$ week. For each immunization one of the following compositions is used:
1. a minimum of 0.5 mg peptide-carrier mixed in the ratio of 1:1 to Freund's Incomplete Adjuvant diluted in PBS to 200 µl.
2. a minimum of 0.5 mg peptide-carrier mixed in the ratio of 1:1 to Super Adjuvant diluted in PBS to 200 µl (for the composition of the Super Adjuvant, please see in the below).

Example 4

Testing of Super Adjuvant

Components of the Adjuvant:
1. Specol: marcol 52®, Span 85®, Tween 85® (tested with positive results)
2. Vitamin E
3. $Al(OH)_3$
4. Heat Shock Proteins
5. CpG-peptides
6. Heat-inactivated B. Pertussis
7. dsRNA Experimental Design 7 groups of 4 chickens are immunized with the following Adjuvant components:

| 1 | 2 | 3 | 4 | 5 | 6 | 7 |
|---|---|---|---|---|---|---|
| Antigen Specol | Antigen Specol E-vitamin | Antigen Specol E-vitamin Al(OH)3 | Antigen Specol E-vitamin Al(OH)3 HSP | Antigen Specol E-vitamin Al(OH)3 HSP | Antigen Specol E-vitamin Al(OH)3 HSP | Antigen Specol E-vitamin Al(OH)3 HSP |

-continued

| 1 | 2 | 3 | 4 | 5 | 6 | 7 |
|---|---|---|---|---|---|---|
|   |   |   |   | CpG | CpG<br>B. Pertussis | CpG<br>B. Pertussis<br>Synthetic pI:C |

Reagents:
1. PBS
2. Specol:
    1. 8.1 ml Span 85® is mixed with 6.1 ml Tween 85®
    2. 99 ml marcol 52® is mixed with 11 ml Span85®/Tween85®
3. Al(OH)$_3$: 8 mg/ml Al(OH)$_3$ solution is made (5-10 ml)
    1. Couple peptide to Al(OH)$_3$: 440 µg peptide in 2.2 ml PBS is added 2.2 ml (17.6 mg) 8 mg/ml Al(OH)$_3$.
    2. Mix for 30 min. at 20° C.
4. HSP70 (Heat Shock Protein):
    1. Coupling of peptide to HSP70:
        Binding Buffer: PBS, 1 M ADP, 1 mM MgCl$_2$.
        Stock: 704 µg HSP70 is mixed with 211 µg peptide in 1760 µl Binding Buffer
        Incubate for 30 min at 37° C.
5. CpG-peptide:
    1. ODN1826 is mixed to a concentration of 100 µg/ml (2×200 µg+2 ml water)
6. B. Pertussis:
    1. mix 4×10$^{10}$ in 2 ml PBS (2×10$^9$/dose)
7. dsRNA:
    1. P(I:C) is mixed to a concentration of 100 µg/ml in 1 ml PBS.

Adjuvant Mixture

Oil Mixture:

Group 1: 2.2 ml Specol

Group 2-7: Mix 21 ml Specol and 9 ml Vitamin E (Oil-in-Oil). Make 12 aliquots of 2.2 ml each.

Aqueous Solution:

Group 3: Al(OH)$_3$:420 µl in 10 tubes (4.2 ml). Add 2×350 µl PBS to tube 3a and 3b Group 4: HSP70: Add 200 µl to 8 tubes (1600 µl). Add 300 µl PBS to tube 4a and 4b.

Group 5: CpG: Add 400 µl to 6 tubes (2400 µl). Add 200 µl PBS to tube 5a and 5b.

Group 6: B. Pertussis: Add 400 µl to 4 tubes (1600 µl). Add 100 µl PBS to tube 6a and 6b.

Group 7: dsRNA pI:C: Add 400 µl to 2 tubes (800 µl).

Mixture

The aqueous solutions (1.8 ml/tube) are added drop by drop during vortexing to 2.2 ml oil mixture. Each tube contains immunization material for 4 chickens.

Immunization Protocol:

Day 1: 1. immunization of 4 chickens×7 groups with 1 ml adjuvant.

Day 10: 2. immunization of 4 chickens×7 groups with 1 ml adjuvant.

The mixtures are vortexed prior to use.

Blood samples are taken prior to each immunization and 14 days after the last immunization.

According to the results of the above experiments the relevant adjuvants components are chosen to be used in the final protocol to generate the antibody library.

Example 5

IgY ELISA Measurements 1. 1 µg/ml protein per well in 100 µl 10 mM phosphate buffer pH 7.4, containing 0.15 M NaCl (PBS), incubate for 2 h at room temp and then at 4° C. for 16 h.
2. Wash 3 times with PBS containing 0.1% BSA (bovine serum albumin) and 0.05% Tween 20.
3. Saturation with 200 µl PBS containing 2 mg/ml BSA for 3 h at room temperature.
4. Standard curve 0.005 to 1.28 µg/ml, Serum fivefold diluted no sample.
5. Sample diluted in 100 µl PBS containing 0.1% BSA and 0.05% Tween is dispensed into wells and placed at 4° C. for 16 h.
6. Wash 3 times with PBS containing 0.1% BSA and 0.05% Tween 20.
7. Add secondary antibody at a ratio of 1/10000 to the wells and incubate for 2 h at room temperature.
8. Wash with PBS containing 0.1% BSA and 0.05% Tween 20.
9. OPD Tablets.
10. Stop reaction by addition of sulfuric acid.
11. Measure absorbance at 450 nm.

Example 6

Antibody Purification

The peptide, protein, or chemical which the customer wants antibodies against is synthesized and coupled to an epoxy bar. Following the coupling the bar is transferred to the library. In the library relevant antibodies bind the antigens. By subsequent transfer to varying pH strength the bound antibodies can be divided into three categories: weak, medium and strong binding. The antigen is bound covalently to the bar while the antibody is linked to the antigen by ion-bonds. The weakest bound antibody is reused in the library.

Example 7

Antibody Isolation from the Egg Yolk

Classical Method with Ammonium Sulphate
1. Separate egg white and yolk. Wash the yolk with 2 volumes H$_2$O.
2. Puncture the yolk and dissolve it in 1:10 weight/volume H$_2$O.
3. Freeze and dry the solution.
4. Add solid ammonium sulphate to 25% saturation; incubate at room temperature for 20 min.
5. Centrifuge for 30 min at 2500×g.

6. Transfer the supernatant to a new glass and add solid ammonium sulphate to 40% saturation. Incubate at room temperature for 20 min.
7. Centrifuge for 30 min at 2500×g.
8. The pellet is redissolved in 1 ml PBS/0.1% NaN$_3$ Amount of ammonium sulphate (in grams) that has to be added a 1 L solution at 20° C.=553($S_2$–$S_1$)/100–0.3*$S_2$, wherein $S_2$=Final concentration of 25%; $S_1$=Start concentration, e.g. 0%-25%: 133.25 g/L and 25%-40%: 90 g/L Alternative Method 1 with NaCl
1. Separate egg white and yolk. Wash the yolk with 2 volumes H$_2$O.
2. Puncture the yolk and dissolve it in 1:10 weight/volume H$_2$O.
3. Freeze and dry the solution.
4. Add 133.25 g solid NaCl to 25% saturation, incubate at room temperature for 20 min.
5. Centrifuge for 30 min at 2500×g.
6. Transfer the supernatant to a new glass and add solid NaCl to 40% saturation. Incubate at room temperature for 20 min.
7. Centrifuge for 30 min at 2500×g.
8. The pellet is redissolved in 1 ml PBS/0.1% NaN$_3$ Alternative Method 2 with Chloroform
1. The egg yolk is separated from the egg white.
2. Add 100 mM Sodium Phosphate Buffer pH 7.6 to volume 60 ml and mix.
3. Add 40 ml chloroform and mix to a semi-solid phase.
4. Centrifuge for 30 min. at 1500 g.
5. Isolate the supernatant.
6. PEG-6000 is added to a final concentration of 12% w/v. Mix until PEG is dissolved.
7. Centrifuge for 10 min. at 16.000 g.
8. The pellet is dissolved in 100 mM Sodium Phosphate Buffer pH 7.6.
9. Sodium azide is added to 0.05%.

Example 8

Isolation of Antigen Specific Antibodies

One gram of cyanogen bromide-activated sepharose 4B (Pharmacia) was swelled according to manufacturers instructions to yield 3.5 ml of resin.

2.5 mg peptide was dissolved in 0.5 M NaCl, 0.1 M NaHCO$_3$, pH 8.3 and added to the swelled sepharose. The peptide:resin mixture was mixed for 2 hours at room temperature and centrifuged at 40×g for 5 min. The resin was subsequently incubated with blocking buffer (0.2 M Glycine, pH 8.0) at 4° C. for 16 h. The peptide:resin was then poured into a column and washed 5× with 0.5 M NaCl, 0.1 M NaHCO$_3$, pH 8.3 followed by 5 ml 0.5 M NaCl, 0.1 M ammonium acetate, pH 4.0.

After rinsing the column with 50 ml PBS, 8 ml IgY obtained in Example 3 was mixed with 42 ml PBS and loaded overnight at 4° C. at a flow rate of 30 µl/min. The column was subsequently washed with 50 ml PBS. The antibodies that did not bind to the column were dialyzed for 24 hr against 1 liter of PBS with 2 buffer changes 4° C. Cut off: 3,500. After dialyzation, antibodies can be returned to library to be used for another occasion.

Antigen specific antibodies were eluted from the column with 0.15 M NaCl, 0.2 M glycine, pH 2.2. The eluate was neutralized with 1 M Tris-HCL pH 8.0 and stored at 4° C. with 0.01% NaN$_3$.

Example 9

Affinity of Antigen Specific Antibodies

To measure the antibody affinity, purified antibody is reloaded on column. Instead of eluting with pH 2.2 a range from pH 8.0 to pH 1.0 is used. Amount of antibody released at a specific pH is measured at 280 nm. The absorbents peak of the pH range indicates its affinity.

Example 10

Isolation of Antibodies from the Antibody Library Tank

A polystyrene coated aluminium rod is epoxy coated and kept in distilled water for later use. The coated rod may be stored for several months at 2-8° C.

The rod is immersed into 0.1 M phosphate buffer, pH 7.0-8.5.

The target (protein, peptide, bacteria, virus, chemical or other component) buffer is changed to a 0.1 M phosphate buffer in the range of pH 7.0 to 8.5. The optimal amount of target will be decided in each case. The dissolved target is immediately added to the tube containing the rod whereupon thorough mixing is applied by stirring. The tube containing the rod-target mixture is put on a rotor and incubated for 6 hours at 4-37° C. The rod is washed three times using an isotonic phosphate buffered saline (PBS) pH 7.2-7.6 in order to remove the supernatant. The rod is now coated and ready for use in isolation of antibodies. The coated rod can usually be stored for several months at 2-8° C. in PBS preferably with addition of 0.02% sodium azide (final concentration) as bacteriostatic agent. The rod is subsequently transferred to the antibody library tank and incubated 1-6 hours depending of target surface. When using bacteria or virus as target the rod must be covered and isolated with a porous membrane to prevent debris-contamination of the antibody tank, yet allowing antibodies to pass.

The rod is removed from the tank and subsequently washed three times using a PBS pH 7.2-7.6 in order to remove unbound antibodies whereafter the rod is transferred to a tube with PBS pH 5.0 to remove weaker bound antibodies whereafter it is washed three times in PBS and transferred to a tube with PBS pH 3.5 to remove medium strongly bound antibodies. Wash three subsequent times in PBS and transfer the rod to a tube containing PBS pH 2.0 to remove the most tightly bound antibodies from the rod coated with secondary antigens. Wash buffer aliquots are pooled and dialysed for reuse in antibody tank except the pH 2 wash which is dialysed whereafter the antibodies are collected.

Example 11

Isolation of Peptides from the Peptide Library Tank

A polystyrene coated aluminium rod is epoxy coated and kept in distilled water for later use. The coated rod can usually be stored for several months at 2-8° C.

Immerse the rod into 0.1 M phosphate buffer, pH 7.0-8.5. Change the buffer on the antibody to a 0.1 M phosphate buffer in the range of pH 7.0 to 8.5. The dissolved target is immediately added to the tube containing the rod and mixed by stirring.

The tube is put on a rotor and incubated for 6 hours at 4-37° C.

The rod is subsequently washed three times using an isotonic phosphate buffered saline (PBS) pH 7.2-7.6 to remove the supernatant. The rod is now coated and ready for use in isolation of peptides. The coated rod can usually be stored for several months at 2-8° C. in PBS with addition of 0.02% sodium azide (final concentration) as a bacteriostatic agent. The rod is then transferred to a peptide library tank and incubated for 12 hours depending of target surface. The rod is removed from the tank and washed three times using a PBS pH 7.2-7.6 to remove unbound antibodies. The rod is subsequently transferred to the tube with a PBS pH 5.0 in order to remove weakly bound peptides. Washing in PBS is performed three times whereafter the rod is transferred to a tube containing PBS pH 3.5 to in order to remove peptides bound with medium affinity. Wash subsequently three times in PBS and transfer the rod to a tube with PBS pH 2.0 to remove strongly bound peptides. Wash through from the last step is isolated and qualitatively and quantitatively analysed with respect to the peptides.

Remaining sequenced peptide, imitating the original antigen, can be used as template for reimmunizing organisms.

Example 12

Optimal Conditions for Shipment and Storage of the Antibodies

Antibodies are very stable under mild denaturating conditions. This makes it possible to ship and store the antibodies in PBS Buffer, pH 7.0 (the antibody structure is preserved) and sodium azide 0.05% (anti-bacterial and anti-fungal) at room temperature for at least 14 days.

Storage at −20° C. is possible for years. The library will be divided into a stock at −20° C. and a stock at 1° C. to avoid damage due to thawing and freezing. Long-term storage of hybridoma cell lines for the generation of monoclonal antibodies is carried out by centrifugation at 4° C. in a solution containing nourishment and DMSO (as cryo protectant). Afterwards the hybridomas are slowly frozen and stored in liquid nitrogen.

Example 13

Monoclonal Antibodies

Removal of Bursa of Fabricius

The chickens will be killed by decapitation and the bursas of Fabricius/Bursa fabricii removed.

Bursa fabricii is removed using sterile techniques and transferred to a cell culture dish, containing 10 ml 37° C. medium without serum. Non-bursa tissue is removed. Bursa fabricii is comminute/shredded with a 19 G needle and subsequently with a pipette. The cell suspension is transferred to a sterile centrifuge bottle. The cells are allowed to settle for app. 2 min. The supernatant is transferred to sterile centrifuge bottles.

Fusions

Interspecies hybridomas are made between the antibody producing B-cells of the chicken and a sp2/0 myeloma cell line as follows:

Add 0.3 g 50° C. polyethylene glycol (PEG) to 0.7 ml medium without serum and transfer to a 37° C. water bath. Centrifuge the B-cells at 400 g for 5 min and remove the supernatant. Centrifuge 20 ml myeloma cells at 400 g for 5 min and remove the supernatant. Resuspend the cell pellets in 5 ml medium without serum. The B-cells and the myeloma cells are centrifuged at 400 g for 5 min. Remove the supernatant.

Add 0.2 ml PEG to the respective cell pellets and resuspend the pellets carefully. Centrifuge at 400 g for 5 min. Resuspend the respective pellet in 5 ml medium without serum and add 5 ml medium with 20% serum. Centrifuge at 400 g for 5 min. Resuspend the cell pellets in medium containing 20% serum, 1×OPI Oxaloacetat Pyruvat Insulin, 1×AH Azaserin Hypoxanthin.

Isolation of Antibody Producing Cells

The antibodies are displayed on the surface of the hybridoma. Therefore the hybridomas can be isolated as the antibodies are isolated as previously described. When the antibody producing hybridomas are isolated a fast production can be made.

The isolation must be carefully performed. Contamination from other cells cannot be tolerated in the production of monoclonal antibodies. The sonication has to be performed with a lower intensity, to avoid destruction of living cells. When a single cell is isolated the procedure as described in monoclonal antibody production is resumed. The probability of mistaken B-cell isolation is low, but will although be tested in ELISA.

Alternatively the hybridomas can be isolated based on the secernation of the antibodies to the medium. Identification of the antibody producing hybridomas is made by analysis of the supernatant and further subcloning of the cells. After 5-6 subcloning the antibody producing monoclonal cell will be identified and isolated.

Monoclonal Antibody Production

Hybridomas are grown in Sigmas H4409 medium. The cells are divided in to fractions. The first fraction is stored frozen for later use. The second fraction is grown to confluence and antibodies are collected when the antibody production ceases (9 days). It is expected that the antibody production is 175 µg antibody/ml medium in 9 days.

By experience it is known that problems in the production of monoclonal antibodies primarily relate to randomised fusions. Some of the hybridomas grow fast, some slow, some do not grow at all. But if the fusions take place randomly, the probability of presentation of all kinds of peptides will increase by using more cells and more fusions. If a representative mix of hybridomas is achieved, it is possible to isolate one of each type of antibody+producing hybridoma. The cells can be isolated as a gathered group of cells producing the same antibody. Later in the growth-phase a natural selection will be made where the fast growing cells will dominate. At this stage it is tested if the antibody production is efficient.

Example 14

Diversity of Antibody Library 10.000 peptides of 15 amino acid residues in length were randomly synthesized and used as the antigen library (Bib). Also 4 control peptides of 15 residues in length were synthesized: C, Ec, Sf-2, Sf-3. All peptides were C-terminally "tagged" with cysteine and coupled to the carrier protein KLH. Afterwards the peptides were mixed to make a 1:12.000 representation of all peptides: 2 mg Bib and 0.2 μg of each control peptide. The mixture was injected to 19 week old Isababcock hybrid chickens, a total of 2 mg peptide-KHL was used. Specol was used as adjuvant at a ratio of 1:1. The chickens were reimmunized (boosted) on day 10 after the first immunization.

The Control Peptides are of the Following Sequences:

1. C: CREGPTKGMHTAVQGL

2. Ec: MAPGSTVGTLVANMTC

3. Sf-2: CDKIDSYAQQDLKKGLHLYG

4. Sf-3: CFFAYSDKIDSYAQQD

Test Results:

Prior to immunization blood samples were taken (pre-serum). Date: 22/3, 4/4 and 18/4. The samples were diluted 1:100 and tested by ELISA. A 1:10.000 dilution of secondary antibody-HRP was used. In these tests, each well was pre-coated with 100 ng peptide or peptide library. Controls were performed on wells not precoated with any protein or peptide. For all measurements control measurements were performed. Measurements of blank samples are subtracted the sample measurements. All results have been reproduced. The highest obtained background signal (triple measurements) was subtracted from the ELISA results of the samples. The background signals were registered 18/4. Before this the sample results was lower or equal to the highest background signal.

ELISA Results:

Interpretation of the Results:

It is possible to immunize with 10.000 peptides and still obtain antibodies against a specific peptide. To conclude: it is possible to distribute the antibody production over as many as 10.000 antigens. The high-quantity production of antibodies in a chicken can therefore be exploited to produce small quantities of a single antibody.

Contrary to the general presumptions in the art, it is possible to immunize with large numbers of antigens, here 10,000 different peptides, AND obtaining specific antibodies. It is thus possible to produce a large amount of different antibodies in one animal and by exploiting the ability of the hen to produce large amounts of antibodies which can be collected from the eggs. It is furthermore demonstrated that immunization with small amounts of antigen is possible without inducing anaphylactic shock in the animal.

Example 15

Library Antibodies for the Treatment of Diarrhea in Piglets—Protocol I

Diarrhea in piglets is considered as one of the largest contributors (4-7% of all born piglets die of this) to the high mortality in piglets. The purpose of this experiment is to produce antibodies in chickens against pathogens causing diarrhea in piglets: Clostridia; Cocciciosis; Colibacillosis (*E. Coli*); Porcine Epidemic Diarrhoea (PED); Porcine Reproductive and Respiratory Syndrome (PRRS); Rotavirus and Transmissible Gastro-Enteritis (TGE)

Protocol I:

19 weeks old chickens, *Gallus gallus* domestica, are immunized with fragments from the pathogens (killing by heat and use all the juice) in a Super Adjuvant mixture. 100 chickens are immunized according to the scheme. Approximately 14 chickens/group. The chickens are kept isolated to ensure proper collecting of eggs.

TABLE 1

Induction of immune response in a hen to selected target antigens. The hen was immunized with a large amount and number of different peptides. Control samples were blood samples collected before immunization. The results shown in the table are reproducible.

| Dato | KLH | Bib | Bib | C | C | Ec | Ec | Sf-2 | Sf-2 | Sf-3 | Sf-3 |
|------|-----|-----|-----|---|---|----|----|------|------|------|------|
| 22/3 | 0 | 0 | 0 | 0 | 0 | 0 | 0 | 0 | 0 | 0 | 0 |
| 4/4 | 0 | 0 | 0 | 0 | 0 | 0 | 0 | 0 | 0 | 0 | 0 |
| 18/4 | 2.52 | 1.84 | 1.90 | 0.05 | 0.04 | 0.04 | 0.04 | 0.07 | 0.07 | 0.01 | 0.01 |

Experimental Period: 6 Weeks
Immunization Scheme:

| | Group | | | | | | |
|---|---|---|---|---|---|---|---|
| | 1 | 2 | 3 | 4 | 5 | 6 | 7 |
| Pathogen | Clostridia | Cocciciosis | Colibacillosis (*E. Coli*) | PED | PRRS | Rotavirus | TGE |

Immunization: day 0
Immunization: day 14
Blood samples are drawn from the chickens at day 0, 10, 20, 30.
Eggs are collected from day 21.
Evaluation of the immune response raised in chickens
The serum is isolated from the chickens, and antibody titers against the specific pathogens determined by ELISA.
Purification of IgY
The specific antibodies are purified from the egg yolks using NaCl-precipitation according to the example above. Hereafter a specific purification of the antibodies is made by immune specific affinity chromatography.

Example 16

Library Antibodies for the Treatment of Diarrhea in Piglets—Protocol II

The antibody content in the sows' milk contributes to the protection of the piglet including both resistance to infection and development of immunological tolerance to harmless environmental antigens. The listed pathogens are common in the environment of the swine farm, and the antibodies can be isolated from milk from the sow. It is important though that the sows have not been protected from this environment as is often the case. The main reason for the high mortality among piglets is the lack of antibodies transferred from the mother through the colostrum.

Isolation of antibodies against top 10 diseases causing diarrhea in piglets is performed using standard purification procedures.

Isolation of Peptide/Antigen

The peptides are magnetically coupled and the antibodies are dipped into the peptide mixture. Subsequently the peptides are eluted by their degree of affinity as this correlates with decreasing pH during the different elution steps.

The peptides thus captured are analyzed and synthesized in large quantities after which chickens are immunized with the newly synthesized peptides in larger. In this manner larger volumes of more specific antibodies may be generated and isolated. Furthermore, by analyzing the peptides caught a subtraction method of selecting for mutated pathogens can be employed.

Development of Specific Antibodies in Chicken 19 weeks old chickens, *Gallus gallus* domestica, are immunized with peptides reacting with specific antibodies in a superadjuvant mixture. Hereby a specific immune response and specific antibodies are formed in the chicken. The IgY antibodies against the pathogen/peptide are purified from the egg yolk as described elsewhere.

Alternatively the antibodies can be isolated from the antibody library by coupling the identified peptides and/or the pathogen of interest. This method is already described.

Application of Antibodies

The pathogens described in this field exert their effect through the gastrointestinal tract.

The application of antibodies may trap the antigen/pathogen in the gastrointestinal tract—thereby hinder the adherence of the pathogen and further replication. Preferably this could decrease the duration and the extent of the disease—thereby decrease the high mortality among piglets.

The antibodies are administered to the piglets in two different ways:

Coupling of antibodies 1:1 by binding of the Fc portion of two (or more) antibodies. The first antibody will trap the complex after binding to the corresponding epitope, hereafter the second antibody is able to bind another epitope creating a polyclonal antibody-antigen complex inactivating the pathogen Coupling of antibodies to a non-digestible material as clay or plastic The antibodies trap/immobilize the pathogen and due to the non-digestible material they will be transported through the gastrointestinal tract and out with the faeces.

Further embodiments of the invention include:

A method for obtaining, from a plurality of different IgY antibodies specific for one or more primary antigens, one or more IgY antibodies, but not all of said plurality of IgY antibodies, wherein said isolated IgY antibodies are also specific for one or more secondary antigens, said method comprising the steps of i) generating a plurality of IgY antibodies by immunizing each of a plurality of avian organisms of the same or different species with a composition comprising a plurality of different first antigens, thereby generating a plurality of different IgY antibodies, ii) providing one or more secondary antigen(s) to be tested, iii) contacting said one or more secondary antigen(s) with the plurality of different IgY antibodies specific for one or more primary antigens as generated in step i), and iv) obtaining one or more IgY antibodies having a specificity for both one or more of said primary antigens and one or more of said secondary antigens, v) wherein the primary and secondary antigens are not identical, and vi) wherein the obtained IgY antibodies specific for said one or more secondary antigens have been raised against said one or more primary antigens only.

In one embodiment the method comprises the further step of extracting said different IgY antibodies from eggs laid by said plurality of avian organisms.

In another embodiment the method comprises the further step of purifying said different IgY antibodies.

In another embodiment at least some of the primary and/or secondary antigens comprise one or more peptide(s).

In another embodiment substantially all of the primary and/or secondary antigens comprise one or more peptide(s).

In another embodiment at least some of the primary and/or secondary antigens consist of one or more peptide(s).

In another embodiment the method comprises substantially all of the primary and/or secondary antigens consist of one or more peptide(s).

In another embodiment said one or more peptides comprise natural and/or non-natural amino acid residues.

In another embodiment said one or more peptide(s) contain amino acid residues selected from the group consisting of natural amino acid residues and non-natural amino acid residues.

In another embodiment said one or more peptide(s) contain natural amino acid residues.

In another embodiment said one or more peptide(s) contain non-natural amino acid residues.

In another embodiment at least some of said primary and/or secondary antigens comprise two or more peptides linked covalently or non-covalently by a chemical moiety.

In another embodiment the chemical moiety is selected from moieties comprising a bond selected from the group consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

In another embodiment the chemical moiety does not comprise or consist of an amino acid residue.

In another embodiment the chemical moiety comprises or consists of a polymer to which different antigens are covalently attached.

In another embodiment the polymer is in the form of a beaded or granulated resin.

In another embodiment the resin is selected from the group consisting of styrenes, acrylates, unsaturated chlorides, esters, acetates, amides, and alcohols, such as polystyrene, for example high density polystyrene latexes, such as brominated polystyrene, polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidenechloride, and polydivinylbenzene, as well as PEGA, SPOCC, and POEPOP, HYDRA, PEG-polyacrylate copolymers, polyether-polyamine copolymers, cross-linked polyethylene diamines, and combinations thereof.

In another embodiment the resin is selected from the group consisting of styrenes, acrylates, unsaturated chlorides, esters, acetates, amides, alcohols, polystyrene, high density polystyrene latexes, brominated polystyrene, polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidenechloride, polydivinylbenzene, PEGA, SPOCC, POEPOP, HYDRA, PEG-polyacrylate copolymers, polyether-polyamine copolymers, cross-linked polyethylene diamines, and combinations thereof.

In another embodiment said natural amino acids are selected from the group consisting of tyrosine, glycine, phenylalanine, methionine, alanine, serine, isoleucine, leucine, threonine, valine, praline, lysine, histidine, glutamine, glutamic acid, tryptophan, arginine, aspartic acid, asparagine, cysteine, selenocysteine and pyrrolysine.

In another embodiment at least some of said one or more peptide(s) are attached to a functional entity by one or more covalent or non-covalent linker residue(s) linking the one or more peptide(s) to the functional entity.

In another embodiment the linker residue is selected from residues comprising a bond selected from the group consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

In another embodiment bonds joining individual peptide residues are selected from the group consisting of peptide bonds, imine bonds and imide bonds.

In another embodiment said one or more peptide(s) each comprise one or more peptide domain(s) selected from the group consisting of an □-peptide domain, a □-peptide domain, a □-peptide domain, an □-peptide domain, a mono-, di- and tri-substituted □-peptide domain, a mono-, di- and tri-substituted □-peptide domain, a mono-, di- and tri-substituted □-peptide domain, a mono-, di- and tri-substituted □-peptide domain, a peptide domain wherein the amino acid residues are in the L-form, a peptide domain wherein the amino acid residues are in the D-form, a peptide domain wherein the amino acid residues are both in the L-form and in the D-form, a vinylogous peptide domain, a glyco-peptide domain, a vinylogous sulfonamide peptide domain, a polysulfonamide domain, a conjugated peptide domain and a conjugated peptide domain comprising one or more functional group(s), such as one or more prosthetic group(s).

In another embodiment at least some of said primary and/or secondary antigens comprise one or more entities selected from the group consisting of —NHN(R)CO—; —NHB(R)CO—; —NHC(RR')CO—; —NHC(=CHR)CO—; —NHC6H4CO—; —NHCH2CHRCO—; —NHCHRCH2CO—; —COCH2-; —COS—; —CONR—; —COO—; —CSNH—; —CH2NH—; —CH2CH2-; —CH2S—; —CH2SO—; —CH2SO2-; —CH(CH3)S—; —CH=CH—; —NHCO—; —NHCONH—; —CONHO—; —C(=CH2)CH2-; —PO2-NH—; —PO2-CH2-; —PO2-CH2N+-; —SO$_2$NH—, wherein R is H or an optionally substituted alkyl.

In another embodiment each peptide contains at least 5 amino acid residues, such as at least 6 amino acid residues, selected independently from each of the following groups i) to xiii) consisting of i) Amino acids having polar side chains (Asp, Glu, Lys, Arg, His, Asn, Gln, Ser, Thr, Tyr, and Cys,)

ii) Amino acids having non-polar side chains (Gly, Ala, Val, Leu, Ile, Phe, Trp, Pro, and Met)

iii) Amino acids having aliphatic side chains (Gly, Ala Val, Leu, Ile)

iv) Amino acids having cyclic side chains (Phe, Tyr, Trp, His, Pro)

v) Amino acids having aromatic side chains (Phe, Tyr, Trp)

vi) Amino acids having acidic side chains (Asp, Glu)

vii) Amino acids having basic side chains (Lys, Arg, His)

viii) Amino acids having amide side chains (Asn, Gln)

ix) Amino acids having hydroxy side chains (Ser, Thr)

x) Amino acids having sulphur-containing side chains (Cys, Met), xi) Neutral, weakly hydrophobic amino acids (Pro, Ala, Gly, Ser, Thr)

xii) Hydrophilic, acidic amino acids (Gln, Asn, Glu, Asp), and xiii) Hydrophobic amino acids (Leu, Ile, Val)

In another embodiment the natural and/or non-natural amino acids are modified.

In another embodiment the modifications are selected from the group consisting of phosphorylation, sulfation, glycosylation, methylation, and acetylation.

In another embodiment the avian organisms are of the same species.

In another embodiment the avian organisms are of different species.

In another embodiment the avian species is a female.

In another embodiment the female avian species is a hen.

In another embodiment the avian organism is a bird of the gallinacean type.

In another embodiment the avian organism is *Gallus gallus domestica*.

In another embodiment a total of from 1000 to 100000 avian organisms are immunized.

In another embodiment the number of avian organisms immunized is in the range of from 1000 to 38000, such as from 1000 to 36000, for example from 1000 to 34000, such as from 1000 to 32000, for example from 1000 to 30000, such as from 1000 to 28000, for example from 1000 to 26000, such as from 1000 to 24000, for example from 1000 to 22000, such as from 1000 to 20000, for example from 1000 to 19000, such as from 1000 to 18000, for example from 1000 to 17000, such as from 1000 to 16000, for example from 1000 to 15000, such as from 1000 to 14000, for example from 1000 to 12000, such as from 1000 to 11000, for example from 1000 to 10000, such as from 1000 to 9000, for example from 1000 to 8000, such as from 1000 to 7000, for example from 1000 to 6000, such as from 1000 to 5000, such as from 2000 to 36000, for example from 2000 to 34000, such as from 2000 to 32000, for example from 2000 to 30000, such as from 2000 to 28000, for example from 2000 to 26000, such as from 2000 to 24000, for example from 2000 to 22000, such as from 2000 to 20000, for example from 2000 to 19000, such as from 2000 to 18000, for example from 2000 to 17000, such as from 2000 to 16000, for example from 2000 to 15000, such as from 2000 to 14000, for example from 2000 to 12000, such as from 2000 to 11000, for example from 2000 to 10000, such as from 2000 to 9000, for example from 2000 to 8000, such as from 2000 to 7000, for example from 2000 to 6000, such as from 2000 to 5000, such as from 3000 to 36000, for example from 3000 to 34000, such as from 3000 to 32000, for example from 3000 to 30000, such as from 3000 to 28000, for example from 3000 to 26000, such as from 3000 to 24000, for example from 3000 to 22000, such as from 3000 to 20000, for example from 3000 to 19000, such as from 3000 to 18000, for example from 3000 to 17000, such as from 3000 to 16000, for example from 3000 to 15000, such as from 3000 to 14000, for example from 3000 to 13000, such as from 3000 to 12000, for example from 3000 to 11000, such as from 10000 to 9000, for example from 3000 to 8000, such as from 3000 to 7000, for example from 3000 to 6000, such as from 3000 to 5000, such as from 4000 to 36000, for example from 4000 to 34000, such as from 4000 to 32000, for example from 4000 to 30000, such as from 4000 to 28000, for example from 4000 to 26000, such as from 4000 to 24000, for example from 4000 to 22000, such as from 4000 to 20000, for example from 4000 to 19000, such as from 4000 to 18000, for example from 4000 to 17000, such as from 4000 to 16000, for example from 4000 to 15000, such as from 4000 to 14000, for example from 4000 to 13000, such as from 4000 to 12000, for example from 4000 to 11000, such as from 4000 to 10000, for example from 4000 to 9000, such as from 4000 to 8000, for example from 4000 to 7000, such as from 4000 to 6000, such as from 5000 to 36000, for example from 5000 to 34000, such as from 5000 to 32000, for example from 5000 to 30000, such as from 5000 to 28000, for example from 5000 to 26000, such as from 5000 to 24000, for example from 5000 to 22000, such as from 5000 to 20000, for example from 5000 to 19000, such as from 5000 to 18000, for example from 5000 to 17000, such as from 5000 to 16000, for example from 5000 to 15000, such as from 5000 to 14000, for example from 5000 to 13000, such as from 5000 to 12000, for example from 5000 to 11000, such as from 5000 to 10000, for example from 5000 to 9000, such as from 5000 to 8000, for example from 5000 to 7000, such as from 6000 to 36000, for example from 6000 to 34000, such as from 6000 to 32000, for example from 6000 to 30000, such as from 6000 to 28000, for example from 6000 to 26000, such as from 6000 to 24000, for example from 6000 to 22000, such as from 6000 to 20000, for example from 6000 to 19000, such as from 6000 to 18000, for example from 6000 to 17000, such as from 6000 to 16000, for example from 6000 to 15000, such as from 6000 to 14000, for example from 6000 to 13000, such as from 6000 to 12000, for example from 6000 to 11000, such as from 6000 to 10000, for example from 6000 to 9000, such as from 6000 to 8000, such as from 7000 to 36000, for example from 7000 to 34000, such as from 7000 to 32000, for example from 7000 to 30000, such as from 7000 to 28000, for example from 7000 to 26000, such as from 7000 to 24000, for example from 7000 to 22000, such as from 7000 to 20000, for example from 7000 to 19000, such as from 7000 to 18000, for example from 7000 to 17000, such as from 7000 to 16000, for example from 7000 to 15000, such as from 7000 to 14000, for example from 7000 to 13000, such as from 7000 to 12000, for example from 7000 to 11000, such as from 7000 to 10000, for example from 7000 to 9000, such as from 8000 to 36000, for example from 8000 to 34000, such as from 8000 to 32000, for example from 8000 to 30000, such as from 8000 to 28000, for example from 8000 to 26000, such as from 8000 to 24000, for example from 8000 to 22000, such as from 8000 to 20000, for example from 8000 to 19000, such as from 8000 to 18000, for example from 8000 to 17000, such as from 8000 to 16000, for example from 8000 to 15000, such as from 8000 to 14000, for example from 8000 to 13000, such as from 8000 to 12000, for example from 8000 to 11000, such as from 8000 to 10000, such as from 9000 to 36000, for example from 9000 to 34000, such as from 9000 to 32000, for example from 9000 to 30000, such as from 9000 to 28000, for example from 9000 to 26000, such as from 9000 to 24000, for example from 9000 to 22000, such as from 9000 to 20000, for example from 9000 to 19000, such as from 9000 to 18000, for example from 9000 to 17000, such as from 9000 to 16000, for example from 9000 to 15000, such as from 9000 to 14000, for example from 9000 to 13000, such as from 9000 to 12000, for example from 9000 to 11000, such as from 10000 to 36000, for example from 10000 to 34000, such as from 10000 to 32000, for example from 10000 to 30000, such as from 10000 to 28000, for example from 10000 to 26000, such as from 10000 to 24000, for example from 10000 to 22000, such as from 10000 to 20000, for example from 10000 to 19000, such as from 10000 to 18000, for example from 10000 to 17000, such as from 10000 to 16000, for example from 10000 to 15000, such as from 10000 to 14000, for example from 10000 to 13000, such as from 10000 to 12000, such as from 12000 to 36000, for example from 12000 to 34000, such as from 12000 to 32000, for example from 12000 to 30000, such as from 12000 to 28000, for example from 12000 to 26000, such as from 12000 to 24000, for example from 12000 to 22000, such as from 12000 to 20000, for example from 12000 to 19000, such as from 12000 to 18000, for example from 12000 to 17000, such as from 12000 to 16000, for example from 12000 to 15000, such as from 12000 to 14000, such as from 14000 to 36000, for example from 14000 to 34000, such as from 14000 to 32000, for example from 14000 to 30000, such as from 14000 to 28000, for example from 14000 to 26000, such as from 14000 to 24000, for example from 14000 to 22000, such as from 14000 to 20000, for example from 14000 to 19000, such as from 14000 to 18000, for example from 14000 to 17000, such as from 14000 to 16000, such as from 16000 to 36000, for example from 16000 to 34000, such as from 16000 to 32000, for example from 16000 to 30000, such as from 16000 to 28000, for example from 16000 to 26000, such as from 16000 to 24000, for example from 16000 to 22000, such as from 16000 to 20000, for example from 16000 to 19000, such as from 16000 to 18000, such as from 18000 to 36000, for example from 18000 to 34000, such as from 18000 to 32000, for example from 18000 to 30000, such as from 18000 to 28000, for example from 18000 to 26000, such as from 18000 to 24000, for example from 18000 to 22000, such as from 18000 to 20000, such as from 20000 to 36000, for example from 20000 to 34000, such as from 20000 to 32000, for example from 20000 to 30000, such as from 20000 to 28000, for example from 20000 to 26000, such as from 20000 to 24000, for example from 20000 to 22000.

In another embodiment the number of avian organisms immunized is in the range of from 1000 to 38000.

In another embodiment the number of avian organisms immunized is about 1000, such as about 2000, for example about 3000, such as about 4000, for example about 5000, such as about 5500, for example about 6000, such as about 6500, for example about 7000, such as about 75000, for example about 8000, such as about 8500, for example about 9000, such as about 9500, for example about 10000, such as about 10500, for example about 11000, such as about 115000, for example about 12000, such as about 12500, for example about 13000, such as about 13500, for example about 14000, such as about 14500, for example about 15000, such as about 16000, for example about 17000, such as about 18000, for example about 19000, such as about 20000, for example about 21000, such as about 22000, for example about 23000, such as about 24000, for example about 25000, such as about 26000, for example about 27000, such as about 28000, for example about 29000, such as about 30000, for example about 31000, such as about 32000, for example about 33000, such as about 34000, for example about 35000, such as about 36000, for example about 37000, such as about 38000, for example about 39000, such as about 40000, for example about 41000, such as about 42000, for example about 43000, such as about 44000, for example about 45000, such as about 50000.

In another embodiment the avian organisms are immunized by oral administration or injection of the composition comprising the different antigens.

In another embodiment the avian organisms are immunized by oral administration or injection of the composition comprising the different peptides.

In another embodiment the different peptides are administered by means of administration one or more nucleic acids each comprising an expression signal operably linked to a region coding for one or more of the different peptide(s) to be administered, wherein said coding region is expressed in the avian organism under the control of the expression signal following the administration of said one or more nucleic acids, and wherein said expression results in the production in said avian species of said different peptides each being coded for by a corresponding nucleic acid coding region.

In another embodiment different IgY antibodies are generated in substantially each different avian organism.

In another embodiment the method comprises the further step of subsequently immunizing the avian organism directly with a plurality of peptides, which can be identical or different from the peptides used for the initial immunisation.

In another embodiment at least some of the peptides used for the initial immunization and the subsequent immunization are identical.

In another embodiment the method for immunizing the avian organisms comprises the initial and optional subsequent step(s) of injecting the different antigens directly into said avian organisms.

In another embodiment the injection is an intramuscular injection and/or a subcutaneous injection.

In another embodiment the injection is an intramuscular injection.

In another embodiment the length of the different peptides is in the range of from 5 amino acid residues to preferably less than 10000 amino acid residues, such as from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 6 to less than 5000 amino acid residues, for example from 6 to less than 1000 amino acid residues, such as from 6 to less than 900 amino acid residues, for example from 6 to less than 800 amino acid residues, such as from 6 to less than 700 amino acid residues, for example from 6 to less than 600 amino acid residues, such as from 6 to less than 500 amino acid residues, for example from 6 to less than 400 amino acid residues, such as from 6 to less than 300 amino acid residues, for example from 6 to less than 200 amino acid residues, such as from 6 to less than 100 amino acid residues, for example from 6 to less than 90 amino acid residues, such as from 6 to less than 80 amino acid residues, for example from 6 to less than 70 amino acid residues, such as from 6 to less than 60 amino acid residues, for example from 6 to less than 50 amino acid residues, such as from 6 to less than 40 amino acid residues, for example from 6 to less than 35 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 20 amino acid residues, for example from 6 to less than 19 amino acid residues, such as from 6 to less than 18 amino acid residues, for example from 6 to less than 17 amino acid residues, such as from 6 to less than 16 amino acid residues, for example from 6 to less than 15 amino acid residues, such as from 6 to less than 14 amino acid residues, for example from 6 to less than 13 amino acid residues, such as from 6 to less than 12 amino acid residues, for example from 6 to less than 11 amino acid residues, such as from 6 to less than 10 amino acid residues, for example from 6 to less than 9 amino acid residues, such as from 6 to less than 8 amino acid residues, such as from 7 to less than 5000 amino acid residues, for example from 7 to less than 1000 amino acid residues, such as from 7 to less than 900 amino acid residues, for example from 7 to less than 800 amino acid residues, such as from 7 to less than 700 amino acid residues, for example from 7 to less than 600 amino acid residues, such as from 7 to less than 500 amino acid residues, for example from 7 to less than 400 amino acid residues, such as from 7 to less than 300 amino acid residues, for example from 7 to less than 200 amino acid residues, such as from 7 to less than 100 amino acid residues, for example from 7 to less than 90 amino acid residues, such as from 7 to less than 80 amino acid residues, for example from 7 to less than 70 amino acid residues, such as from 7 to less than 60 amino acid residues, for example from 7 to less than 50 amino acid residues, such as from 7 to less than 40 amino acid residues, for example from 7 to less than 35 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 20 amino acid residues, for example from 7 to less than 19 amino acid residues, such as from 7 to less than 18 amino acid residues, for example from 7 to less than 17 amino acid residues, such as from 7 to less than 16 amino acid residues, for example from 7 to less than 15 amino acid residues, such as from 7 to less than 14 amino acid residues, for example from 7 to less than 13 amino acid residues, such as from 7 to less than 12 amino acid residues, for example from 7 to less than 11 amino acid residues, such as from 7 to less than 10 amino acid residues, for example from 7 to less than 9 amino acid residues, such as from 8 to less than 5000 amino acid residues, for example from 8 to less than 1000 amino acid residues, such as from 8 to less than 900 amino acid residues, for example from 8 to less than 800 amino acid residues, such as from 8 to less than 700 amino acid residues, for example from 8 to less than 600 amino acid residues, such as from 8 to less than 500 amino acid residues, for example from 8 to less than 400 amino acid residues, such as from 8 to less than 300 amino acid residues, for example from 8 to less than 200 amino acid residues, such as from 8 to less than 100 amino acid residues, for example from 8 to less than 90 amino acid residues, such as from 8 to less than 80 amino acid residues, for example from 8 to less than 70 amino acid residues, such as from 8 to less than 60 amino acid residues, for example from 8 to less than 50 amino acid residues, such as from 8 to less than 40 amino acid residues, for example from 8 to less than 35 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 20 amino acid residues, for example from 8 to less than 19 amino acid residues, such as from 8 to less than 18 amino acid residues, for example from 8 to less than 17 amino acid residues, such as from 8 to less than 16 amino acid residues, for example from 8 to less than 15 amino acid residues, such as from 8 to less than 14 amino acid residues, for example from 8 to less than 13 amino acid residues, such as from 8 to less than 12 amino acid residues, for example from 8 to less than 11 amino acid residues, such as from 8 to less than 10 amino acid residues, such as from 9 to less than 5000 amino acid residues, for example from 9 to less than 1000 amino acid residues, such as from 9 to less than 900 amino acid residues, for example from 9 to less than 800 amino acid residues, such as from 9 to less than 700 amino acid residues, for example from 9 to less than 600 amino acid residues, such as from 9 to less than 500 amino acid residues, for example from 9 to less than 400 amino acid residues, such as from 9 to less than 300 amino acid residues, for example from 9 to less than 200 amino acid residues, such as from 9 to less than 100 amino acid residues, for example from 9 to less than 90 amino acid residues, such as from 9 to less than 80 amino acid residues, for example from 9 to less than 70 amino acid residues, such as from 9 to less than 60 amino acid residues, for example from 9 to less than 50 amino acid residues, such as from 9 to less than 40 amino acid residues, for example from 9 to less than 35 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 20 amino acid residues, for example from 9 to less than 19 amino acid residues, such as from 9 to less than 18 amino acid residues, for example from 9 to less than 17 amino acid residues, such as from 9 to less than 16 amino acid residues, for example from 9 to less than 15 amino acid residues, such as from 9 to less than 14 amino acid residues, for example from 9 to less than 13 amino acid residues, such as from 9 to less than 12 amino acid residues, for example from 9 to less than 11 amino acid residues, such as from 10 to less than 5000 amino acid residues, for example from 10 to less than 1000 amino acid residues, such as from 10 to less than 900 amino acid residues, for example from 10 to less than 800 amino acid residues, such as from 10 to less than 700 amino acid residues, for example from 10 to less than 600 amino acid residues, such as from 10 to less than 500 amino acid residues, for example from 10 to less than 400 amino acid residues, such as from 10 to less than 300 amino acid residues, for example from 10 to less than 200 amino acid residues, such as from 10 to less than 100 amino acid residues, for example from 10 to less than 90 amino acid residues, such as from 10 to less than 80 amino acid residues, for example from 10 to less than 70 amino acid residues, such as from 10 to less than 60 amino acid residues, for example from 10 to less than 50 amino acid residues, such as from 10 to less than 40 amino acid residues, for example from 10 to less than 35 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 20 amino acid residues, for example from 10 to less than 19 amino acid residues, such as from 10 to less than 18 amino acid residues, for example from 10 to less than 17 amino acid residues, such as from 10 to less than 16 amino acid residues, for example from 10 to less than 15 amino acid residues, such as from 10 to less than 14 amino acid residues, for example from 10 to less than 13 amino acid residues, such as from 10 to less than 12 amino acid residues, such as from 11 to less than 5000 amino acid residues, for example from 11 to less than 1000 amino acid residues, such as from 11 to less than 900 amino acid residues, for example from 11 to less than 800 amino acid residues, such as from 11 to less than 700 amino acid residues, for example from 11 to less than 600 amino acid residues, such as from 11 to less than 500 amino acid residues, for example from 11 to less than 400 amino acid residues, such as from 11 to less than 300 amino acid residues, for example from 11 to less than 200 amino acid residues, such as from 11 to less than 100 amino acid residues, for example from 11 to less than 90 amino acid residues, such as from 11 to less than 80 amino acid residues, for example from 11 to less than 70 amino acid residues, such as from 11 to less than 60 amino acid residues, for example from 11 to less than 50 amino acid residues, such as from 11 to less than 40 amino acid residues, for example from 11 to less than 35 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 20 amino acid residues, for example from 11 to less than 19 amino acid residues, such as from 11 to less than 18 amino acid residues, for example from 11 to less than 17 amino acid residues, such as from 11 to less than 16 amino acid residues, for example from 11 to less than 15 amino acid residues, such as from 11 to less than 14 amino acid residues, for example from 11 to less than 13 amino acid residues, such as from 12 to less than 5000 amino acid residues, for example from 12 to less than 1000 amino acid residues, such as from 12 to less than 900 amino acid residues, for example from 12 to less than 800 amino acid residues, such as from 12 to less than 700 amino acid residues, for example from 12 to less than 600 amino acid residues, such as from 12 to less than 500 amino acid residues, for example from 12 to less than 400 amino acid residues, such as from 12 to less than 300 amino acid residues, for example from 12 to less than 200 amino acid residues, such as from 12 to less than 100 amino acid residues, for example from 12 to less than 90 amino acid residues, such as from 12 to less than 80 amino acid residues, for example from 12 to less than 70 amino acid residues, such as from 12 to less than 60 amino acid residues, for example from 12 to less than 50 amino acid residues, such as from 12 to less than 40 amino acid residues, for example from 12 to less than 35 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 20 amino acid residues, for example from 12 to less than 19 amino acid residues, such as from 12 to less than 18 amino acid residues, for example from 12 to less than 17 amino acid residues, such as from 12 to less than 16 amino acid residues, for example from 12 to less than 15 amino acid residues, such as from 12 to less than 14 amino acid residues, such as from 13 to less than 5000 amino acid residues, for example from 13 to less than 1000 amino acid residues, such as from 13 to less than 900 amino acid residues, for example from 13 to less than 800 amino acid residues, such as from 13 to less than 700 amino acid residues, for example from 13 to less than 600 amino acid residues, such as from 13 to less than 500 amino acid residues, for example from 13 to less than 400 amino acid residues, such as from 13 to less than 300 amino acid residues, for example from 13 to less than 200 amino acid residues, such as from 13 to less than 100 amino acid residues, for example from 13 to less than 90 amino acid residues, such as from 13 to less than 80 amino acid residues, for example from 13 to less than 70 amino acid residues, such as from 13 to less than 60 amino acid residues, for example from 13 to less than 50 amino acid residues, such as from 13 to less than 40 amino acid residues, for example from 13 to less than 35 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 20 amino acid residues, for example from 13 to less than 19 amino acid residues, such as from 13 to less than 18 amino acid residues, for example from 13 to less than 17 amino acid residues, such as from 13 to less than 16 amino acid residues, for example from 13 to less than 15 amino acid residues, such as from 14 to less than 5000 amino acid residues, for example from 14 to less than 1000 amino acid residues, such as from 14 to less than 900 amino acid residues, for example from 14 to less than 800 amino acid residues, such as from 14 to less than 700 amino acid residues, for example from 14 to less than 600 amino acid residues, such as from 14 to less than 500 amino acid residues, for example from 14 to less than 400 amino acid residues, such as from 14 to less than 300 amino acid residues, for example from 14 to less than 200 amino acid residues, such as from 14 to less than 100 amino acid residues, for example from 14 to less than 90 amino acid residues, such as from 14 to less than 80 amino acid residues, for example from 14 to less than 70 amino acid residues, such as from 14 to less than 60 amino acid residues, for example from 14 to less than 50 amino acid residues, such as from 14 to less than 40 amino acid residues, for example from 14 to less than 35 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 20 amino acid residues, for example from 14 to less than 19 amino acid residues, such as from 14 to less than 18 amino acid residues, for example from 14 to less than 17 amino acid residues, such as from 14 to less than 16 amino acid residues, such as from 15 to less than 5000 amino acid residues, for example from 15 to less than 1000 amino acid residues, such as from 15 to less than 900 amino acid residues, for example from 15 to less than 800 amino acid residues, such as from 15 to less than 700 amino acid residues, for example from 15 to less than 600 amino acid residues, such as from 15 to less than 500 amino acid residues, for example from 15 to less than 400 amino acid residues, such as from 15 to less than 300 amino acid residues, for example from 15 to less than 200 amino acid residues, such as from 15 to less than 100 amino acid residues, for example from 15 to less than 90 amino acid residues, such as from 15 to less than 80 amino acid residues, for example from 15 to less than 70 amino acid residues, such as from 15 to less than 60 amino acid residues, for example from 15 to less than 50 amino acid residues, such as from 15 to less than 40 amino acid residues, for example from 15 to less than 35 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 20 amino acid residues, for example from 15 to less than 19 amino acid residues, such as from 15 to less than 18 amino acid residues, for example from 15 to less than 17 amino acid residues, such as from 16 to less than 5000 amino acid residues, for example from 16 to less than 1000 amino acid residues, such as from 16 to less than 900 amino acid residues, for example from 16 to less than 800 amino acid residues, such as from 16 to less than 700 amino acid residues, for example from 16 to less than 600 amino acid residues, such as from 16 to less than 500 amino acid residues, for example from 16 to less than 400 amino acid residues, such as from 16 to less than 300 amino acid residues, for example from 16 to less than 200 amino acid residues, such as from 16 to less than 100 amino acid residues, for example from 16 to less than 90 amino acid residues, such as from 16 to less than 80 amino acid residues, for example from 16 to less than 70 amino acid residues, such as from 16 to less than 60 amino acid residues, for example from 16 to less than 50 amino acid residues, such as from 16 to less than 40 amino acid residues, for example from 16 to less than 35 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 20 amino acid residues, for example from 16 to less than 19 amino acid residues, such as from 16 to less than 18 amino acid residues, such as from 17 to less than 5000 amino acid residues, for example from 17 to less than 1000 amino acid residues, such as from 17 to less than 900 amino acid residues, for example from 17 to less than 800 amino acid residues, such as from 17 to less than 700 amino acid residues, for example from 17 to less than 600 amino acid residues, such as from 17 to less than 500 amino acid residues, for example from 17 to less than 400 amino acid residues, such as from 17 to less than 300 amino acid residues, for example from 17 to less than 200 amino acid residues, such as from 17 to less than 100 amino acid residues, for example from 17 to less than 90 amino acid residues, such as from 17 to less than 80 amino acid residues, for example from 17 to less than 70 amino acid residues, such as from 17 to less than 60 amino acid residues, for example from 17 to less than 50 amino acid residues, such as from 17 to less than 40 amino acid residues, for example from 17 to less than 35 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 20 amino acid residues, for example from 17 to less than 19 amino acid residues, such as from 18 to less than 5000 amino acid residues, for example from 18 to less than 1000 amino acid residues, such as from 18 to less than 900 amino acid residues, for example from 18 to less than 800 amino acid residues, such as from 18 to less than 700 amino acid residues, for example from 18 to less than 600 amino acid residues, such as from 18 to less than 500 amino acid residues, for example from 18 to less than 400 amino acid residues, such as from 18 to less than 300 amino acid residues, for example from 18 to less than 200 amino acid residues, such as from 18 to less than 100 amino acid residues, for example from 18 to less than 90 amino acid residues, such as from 18 to less than 80 amino acid residues, for example from 18 to less than 70 amino acid residues, such as from 18 to less than 60 amino acid residues, for example from 18 to less than 50 amino acid residues, such as from 18 to less than 40 amino acid residues, for example from 18 to less than 35 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 20 amino acid residues, such as from 19 to less than 5000 amino acid residues, for example from 19 to less than 1000 amino acid residues, such as from 19 to less than 900 amino acid residues, for example from 19 to less than 800 amino acid residues, such as from 19 to less than 700 amino acid residues, for example from 19 to less than 600 amino acid residues, such as from 19 to less than 500 amino acid residues, for example from 19 to less than 400 amino acid residues, such as from 19 to less than 300 amino acid residues, for example from 19 to less than 200 amino acid residues, such as from 19 to less than 100 amino acid residues, for example from 19 to less than 90 amino acid residues, such as from 19 to less than 80 amino acid residues, for example from 19 to less than 70 amino acid residues, such as from 19 to less than 60 amino acid residues, for example from 19 to less than 50 amino acid residues, such as from 19 to less than 40 amino acid residues, for example from 19 to less than 35 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues.

In another embodiment the length of the different peptides is in the range of from 5 amino acid residues to preferably less than 10000 amino acid residues.

The method of claims 1 to 45, wherein each avian species is immunized with a number of primary antigens in the range of from 2 to less than 100000.

In another embodiment the method further comprises administering said primary antigens to said avian organism(s) in the presence of one or more carrier(s) covalently or non-covalently attached to at least some of said antigens.

In another embodiment the method further comprises administering said primary antigens to said avian organism(s) in the presence of one or more adjuvant(s) covalently or non-covalently attached to at least some of said antigens and/or at least some of said one or more carrier(s).

In another embodiment said one or more carrier(s) and at least some of said primary antigens are both non-conjugated.

In another embodiment said one or more carrier(s) is conjugated and at least some of said primary antigens are non-conjugated.

The method of claim 47, wherein said one or more carrier(s) is conjugated and said primary antigens are all non-conjugated.

In another embodiment said one or more carrier(s) is non-conjugated and at least some of said primary antigens are conjugated.

In another embodiment said one or more carrier(s) is non-conjugated and said primary antigens are all conjugated.

In another embodiment said one or more carrier(s) and all of said primary antigens are conjugated.

In another embodiment said one or more carrier(s) and at least some of said primary antigens are both non-conjugated.

In another embodiment said one or more carrier(s) and all of said primary antigens are both non-conjugated.

In another embodiment said one or more carrier(s) is conjugated to at least some of said primary antigens.

In another embodiment carrier is a scaffold capable of presenting said primary antigens to an HLA complex in said avian.

In another embodiment the carrier is selected from the group consisting of phosphate, citrate, and other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids, such as glycine, glutamine, asparagine, arginine or lysine; monosaccharides, disaccharides, and other carbohydrates including glucose, mannose, or dextrins; chelating agents such as EDTA; sugar alcohols, such as mannitol or sorbitol; salt-forming counterions, such as sodium; and/or nonionic surfactants, such as TWEEN™, polyethylene glycol (PEG), and PLURONICS™.

In another embodiment the carrier is selected from the group consisting of phosphate, citrate, and other organic acids; antioxidants including ascorbic acid; low molecular weight (less than about 10 residues) polypeptides; proteins, serum albumin, gelatin, or immunoglobulins; hydrophilic polymers, polyvinylpyrrolidone; amino acids, glycine, glutamine, asparagine, arginine or lysine; monosaccharides, disaccharides, carbohydrates including glucose, mannose, dextrins; chelating agents EDTA; sugar alcohols, mannitol or sorbitol; salt-forming counterions, sodium; nonionic surfactants, TWEEN™, polyethylene glycol (PEG), and PLURONICS™.

In another embodiment the adjuvant is selected from the group consisting of mineral salts, such as aluminium hydroxide and aluminium or calcium phosphates gels, oil emulsions and surfactant based formulations such as MF59 (microfluidised detergent stabilised oil in water emulsion), QS21 (purified saponin), AS02 (SBAS2, oil-in-water emulsion+monophosphoryl lipid A (MPL)+QS21), Montanide ISA 51 and ISA-720 (stabilised water in oil emulsion), Adjuvant 65 (containing peanut oil, mannide monooleate and aluminium monostearate), RIBI ImmunoChem Research Inc., Hamilton, Utah), particulate adjuvants, such as virosomes (unilamellar liposomal cehicles incorporating influenza haemagglutinin), AS04 (Al salt with MPL), ISCOMS (structured complex of saponins and lipids (such as cholesterol), polyactide co-glycolide (PLG), microbial derivatives (natural and synthetic) such as monophosphoryl lipid A (MPL), Detox (MPL+*M. Phlei* cell wall skeleton), AGP (RC-529 (synthetic acylated monosaccharide)), DC_chol (lipoidal immunostimulators able to self organise into liposomes), OM-174 (lipid A derivative), CpG motifs (synthetic oligonucleotides containing immunostimulatory CpG motifs), modified bacterial toxins, LT and CT, with non-toxic adjuvant effects, Endogenous human immunomodulators, e.g., hGM-CSF or hIL-12 or Immudaptin (C3d tandem array), and inert vehicles, such as gold particles.

In another embodiment the method comprises the further step of targeting one or more of the obtained IgY antibodies having a specificity for both one or more of said primary antigens and one or more of said secondary antigens to a ligand having an affinity for one or more of said IgY antibodies.

In another embodiment the ligand is selected from the group consisting of a protein, a peptide, a carbohydrate, a polysaccharide, a glycoprotein, a hormone, a receptor, an antigen, an antibody, a virus, a substrate, a metabolite, a transition state analogue, a co-factor, an inhibitor, a drug, a dye, a nutrient, a growth factor, a cell, a tissue, angiotensin converting enzyme, renin, cyclooxygenase, 5-lipoxygenase, IL-10 converting enzyme, cytokine receptors, PDGF receptor, type II inosine monophosphate dehydrogenase, $\beta$-lactamases, fungal cytochrome P-450, bradykinin, neutrophil elastase, HIV proteins, such as tat, rev, gag, int, RT, nucleocapsid, VEGF, bFGF, TGF$\beta$, KGF, PDGF, thrombin, theophylline, caffeine, substance P, IgE, sPLA2, red blood cells, glioblastomas, fibrin clots, PBMCs, hCG, lectins, selectins, cytokines, ICP4 and complement proteins.

Another embodiment of the invention relates to a use of a library of secondary antigens, such as peptides, or nucleic acid molecules encoding such peptides, in the generation of a library of antibodies having been raised by one or more primary antigens, wherein said primary and secondary antigens are not identical.

In another embodiment at least one amino acid residue of said peptides is of the formula

—(NH)—(H—Cα-R1)-(C=O)— wherein N, Cα and C are connected to form the backbone of a peptide bond and R1 is preferably selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and
unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and
unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl, aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl,
substituted and unsubstituted aminoalkyl, substituted and unsubstituted alkylaminoalkyl, amidino,
cyanoamidino,
substituted and unsubstituted heterocyclicalkyl,
substituted and unsubstituted aralkyl,
substituted and unsubstituted cycloalkyl,
substituted and unsubstituted cycloalkenyl,
substituted and unsubstituted alkylthio,
substituted and unsubstituted alkylsulfinyl,
substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl,
acyl, acylamino,
substituted and unsubstituted arylthio, substituted and unsubstituted aralkylthio,
substituted and unsubstituted aryloxy, substituted and unsubstituted aralkoxy,
substituted and unsubstituted haloalkyl,
substituted and unsubstituted carboxyhaloalkyl,
substituted and unsubstituted alkoxycarbonylhaloalkyl, substituted and unsubstituted aminocarbonylhaloalkyl, substituted and unsubstituted alkylaminocarbonylhaloalkyl,
substituted and unsubstituted alkoxycarbonylcyanoalkenyl,
substituted and unsubstituted carboxyalkylaminocarbonyl,
substituted and unsubstituted aralkoxycarbonylalkylaminocarbonyl,
substituted and unsubstituted cycloalkylalkyl, and
substituted and unsubstituted aralkenyl.

In another embodiment at least one amino acid residue of said peptides is of the formula

—(NH)—(H—Cα-R1)-(C=O)— wherein N, Cα and C are connected to form the backbone of a peptide bond and R1 is preferably selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy, substituted and unsubstituted alkoxyalkyl, substituted and unsubstituted haloalkoxy, substituted and unsubstituted haloalkoxyalkyl,
substituted and unsubstituted aryl,
substituted and unsubstituted heterocyclic,
substituted and unsubstituted heteroaryl,
sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-N-arylaminosulfonyl,
carboxy, substituted and unsubstituted carboxyalkyl,
carbonyl, substituted and unsubstituted alkylcarbonyl, substituted and unsubstituted alkylcarbonylalkyl,
substituted and unsubstituted alkoxycarbonyl, substituted and unsubstituted alkoxycarbonylalkyl, aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl, substituted and unsubstituted aminoalkyl, substituted and unsubstituted alkylaminoalkyl, amidino, cyanoamidino, substituted and unsubstituted heterocyclicalkyl, substituted and unsubstituted aralkyl, substituted and unsubstituted cycloalkyl, substituted and unsubstituted cycloalkenyl, substituted and unsubstituted alkylthio, substituted and unsubstituted alkylsulfinyl, substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkylaminoalkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

Yet another embodiment of the invention relates to a method for obtaining, from a plurality of different IgY antibodies specific for one or more primary antigens, one or more IgY antibodies, but not all of said plurality of IgY antibodies, wherein said isolated IgY antibodies are also specific for one or more secondary antigens, said method comprising the steps of i) generating a plurality of IgY antibodies by immunizing each of a plurality of avian organisms of the same or different species with a composition comprising a plurality of different first antigens, thereby generating a plurality of different IgY antibodies, ii) providing one or more secondary antigen(s) to be tested, iii) contacting said one or more secondary antigen(s) with the plurality of different IgY antibodies specific for one or more primary antigens as generated in step i), and iv) obtaining one or more IgY antibodies having a specificity for both one or more of said primary antigens and one or more of said secondary antigens, v) wherein the primary and secondary antigens are identical, and vi) wherein the obtained IgY antibodies specific for said one or more secondary antigens have been raised against said one or more primary antigens only.

In another embodiment said where said secondary antigen is as defined as in any of the previous embodiments and used for harvesting IgY antibodies from the library generate by the method described herein.

In another embodiment generated IgY antibodies from the library are harvested using said secondary antigen, which comprise one or more peptide(s).

In another embodiment the length of consecutively linked amino acid residues in respectively primary and secondary antigen differ in number of incorporated moieties such as in the range of from 1 amino acid residues to preferably less than 10000 amino acid residues, such as from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, for example from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, such as from 1 to less than 5000 amino acid residues, for example from 1 to less than 1000 amino acid residues, such as from 1 to less than 900 amino acid residues, for example from 1 to less than 800 amino acid residues, such as from 1 to less than 700 amino acid residues, for example from 1 to less than 600 amino acid residues, such as from 1 to less than 500 amino acid residues, for example from 1 to less than 400 amino acid residues, such as from 1 to less than 300 amino acid residues, for example from 1 to less than 200 amino acid residues, such as from 1 to less than 100 amino acid residues, for example from 1 to less than 90 amino acid residues, such as from 1 to less than 80 amino acid residues, for example from 1 to less than 70 amino acid residues, such as from 1 to less than 60 amino acid residues, for example from 1 to less than 50 amino acid residues, such as from 1 to less than 40 amino acid residues, for example from 1 to less than 35 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 30 amino acid residues, for example from 1 to less than 29 amino acid residues, such as from 1 to less than 28 amino acid residues, for example from 1 to less than 27 amino acid residues, such as from 1 to less than 26 amino acid residues, for example from 1 to less than 25 amino acid residues, such as from 1 to less than 24 amino acid residues, for example from 1 to less than 23 amino acid residues, such as from 1 to less than 22 amino acid residues, for example from 1 to less than 21 amino acid residues, such as from 1 to less than 20 amino acid residues, for example from 1 to less than 19 amino acid residues, such as from 1 to less than 18 amino acid residues, for example from 1 to less than 17 amino acid residues, such as from 1 to less than 16 amino acid residues, for example from 1 to less than 15 amino acid residues, such as from 1 to less than 14 amino acid residues, for example from 1 to less than 13 amino acid residues, such as from 1 to less than 12 amino acid residues, for example from 1 to less than 11 amino acid residues, such as from 1 to less than 10 amino acid residues, for example from 1 to less than 9 amino acid residues, such as from 1 to less than 8 amino acid residues, for example from 1 to less than 7 amino acid residues, such as from 1 to less than 6 amino acid residues, for example from 1 to less than 5 amino acid residues, such as from 1 to less than 4 amino acid residues, for example from 1 to less than 3 amino acid residues, such as from 1 to less than 2 amino acid residues, for example from 2 to less than 5000 amino acid residues, for example from 2 to less than 1000 amino acid residues, such as from 2 to less than 900 amino acid residues, for example from 2 to less than 800 amino acid residues, such as from 2 to less than 700 amino acid residues, for example from 2 to less than 600 amino acid residues, such as from 2 to less than 500 amino acid residues, for example from 2 to less than 400 amino acid residues, such as from 2 to less than 300 amino acid residues, for example from 2 to less than 200 amino acid residues, such as from 2 to less than 100 amino acid residues, for example from 2 to less than 90 amino acid residues, such as from 2 to less than 80 amino acid residues, for example from 2 to less than 70 amino acid residues, such as from 2 to less than 60 amino acid residues, for example from 2 to less than 50 amino acid residues, such as from 2 to less than 40 amino acid residues, for example from 2 to less than 35 amino acid residues, such as from 2 to less than 30 amino acid residues, for example from 2 to less than 29 amino acid residues, such as from 2 to less than 28 amino acid residues, for example from 2 to less than 27 amino acid residues, such as from 2 to less than 26 amino acid residues, for example from 2 to less than 25 amino acid residues, such as from 2 to less than 24 amino acid residues, for example from 2 to less than 23 amino acid residues, such as from 2 to less than 22 amino acid residues, for example from 2 to less than 21 amino acid residues, such as from 2 to less than 30 amino acid residues, for example from 2 to less than 29 amino acid residues, such as from 2 to less than 28 amino acid residues, for example from 2 to less than 27 amino acid residues, such as from 2 to less than 26 amino acid residues, for example from 2 to less than 25 amino acid residues, such as from 2 to less than 24 amino acid residues, for example from 2 to less than 23 amino acid residues, such as from 2 to less than 22 amino acid residues, for example from 2 to less than 21 amino acid residues, such as from 2 to less than 20 amino acid residues, for example from 2 to less than 19 amino acid residues, such as from 2 to less than 18 amino acid residues, for example from 2 to less than 17 amino acid residues, such as from 2 to less than 16 amino acid residues, for example from 2 to less than 15 amino acid residues, such as from 2 to less than 14 amino acid residues, for example from 2 to less than 13 amino acid residues, such as from 2 to less than 12 amino acid residues, for example from 2 to less than 11 amino acid residues, such as from 2 to less than 10 amino acid residues, such as from 3 to less than 5000 amino acid residues, for example from 3 to less than 1000 amino acid residues, such as from 3 to less than 900 amino acid residues, for example from 3 to less than 800 amino acid residues, such as from 3 to less than 700 amino acid residues, for example from 3 to less than 600 amino acid residues, such as from 3 to less than 500 amino acid residues, for example from 3 to less than 400 amino acid residues, such as from 3 to less than 300 amino acid residues, for example from 3 to less than 200 amino acid residues, such as from 3 to less than 100 amino acid residues, for example from 3 to less than 90 amino acid residues, such as from 3 to less than 80 amino acid residues, for example from 3 to less than 70 amino acid residues, such as from 3 to less than 60 amino acid residues, for example from 3 to less than 50 amino acid residues, such as from 3 to less than 40 amino acid residues, for example from 3 to less than 35 amino acid residues, such as from 3 to less than 30 amino acid residues, for example from 3 to less than 29 amino acid residues, such as from 3 to less than 28 amino acid residues, for example from 3 to less than 27 amino acid residues, such as from 3 to less than 26 amino acid residues, for example from 3 to less than 25 amino acid residues, such as from 3 to less than 24 amino acid residues, for example from 3 to less than 23 amino acid residues, such as from 3 to less than 22 amino acid residues, for example from 3 to less than 21 amino acid residues, such as from 3 to less than 30 amino acid residues, for example from 3 to less than 29 amino acid residues, such as from 3 to less than 28 amino acid residues, for example from 3 to less than 27 amino acid residues, such as from 3 to less than 26 amino acid residues, for example from 3 to less than 25 amino acid residues, such as from 3 to less than 24 amino acid residues, for example from 3 to less than 23 amino acid residues, such as from 3 to less than 22 amino acid residues, for example from 3 to less than 21 amino acid residues, such as from 3 to less than 20 amino acid residues, for example from 3 to less than 19 amino acid residues, such as from 3 to less than 18 amino acid residues, for example from 3 to less than 17 amino acid residues, such as from 3 to less than 16 amino acid residues, for example from 3 to less than 15 amino acid residues, such as from 3 to less than 14 amino acid residues, for example from 3 to less than 13 amino acid residues, such as from 3 to less than 12 amino acid residues, for example from 3 to less than 11 amino acid residues, such as from 4 to less than 5000 amino acid residues, for example from 4 to less than 1000 amino acid residues, such as from 4 to less than 900 amino acid residues, for example from 4 to less than 800 amino acid residues, such as from 4 to less than 700 amino acid residues, for example from 4 to less than 600 amino acid residues, such as from 4 to less than 500 amino acid residues, for example from 4 to less than 400 amino acid residues, such as from 4 to less than 300 amino acid residues, for example from 4 to less than 200 amino acid residues, such as from 4 to less than 100 amino acid residues, for example from 4 to less than 90 amino acid residues, such as from 4 to less than 80 amino acid residues, for example from 4 to less than 70 amino acid residues, such as from 4 to less than 60 amino acid residues, for example from 4 to less than 50 amino acid residues, such as from 4 to less than 40 amino acid residues, for example from 4 to less than 35 amino acid residues, such as from 4 to less than 30 amino acid residues, for example from 4 to less than 29 amino acid residues, such as from 4 to less than 28 amino acid residues, for example from 4 to less than 27 amino acid residues, such as from 4 to less than 26 amino acid residues, for example from 4 to less than 25 amino acid residues, such as from 4 to less than 24 amino acid residues, for example from 4 to less than 23 amino acid residues, such as from 4 to less than 22 amino acid residues, for example from 4 to less than 21 amino acid residues, such as from 4 to less than 30 amino acid residues, for example from 4 to less than 29 amino acid residues, such as from 4 to less than 28 amino acid residues, for example from 4 to less than 27 amino acid residues, such as from 4 to less than 26 amino acid residues, for example from 4 to less than 25 amino acid residues, such as from 4 to less than 24 amino acid residues, for example from 4 to less than 23 amino acid residues, such as from 4 to less than 22 amino acid residues, for example from 4 to less than 21 amino acid residues, such as from 4 to less than 20 amino acid residues, for example from 4 to less than 19 amino acid residues, such as from 4 to less than 18 amino acid residues, for example from 4 to less than 17 amino acid residues, such as from 4 to less than 16 amino acid residues, for example from 4 to less than 15 amino acid residues, such as from 4 to less than 14 amino acid residues, for example from 4 to less than 13 amino acid residues, such as from 4 to less than 12 amino acid residues, for example from 4 to less than 11 amino acid residues, such as from 5 to less than 5000 amino acid residues, for example from 5 to less than 1000 amino acid residues, such as from 5 to less than 900 amino acid residues, for example from 5 to less than 800 amino acid residues, such as from 5 to less than 700 amino acid residues, for example from 5 to less than 600 amino acid residues, such as from 5 to less than 500 amino acid residues, for example from 5 to less than 400 amino acid residues, such as from 5 to less than 300 amino acid residues, for example from 5 to less than 200 amino acid residues, such as from 5 to less than 100 amino acid residues, for example from 5 to less than 90 amino acid residues, such as from 5 to less than 80 amino acid residues, for example from 5 to less than 70 amino acid residues, such as from 5 to less than 60 amino acid residues, for example from 5 to less than 50 amino acid residues, such as from 5 to less than 40 amino acid residues, for example from 5 to less than 35 amino acid residues, such as from 5 to less than 30 amino acid residues, for example from 5 to less than 29 amino acid residues, such as from 5 to less than 28 amino acid residues, for example from 5 to less than 27 amino acid residues, such as from 5 to less than 26 amino acid residues, for example from 5 to less than 25 amino acid residues, such as from 5 to less than 24 amino acid residues, for example from 5 to less than 23 amino acid residues, such as from 5 to less than 22 amino acid residues, for example from 5 to less than 21 amino acid residues, such as from 5 to less than 30 amino acid residues, for example from 5 to less than 29 amino acid residues, such as from 5 to less than 28 amino acid residues, for example from 5 to less than 27 amino acid residues, such as from 5 to less than 26 amino acid residues, for example from 5 to less than 25 amino acid residues, such as from 5 to less than 24 amino acid residues, for example from 5 to less than 23 amino acid residues, such as from 5 to less than 22 amino acid residues, for example from 5 to less than 21 amino acid residues, such as from 5 to less than 20 amino acid residues, for example from 5 to less than 19 amino acid residues, such as from 5 to less than 18 amino acid residues, for example from 5 to less than 17 amino acid residues, such as from 5 to less than 16 amino acid residues, for example from 5 to less than 15 amino acid residues, such as from 5 to less than 14 amino acid residues, for example from 5 to less than 13 amino acid residues, such as from 5 to less than 12 amino acid residues, for example from 5 to less than 11 amino acid residues, such as from 6 to less than 5000 amino acid residues, for example from 6 to less than 1000 amino acid residues, such as from 6 to less than 900 amino acid residues, for example from 6 to less than 800 amino acid residues, such as from 6 to less than 700 amino acid residues, for example from 6 to less than 600 amino acid residues, such as from 6 to less than 500 amino acid residues, for example from 6 to less than 400 amino acid residues, such as from 6 to less than 300 amino acid residues, for example from 6 to less than 200 amino acid residues, such as from 6 to less than 100 amino acid residues, for example from 6 to less than 90 amino acid residues, such as from 6 to less than 80 amino acid residues, for example from 6 to less than 70 amino acid residues, such as from 6 to less than 60 amino acid residues, for example from 6 to less than 50 amino acid residues, such as from 6 to less than 40 amino acid residues, for example from 6 to less than 35 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 30 amino acid residues, for example from 6 to less than 29 amino acid residues, such as from 6 to less than 28 amino acid residues, for example from 6 to less than 27 amino acid residues, such as from 6 to less than 26 amino acid residues, for example from 6 to less than 25 amino acid residues, such as from 6 to less than 24 amino acid residues, for example from 6 to less than 23 amino acid residues, such as from 6 to less than 22 amino acid residues, for example from 6 to less than 21 amino acid residues, such as from 6 to less than 20 amino acid residues, for example from 6 to less than 19 amino acid residues, such as from 6 to less than 18 amino acid residues, for example from 6 to less than 17 amino acid residues, such as from 6 to less than 16 amino acid residues, for example from 6 to less than 15 amino acid residues, such as from 6 to less than 14 amino acid residues, for example from 6 to less than 13 amino acid residues, such as from 6 to less than 12 amino acid residues, for example from 6 to less than 11 amino acid residues, such as from 7 to less than 5000 amino acid residues, for example from 7 to less than 1000 amino acid residues, such as from 7 to less than 900 amino acid residues, for example from 7 to less than 800 amino acid residues, such as from 7 to less than 700 amino acid residues, for example from 7 to less than 600 amino acid residues, such as from 7 to less than 500 amino acid residues, for example from 7 to less than 400 amino acid residues, such as from 7 to less than 300 amino acid residues, for example from 7 to less than 200 amino acid residues, such as from 7 to less than 100 amino acid residues, for example from 7 to less than 90 amino acid residues, such as from 7 to less than 80 amino acid residues, for example from 7 to less than 70 amino acid residues, such as from 7 to less than 60 amino acid residues, for example from 7 to less than 50 amino acid residues, such as from 7 to less than 40 amino acid residues, for example from 7 to less than 35 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 30 amino acid residues, for example from 7 to less than 29 amino acid residues, such as from 7 to less than 28 amino acid residues, for example from 7 to less than 27 amino acid residues, such as from 7 to less than 26 amino acid residues, for example from 7 to less than 25 amino acid residues, such as from 7 to less than 24 amino acid residues, for example from 7 to less than 23 amino acid residues, such as from 7 to less than 22 amino acid residues, for example from 7 to less than 21 amino acid residues, such as from 7 to less than 20 amino acid residues, for example from 7 to less than 19 amino acid residues, such as from 7 to less than 18 amino acid residues, for example from 7 to less than 17 amino acid residues, such as from 7 to less than 16 amino acid residues, for example from 7 to less than 15 amino acid residues, such as from 7 to less than 14 amino acid residues, for example from 7 to less than 13 amino acid residues, such as from 7 to less than 12 amino acid residues, for example from 7 to less than 11 amino acid residues, such as from 8 to less than 5000 amino acid residues, for example from 8 to less than 1000 amino acid residues, such as from 8 to less than 900 amino acid residues, for example from 8 to less than 800 amino acid residues, such as from 8 to less than 700 amino acid residues, for example from 8 to less than 600 amino acid residues, such as from 8 to less than 500 amino acid residues, for example from 8 to less than 400 amino acid residues, such as from 8 to less than 300 amino acid residues, for example from 8 to less than 200 amino acid residues, such as from 8 to less than 100 amino acid residues, for example from 8 to less than 90 amino acid residues, such as from 8 to less than 80 amino acid residues, for example from 8 to less than 70 amino acid residues, such as from 8 to less than 60 amino acid residues, for example from 8 to less than 50 amino acid residues, such as from 8 to less than 40 amino acid residues, for example from 8 to less than 35 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 30 amino acid residues, for example from 8 to less than 29 amino acid residues, such as from 8 to less than 28 amino acid residues, for example from 8 to less than 27 amino acid residues, such as from 8 to less than 26 amino acid residues, for example from 8 to less than 25 amino acid residues, such as from 8 to less than 24 amino acid residues, for example from 8 to less than 23 amino acid residues, such as from 8 to less than 22 amino acid residues, for example from 8 to less than 21 amino acid residues, such as from 8 to less than 20 amino acid residues, for example from 8 to less than 19 amino acid residues, such as from 8 to less than 18 amino acid residues, for example from 8 to less than 17 amino acid residues, such as from 8 to less than 16 amino acid residues, for example from 8 to less than 15 amino acid residues, such as from 8 to less than 14 amino acid residues, for example from 8 to less than 13 amino acid residues, such as from 8 to less than 12 amino acid residues, for example from 8 to less than 11 amino acid residues, such as from 9 to less than 5000 amino acid residues, for example from 9 to less than 1000 amino acid residues, such as from 9 to less than 900 amino acid residues, for example from 9 to less than 800 amino acid residues, such as from 9 to less than 700 amino acid residues, for example from 9 to less than 600 amino acid residues, such as from 9 to less than 500 amino acid residues, for example from 9 to less than 400 amino acid residues, such as from 9 to less than 300 amino acid residues, for example from 9 to less than 200 amino acid residues, such as from 9 to less than 100 amino acid residues, for example from 9 to less than 90 amino acid residues, such as from 9 to less than 80 amino acid residues, for example from 9 to less than 70 amino acid residues, such as from 9 to less than 60 amino acid residues, for example from 9 to less than 50 amino acid residues, such as from 9 to less than 40 amino acid residues, for example from 9 to less than 35 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 30 amino acid residues, for example from 9 to less than 29 amino acid residues, such as from 9 to less than 28 amino acid residues, for example from 9 to less than 27 amino acid residues, such as from 9 to less than 26 amino acid residues, for example from 9 to less than 25 amino acid residues, such as from 9 to less than 24 amino acid residues, for example from 9 to less than 23 amino acid residues, such as from 9 to less than 22 amino acid residues, for example from 9 to less than 21 amino acid residues, such as from 9 to less than 20 amino acid residues, for example from 9 to less than 19 amino acid residues, such as from 9 to less than 18 amino acid residues, for example from 9 to less than 17 amino acid residues, such as from 9 to less than 16 amino acid residues, for example from 9 to less than 15 amino acid residues, such as from 9 to less than 14 amino acid residues, for example from 9 to less than 13 amino acid residues, such as from 9 to less than 12 amino acid residues, for example from 9 to less than 11 amino acid residues, such as from 10 to less than 5000 amino acid residues, for example from 10 to less than 1000 amino acid residues, such as from 10 to less than 900 amino acid residues, for example from 10 to less than 800 amino acid residues, such as from 10 to less than 700 amino acid residues, for example from 10 to less than 600 amino acid residues, such as from 10 to less than 500 amino acid residues, for example from 10 to less than 400 amino acid residues, such as from 10 to less than 300 amino acid residues, for example from 10 to less than 200 amino acid residues, such as from 10 to less than 100 amino acid residues, for example from 10 to less than 90 amino acid residues, such as from 10 to less than 80 amino acid residues, for example from 10 to less than 70 amino acid residues, such as from 10 to less than 60 amino acid residues, for example from 10 to less than 50 amino acid residues, such as from 10 to less than 40 amino acid residues, for example from 10 to less than 35 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 30 amino acid residues, for example from 10 to less than 29 amino acid residues, such as from 10 to less than 28 amino acid residues, for example from 10 to less than 27 amino acid residues, such as from 10 to less than 26 amino acid residues, for example from 10 to less than 25 amino acid residues, such as from 10 to less than 24 amino acid residues, for example from 10 to less than 23 amino acid residues, such as from 10 to less than 22 amino acid residues, for example from 10 to less than 21 amino acid residues, such as from 10 to less than 20 amino acid residues, for example from 10 to less than 19 amino acid residues, such as from 10 to less than 18 amino acid residues, for example from 10 to less than 17 amino acid residues, such as from 10 to less than 16 amino acid residues, for example from 10 to less than 15 amino acid residues, such as from 10 to less than 14 amino acid residues, for example from 10 to less than 13 amino acid residues, such as from 10 to less than 12 amino acid residues, such as from 11 to less than 5000 amino acid residues, for example from 11 to less than 1000 amino acid residues, such as from 11 to less than 900 amino acid residues, for example from 11 to less than 800 amino acid residues, such as from 11 to less than 700 amino acid residues, for example from 11 to less than 600 amino acid residues, such as from 11 to less than 500 amino acid residues, for example from 11 to less than 400 amino acid residues, such as from 11 to less than 300 amino acid residues, for example from 11 to less than 200 amino acid residues, such as from 11 to less than 100 amino acid residues, for example from 11 to less than 90 amino acid residues, such as from 11 to less than 80 amino acid residues, for example from 11 to less than 70 amino acid residues, such as from 11 to less than 60 amino acid residues, for example from 11 to less than 50 amino acid residues, such as from 11 to less than 40 amino acid residues, for example from 11 to less than 35 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 30 amino acid residues, for example from 11 to less than 29 amino acid residues, such as from 11 to less than 28 amino acid residues, for example from 11 to less than 27 amino acid residues, such as from 11 to less than 26 amino acid residues, for example from 11 to less than 25 amino acid residues, such as from 11 to less than 24 amino acid residues, for example from 11 to less than 23 amino acid residues, such as from 11 to less than 22 amino acid residues, for example from 11 to less than 21 amino acid residues, such as from 11 to less than 20 amino acid residues, for example from 11 to less than 19 amino acid residues, such as from 11 to less than 18 amino acid residues, for example from 11 to less than 17 amino acid residues, such as from 11 to less than 16 amino acid residues, for example from 11 to less than 15 amino acid residues, such as from 11 to less than 14 amino acid residues, for example from 11 to less than 13 amino acid residues, such as from 12 to less than 5000 amino acid residues, for example from 12 to less than 1000 amino acid residues, such as from 12 to less than 900 amino acid residues, for example from 12 to less than 800 amino acid residues, such as from 12 to less than 700 amino acid residues, for example from 12 to less than 600 amino acid residues, such as from 12 to less than 500 amino acid residues, for example from 12 to less than 400 amino acid residues, such as from 12 to less than 300 amino acid residues, for example from 12 to less than 200 amino acid residues, such as from 12 to less than 100 amino acid residues, for example from 12 to less than 90 amino acid residues, such as from 12 to less than 80 amino acid residues, for example from 12 to less than 70 amino acid residues, such as from 12 to less than 60 amino acid residues, for example from 12 to less than 50 amino acid residues, such as from 12 to less than 40 amino acid residues, for example from 12 to less than 35 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 30 amino acid residues, for example from 12 to less than 29 amino acid residues, such as from 12 to less than 28 amino acid residues, for example from 12 to less than 27 amino acid residues, such as from 12 to less than 26 amino acid residues, for example from 12 to less than 25 amino acid residues, such as from 12 to less than 24 amino acid residues, for example from 12 to less than 23 amino acid residues, such as from 12 to less than 22 amino acid residues, for example from 12 to less than 21 amino acid residues, such as from 12 to less than 20 amino acid residues, for example from 12 to less than 19 amino acid residues, such as from 12 to less than 18 amino acid residues, for example from 12 to less than 17 amino acid residues, such as from 12 to less than 16 amino acid residues, for example from 12 to less than 15 amino acid residues, such as from 12 to less than 14 amino acid residues, such as from 13 to less than 5000 amino acid residues, for example from 13 to less than 1000 amino acid residues, such as from 13 to less than 900 amino acid residues, for example from 13 to less than 800 amino acid residues, such as from 13 to less than 700 amino acid residues, for example from 13 to less than 600 amino acid residues, such as from 13 to less than 500 amino acid residues, for example from 13 to less than 400 amino acid residues, such as from 13 to less than 300 amino acid residues, for example from 13 to less than 200 amino acid residues, such as from 13 to less than 100 amino acid residues, for example from 13 to less than 90 amino acid residues, such as from 13 to less than 80 amino acid residues, for example from 13 to less than 70 amino acid residues, such as from 13 to less than 60 amino acid residues, for example from 13 to less than 50 amino acid residues, such as from 13 to less than 40 amino acid residues, for example from 13 to less than 35 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 30 amino acid residues, for example from 13 to less than 29 amino acid residues, such as from 13 to less than 28 amino acid residues, for example from 13 to less than 27 amino acid residues, such as from 13 to less than 26 amino acid residues, for example from 13 to less than 25 amino acid residues, such as from 13 to less than 24 amino acid residues, for example from 13 to less than 23 amino acid residues, such as from 13 to less than 22 amino acid residues, for example from 13 to less than 21 amino acid residues, such as from 13 to less than 20 amino acid residues, for example from 13 to less than 19 amino acid residues, such as from 13 to less than 18 amino acid residues, for example from 13 to less than 17 amino acid residues, such as from 13 to less than 16 amino acid residues, for example from 13 to less than 15 amino acid residues, such as from 14 to less than 5000 amino acid residues, for example from 14 to less than 1000 amino acid residues, such as from 14 to less than 900 amino acid residues, for example from 14 to less than 800 amino acid residues, such as from 14 to less than 700 amino acid residues, for example from 14 to less than 600 amino acid residues, such as from 14 to less than 500 amino acid residues, for example from 14 to less than 400 amino acid residues, such as from 14 to less than 300 amino acid residues, for example from 14 to less than 200 amino acid residues, such as from 14 to less than 100 amino acid residues, for example from 14 to less than 90 amino acid residues, such as from 14 to less than 80 amino acid residues, for example from 14 to less than 70 amino acid residues, such as from 14 to less than 60 amino acid residues, for example from 14 to less than 50 amino acid residues, such as from 14 to less than 40 amino acid residues, for example from 14 to less than 35 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 30 amino acid residues, for example from 14 to less than 29 amino acid residues, such as from 14 to less than 28 amino acid residues, for example from 14 to less than 27 amino acid residues, such as from 14 to less than 26 amino acid residues, for example from 14 to less than 25 amino acid residues, such as from 14 to less than 24 amino acid residues, for example from 14 to less than 23 amino acid residues, such as from 14 to less than 22 amino acid residues, for example from 14 to less than 21 amino acid residues, such as from 14 to less than 20 amino acid residues, for example from 14 to less than 19 amino acid residues, such as from 14 to less than 18 amino acid residues, for example from 14 to less than 17 amino acid residues, such as from 14 to less than 16 amino acid residues, such as from 15 to less than 5000 amino acid residues, for example from 15 to less than 1000 amino acid residues, such as from 15 to less than 900 amino acid residues, for example from 15 to less than 800 amino acid residues, such as from 15 to less than 700 amino acid residues, for example from 15 to less than 600 amino acid residues, such as from 15 to less than 500 amino acid residues, for example from 15 to less than 400 amino acid residues, such as from 15 to less than 300 amino acid residues, for example from 15 to less than 200 amino acid residues, such as from 15 to less than 100 amino acid residues, for example from 15 to less than 90 amino acid residues, such as from 15 to less than 80 amino acid residues, for example from 15 to less than 70 amino acid residues, such as from 15 to less than 60 amino acid residues, for example from 15 to less than 50 amino acid residues, such as from 15 to less than 40 amino acid residues, for example from 15 to less than 35 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 30 amino acid residues, for example from 15 to less than 29 amino acid residues, such as from 15 to less than 28 amino acid residues, for example from 15 to less than 27 amino acid residues, such as from 15 to less than 26 amino acid residues, for example from 15 to less than 25 amino acid residues, such as from 15 to less than 24 amino acid residues, for example from 15 to less than 23 amino acid residues, such as from 15 to less than 22 amino acid residues, for example from 15 to less than 21 amino acid residues, such as from 15 to less than 20 amino acid residues, for example from 15 to less than 19 amino acid residues, such as from 15 to less than 18 amino acid residues, for example from 15 to less than 17 amino acid residues, such as from 16 to less than 5000 amino acid residues, for example from 16 to less than 1000 amino acid residues, such as from 16 to less than 900 amino acid residues, for example from 16 to less than 800 amino acid residues, such as from 16 to less than 700 amino acid residues, for example from 16 to less than 600 amino acid residues, such as from 16 to less than 500 amino acid residues, for example from 16 to less than 400 amino acid residues, such as from 16 to less than 300 amino acid residues, for example from 16 to less than 200 amino acid residues, such as from 16 to less than 100 amino acid residues, for example from 16 to less than 90 amino acid residues, such as from 16 to less than 80 amino acid residues, for example from 16 to less than 70 amino acid residues, such as from 16 to less than 60 amino acid residues, for example from 16 to less than 50 amino acid residues, such as from 16 to less than 40 amino acid residues, for example from 16 to less than 35 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 30 amino acid residues, for example from 16 to less than 29 amino acid residues, such as from 16 to less than 28 amino acid residues, for example from 16 to less than 27 amino acid residues, such as from 16 to less than 26 amino acid residues, for example from 16 to less than 25 amino acid residues, such as from 16 to less than 24 amino acid residues, for example from 16 to less than 23 amino acid residues, such as from 16 to less than 22 amino acid residues, for example from 16 to less than 21 amino acid residues, such as from 16 to less than 20 amino acid residues, for example from 16 to less than 19 amino acid residues, such as from 16 to less than 18 amino acid residues, such as from 17 to less than 5000 amino acid residues, for example from 17 to less than 1000 amino acid residues, such as from 17 to less than 900 amino acid residues, for example from 17 to less than 800 amino acid residues, such as from 17 to less than 700 amino acid residues, for example from 17 to less than 600 amino acid residues, such as from 17 to less than 500 amino acid residues, for example from 17 to less than 400 amino acid residues, such as from 17 to less than 300 amino acid residues, for example from 17 to less than 200 amino acid residues, such as from 17 to less than 100 amino acid residues, for example from 17 to less than 90 amino acid residues, such as from 17 to less than 80 amino acid residues, for example from 17 to less than 70 amino acid residues, such as from 17 to less than 60 amino acid residues, for example from 17 to less than 50 amino acid residues, such as from 17 to less than 40 amino acid residues, for example from 17 to less than 35 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 30 amino acid residues, for example from 17 to less than 29 amino acid residues, such as from 17 to less than 28 amino acid residues, for example from 17 to less than 27 amino acid residues, such as from 17 to less than 26 amino acid residues, for example from 17 to less than 25 amino acid residues, such as from 17 to less than 24 amino acid residues, for example from 17 to less than 23 amino acid residues, such as from 17 to less than 22 amino acid residues, for example from 17 to less than 21 amino acid residues, such as from 17 to less than 20 amino acid residues, for example from 17 to less than 19 amino acid residues, such as from 18 to less than 5000 amino acid residues, for example from 18 to less than 1000 amino acid residues, such as from 18 to less than 900 amino acid residues, for example from 18 to less than 800 amino acid residues, such as from 18 to less than 700 amino acid residues, for example from 18 to less than 600 amino acid residues, such as from 18 to less than 500 amino acid residues, for example from 18 to less than 400 amino acid residues, such as from 18 to less than 300 amino acid residues, for example from 18 to less than 200 amino acid residues, such as from 18 to less than 100 amino acid residues, for example from 18 to less than 90 amino acid residues, such as from 18 to less than 80 amino acid residues, for example from 18 to less than 70 amino acid residues, such as from 18 to less than 60 amino acid residues, for example from 18 to less than 50 amino acid residues, such as from 18 to less than 40 amino acid residues, for example from 18 to less than 35 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 30 amino acid residues, for example from 18 to less than 29 amino acid residues, such as from 18 to less than 28 amino acid residues, for example from 18 to less than 27 amino acid residues, such as from 18 to less than 26 amino acid residues, for example from 18 to less than 25 amino acid residues, such as from 18 to less than 24 amino acid residues, for example from 18 to less than 23 amino acid residues, such as from 18 to less than 22 amino acid residues, for example from 18 to less than 21 amino acid residues, such as from 18 to less than 20 amino acid residues, such as from 19 to less than 5000 amino acid residues, for example from 19 to less than 1000 amino acid residues, such as from 19 to less than 900 amino acid residues, for example from 19 to less than 800 amino acid residues, such as from 19 to less than 700 amino acid residues, for example from 19 to less than 600 amino acid residues, such as from 19 to less than 500 amino acid residues, for example from 19 to less than 400 amino acid residues, such as from 19 to less than 300 amino acid residues, for example from 19 to less than 200 amino acid residues, such as from 19 to less than 100 amino acid residues, for example from 19 to less than 90 amino acid residues, such as from 19 to less than 80 amino acid residues, for example from 19 to less than 70 amino acid residues, such as from 19 to less than 60 amino acid residues, for example from 19 to less than 50 amino acid residues, such as from 19 to less than 40 amino acid residues, for example from 19 to less than 35 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues, such as from 19 to less than 30 amino acid residues, for example from 19 to less than 29 amino acid residues, such as from 19 to less than 28 amino acid residues, for example from 19 to less than 27 amino acid residues, such as from 19 to less than 26 amino acid residues, for example from 19 to less than 25 amino acid residues, such as from 19 to less than 24 amino acid residues, for example from 19 to less than 23 amino acid residues, such as from 19 to less than 22 amino acid residues, for example from 19 to less than 21 amino acid residues.

In another embodiment the length of consecutively linked amino acid residues in respectively primary and secondary antigen differ in number of incorporated moieties such as in the range of from 1 amino acid residues to preferably less than 10000 amino acid residues.

In another embodiment the primary and secondary antigen differ in sequence identity as defined by any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85 and BLOSUM 90, all using default parameters.

In another embodiment any pair of amino acid residues, of respectively primary and secondary antigen differ in Kyte & Doolittle hydropathy index with +/−2.5 units of one another, for example with +/−2.3 units of one another, such as with +/−2.1 units of one another, for example with +/−2.0 units of one another, such as with +/−1.8 units of one another, for example with +/−1.6 units of one another, such as with +/−1.5 units of one another, for example with +/−1.4 units of one another, such as with +/−1.3 units of one another, for example with +/−1.2 units of one another, such as with +/−1.1 units of one another, for example with +/−1.0 units of one another, such as with +/−0.9 units of one another, for example with +/−0.8 units of one another, such as with +/−0.7 units of one another, for example with +/−0.6 units of one another, such as with +/−0.5 units of one another, for example with +/−0.4 units of one another, such as with +/−0.3 units of one another, for example with +/−0.25 units of one another, such as with +/−0.2 units of one another, where the hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

In another embodiment any pair of amino acid residues, of respectively primary and secondary antigen differ in Kyte & Doolittle hydropathy index with +/−2.5 units of one another.

In another embodiment the primary and secondary antigens may differ in secondary structure such as alpha-helices, 310-helices, π-helices, beta-strands, beta-sheets, beta-hairpins loops, N-terminal and C-terminal stretches of amino acids and loops connecting said secondary structure elements.

In another embodiment the secondary structure elements are of different size such as differing by 1.5 Å of each analogous secondary structure element of respectively primary and secondary antigen, for example differing by 3 Å of each analogous secondary structure element of respectively primary and secondary antigen, such as differing by 4 Å of each analogous secondary structure element of respectively primary and secondary antigen, for example differing by 5 Å of each analogous secondary structure element of respectively primary and secondary antigen, such as differing by 6 Å of each analogous secondary structure element of respectively primary and secondary antigen, for example differing by 7 Å of each analogous secondary structure element of respectively primary and secondary antigen, such as differing by 8 Å of each analogous secondary structure element of respectively primary and secondary antigen, for example differing by 9 Å of each analogous secondary structure element of respectively primary and secondary antigen, such as differing by 10 Å of each analogous secondary structure element of respectively primary and secondary antigen, for example differing by 15 Å of each analogous secondary structure element of respectively primary and secondary antigen, such as differing by 20 Å of each analogous secondary structure element of respectively primary and secondary antigen, for example differing by 25 Å of each analogous secondary structure element of respectively primary and secondary antigen, such as differing by 30 Å of each analogous secondary structure element of respectively primary and secondary antigen, for example differing by 35 Å of each analogous secondary structure element of respectively primary and secondary antigen, such as differing by 40 Å of each analogous secondary structure element of respectively primary and secondary antigen, for example differing by 45 Å of each analogous secondary structure element of respectively primary and secondary antigen, such as differing by 50 Å of each analogous secondary structure element of respectively primary and secondary antigen, for example differing by 55 Å of each analogous secondary structure element of respectively primary and secondary antigen, such as differing by 60 Å of each analogous secondary structure element of respectively primary and secondary antigen, for example differing by 65 Å of each analogous secondary structure element of respectively primary and secondary antigen, such as differing by 70 Å of each analogous secondary structure element of respectively primary and secondary antigen, for example differing by 75 Å of each analogous secondary structure element of respectively primary and secondary antigen, such as differing by 80 Å of each analogous secondary structure element of respectively primary and secondary antigen, for example differing by 85 Å of each analogous secondary structure element of respectively primary and secondary antigen, such as differing by 90 Å of each analogous secondary structure element of respectively primary and secondary antigen, for example differing by 95 Å of each analogous secondary structure element of respectively primary and secondary antigen, such as differing by 100 Å of each analogous secondary structure element of respectively primary and secondary antigen, for example differing by 200 Å of each analogous secondary structure element of respectively primary and secondary antigen, such as differing by 300 Å of each analogous secondary structure element of respectively primary and secondary antigen, for example differing by 400 Å of each analogous secondary structure element of respectively primary and secondary antigen, such as differing by 500 Å or more.

In another embodiment the secondary structure elements are of different size such as differing by 1.5 Å of each analogous secondary structure element of respectively primary and secondary antigen.

In another embodiment the primary and secondary antigens may differ in tertiary structure.

In another embodiment the primary and secondary antigens may differ in quaternary structure.

In another embodiment the primary and secondary antigens may differ in post-translational modification pattern such as acetylation (the addition of an acetyl group, usually at the N-terminus of the protein) and/or for example alkylation (the addition of an alkyl group (e.g. methyl, ethyl) and/or for example methylation (the addition of a methyl group, usually at lysine or arginine residues) and/or for example biotinylation (acylation of conserved lysine residues with a biotin appendage) and/or for example glutamylation (covalent linkage of glutamic acid residues to tubulin and some other proteins) and/or for example glycylation (covalent linkage of one to more than 40 glycine residues to the tubulin C-terminal tail) and/or for example glycosylation (the addition of a glycosyl group typically to either asparagine, hydroxylysine, serine, or threonine, resulting in a glycoprotein) and/or for example isoprenylation (the addition of an isoprenoid group e.g. farnesol and geranylgeraniol) and/or for example lipoylation (attachment of a lipoate functionality) and/or for example phosphopantetheinylation (the addition of a 4'-phosphopantetheinyl moiety from coenzyme A, as in fatty acid, polyketide, non-ribosomal peptide and leucine biosynthesis) and/or for example phosphorylation (the addition of a phosphate group to any residue, but typically to serine, tyrosine, threonine or histidine) and/or for example sulfation (the addition of a sulfate group to a tyrosine) and/or for example selenation and/or for example C-terminal amidation and/or for example phosphorylation and/or for example sulfation and/or for example glycosylation and/or for example amino acid conjugation and/or for example glutathione conjugation.

In another embodiment any peptide or peptide-like compound may comprise none, 1, 2, 3, 4, 5, 6, 7, 8, 9, 10, 11, 15, 20 or more modifications or any number herein between or above of said claim 74.

In another embodiment any peptide or peptide-like compound may comprise none, 1, 2, 3, 4, 5, 6, 7, 8, 9, 10, 11, 15, 20 or more modifications.

In another embodiment the difference between primary and secondary antigen include modifications by the addition of other proteins or peptides such as ISGylation (the covalent linkage to the ISG15 protein (Interferon-Stimulated Gene 15)) and/or SUMOylation (the covalent linkage to the SUMO protein (Small Ubiquitin-related MOdifier)) and/or ubiquitination (the covalent linkage to the protein ubiquitin).

In another embodiment the difference between primary and secondary antigen include modifications may involve a change of the chemical nature of amino acids, such as citrullination/deimination (the conversion of arginine to citrulline) and/or deamidation (the conversion of glutamine to glutamic acid or asparagine to aspartic acid).

In another embodiment the difference between primary and secondary antigen include modifications involving structural changes such as disulfide bridges (the covalent linkage of two cysteine amino acids) and/or proteolytic cleavage (cleavage of a protein at a peptide bond).

In another embodiment the primary and secondary antigen differ in domain composition such as comprising an □-peptide domain and/or a □-peptide domain and/or a □-peptide domain and/or an □-peptide domain and/or a mono-, di- or tri-substituted □-peptide domain and/or a mono-, di- or tri-substituted □-peptide domain, a and/or mono-, di- or tri-substituted □-peptide domain and/or a mono-, di- or tri-substituted □-peptide domain and/or a peptide domain wherein the amino acid residues are in the L-form and/or a peptide domain wherein the amino acid residues are in the D-form and/or a peptide domain wherein the amino acid residues are both in the L-form and in the D-form and/or a vinylogous peptide domain and/or a glyco-peptide domain and/or a vinylogous sulfonamide peptide domain and/or a polysulfonamide domain and/or a conjugated peptide domain and/or a conjugated peptide domain comprising one or more functional group(s), such as one or more prosthetic group(s).

In another embodiment said primary and secondary antigens may differ in peptide linkage by specific linkers forming di-, tri-, tetra-, penta-, hexa-, hepta-, octa-, nona- or deca-polypeptides or larger peptide polymers.

In another embodiment said primary and secondary antigens may differ in carrier, for example slowly metabolised macromolecules, such as polysaccharides, polylactic acids, polyglycolic acids, polymeric amino acids, amino acid copolymers, lipid aggregates (such as including oil droplets or and liposomes), inactive virus particles and or proteins such as including the keyhole limpet hemacyanin (KLH) and bovine serum albumin (BSA), ovalbumin (OVA), rabbit Serum Albumin (RSA) and CSA (Chicken Serum Albumin).

In another embodiment said primary and secondary antigens may differ in carrier, said carrier being selected from the group consisting of slowly metabolised macromolecules, polysaccharides, polylactic acids, polyglycolic acids, polymeric amino acids, amino acid copolymers, lipid aggregates (including oil droplets and liposomes), inactive virus particles and proteins including the keyhole limpet hemacyanin (KLH) and bovine serum albumin (BSA), ovalbumin (OVA), rabbit Serum Albumin (RSA) and CSA (Chicken Serum Albumin).

In another embodiment said primary and secondary antigens may differ in conjugation pattern such as being non-conjugated and conjugated respectively.

In another embodiment said conjugation comprises or consists of an oxidatively induced cross-link, such as mild oxidative induced cross-link catalysed by long-time exposure to atmospheric air such as an overnight exposure.

In another embodiment said conjugation comprises or consists of an oxidatively induced cross-link, including mild oxidative induced cross-link catalysed by long-time exposure to atmospheric air including an overnight exposure.

In another embodiment said conjugation comprises or consists of an oxidatively induced cross-link, including mild oxidative induced cross-link catalysed by or, a chemical cross-linking reagent selected from the group consisting of glutaraldehyde, charbodiimid and formaldehyde.

In another embodiment the methods described herein may be appearing singularly or repeatedly or in conjunction thereof or in combination with each other one or more times.

Yet another embodiment of the invention relates to an assay for testing the specificity of the plurality of different IgY antibodies by using a primary antigen as a secondary antigen comprising the steps of:

i) Immunizing an avian organism with a primary antigen.

ii) Generation of an antibody library according to claim 1.

iii) From said antibody library harvesting of IgY antibodies directed against the primary antigen used for immunization, by utilising a secondary antigen.

iv) Analysing the affinity of the harvested antigen:antibody complex.

In another embodiment one or more of the generated and harvested antibodies is utilised for targeting a specific epitope of a secondary antigen.

In another embodiment said targeted epitope is a part of a pathological entity or process of a mammalian organism.

Yet another embodiment of the invention relates to a method for treating a disease selected from the group consisting of enteric and gastrointestinal diseases, such as diarrhoea, dysentery, cholera and transmissible gastro enteritis in any mammalian organism, such as a human or animal species, said method comprising the steps of claim 1, thereby providing IgY antibodies specific for said one or more primary antigens and said one or more secondary antigens, and treating said disease by administering said IgY antibodies to an individual having contracted said disease, or being at risk of doing so unless treated prophylactically.

In another embodiment the animal species is selected from a pig and a cow.

In another embodiment said one or more secondary antigens used for the isolation of said one or more IgY antibodies is a marker for the disease in question.

In another embodiment the method comprises the further step of utilising said one or more IgY antibodies as an additive in a mouth rinse composition or in a tooth hygiene composition, such as a toothpaste for the prevention, treatment and/or control of plaque and related oral health problems.

In another embodiment said treatment involves treating *streptococcus mutans* serotype c infection in said individual.

In another embodiment said treatment involves treating individuals diagnosed as having cystic fibrosis, or having a prognosis for developing cystic fibrosis.

In another embodiment the method comprises the further step of utilising said one or more IgY antibodies as an additive in a nasal spray in the treatment of upper respiratory infections.

Yet another embodiment of the invention relates to a method for treating upper respiratory infections in any mammalian organism, such as a human or animal species, said method comprising the steps described herein thereby providing IgY antibodies specific for said one or more primary antigens and said one or more secondary antigens, and treating an upper respiratory infection in said mammalian organism by administering said IgY antibodies to an individual having contracted an upper respiratory infection, or being at risk of doing so unless treated prophylactically.

Yet another embodiment of the invention relates to a method for treating upper respiratory infections in any mammalian organism, including a human or animal species, according to claim 1, thereby providing IgY antibodies specific for said one or more primary antigens and said one or more secondary antigens, and treating an upper respiratory infection in said mammalian organism by administering said IgY antibodies to an individual having contracted an upper respiratory infection, or being at risk of doing so unless treated prophylactically.

In another embodiment said IgY antibodies are utilised to target toxic xenobiotics in a mammalian organism.

In another embodiment the method comprises the further step of utilising said one or more IgY antibodies as a component of a device used for detecting and/or sensing a compound or substance having affinity for said one or more IgY antibodies.

In another embodiment said antibodies are utilised as a component of a sensory device aimed at detecting or targeting polluting substances in the process of waste water purification.

In another embodiment said antibodies are utilised as a component of a sensory device aimed at detecting or targeting polluting substances in the process of gas purification.

In another embodiment said antibodies are utilised as a component of a sensory device aimed at detecting or targeting specific substances of interest in the process of water sampling, testing of chemicals and polluting agents in seawater and lakes, detection of explosives or drug testing In another embodiment said IgY antibodies are utilised to target toxic xenobiotics in a mammalian organism.

The invention claimed is:

1. A method for obtaining, from a plurality of different randomly generated IgY antibodies specific for one or more primary antigens, one or more isolated randomly generated IgY antibodies, but not all of said plurality of IgY antibodies, wherein said isolated IgY antibodies are also specific for one or more secondary antigens, said method comprising the steps of:
   i) generating a peptide library by random peptide synthesis, wherein the resulting peptides are randomized at each amino acid residue and at least the 20 naturally occurring amino acids are represented at each amino acid position of peptides in the library, wherein the length of the different peptides is in the range from 5 amino acid residues to 15 amino acid residues, wherein each peptide of the peptide library is a primary antigen,
   ii) generating a plurality of IgY antibodies by immunizing each of a plurality of avian organisms of the same or different species with a composition comprising peptides produced in step i), thereby generating a plurality of different randomly generated IgY antibodies,
   iii) providing one or more secondary antigens to be tested, wherein said one or more secondary antigens is immobilized to a support,
   iv) contacting said one or more secondary antigen(s) with the plurality of different IgY antibodies specific for one or more primary antigens as generated in step ii),
   v) washing to remove unspecifically bound antibodies, and recovering specifically bound antibodies,
   thereby obtaining one or more IgY antibodies having a specificity for both one or more of said primary antigens and one or more of said secondary antigens,
   wherein the primary and secondary antigens are not identical, and wherein the obtained IgY antibodies specific for said one or more secondary antigens have been raised against said one or more primary antigens only.

2. The method of claim 1 comprising the further step of extracting said different IgY antibodies from eggs laid by said plurality of avian organisms.

3. The method of claim 2 comprising the further step of purifying said different IgY antibodies.

4. The method of claim 1, wherein at least some of the secondary antigens comprise one or more peptide(s).

5. The method of claim 4, wherein said one or more secondary antigens and/or said primary antigen peptides comprise natural and/or non-natural amino acid residues.

6. The method of claim 5, wherein said one or more peptide(s) contain amino acid residues selected from the group consisting of natural amino acid residues and non-natural amino acid residues.

7. The method of claim 5, wherein said one or more peptide(s) contain natural amino acid residues.

8. The method of claim 5, wherein said one or more peptide(s) contain non-natural amino acid residues.

9. The method of claim 5, wherein said natural amino acids are selected from the group consisting of tyrosine, glycine, phenylalanine, methionine, alanine, serine, isoleucine, leucine, threonine, valine, praline, lysine, histidine, glutamine, glutamic acid, tryptophan, arginine, aspartic acid, asparagine, cysteine, selenocysteine and pyrrolysine.

10. The method of claim 5, wherein the natural and/or non-natural amino acids are modified.

11. The method of claim 10, wherein the modifications are selected from the group consisting of phosphorylation, sulfation, glycosylation, methylation, and acetylation.

12. The method of claim 4, wherein at least some of said secondary antigens comprise two or more peptides linked covalently or non-covalently by a chemical moiety.

13. The method of claim 12, wherein the chemical moiety is selected from moieties comprising a bond selected from the group consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

14. The method of claim 12, wherein the chemical moiety does not comprise or consist of an amino acid residue.

15. The method of claim 12, wherein the chemical moiety comprises or consists of a polymer to which different antigens are covalently attached.

16. The method of claim 15, wherein the polymer is in the form of a beaded or granulated resin.

17. The method of claim 16, wherein the resin is selected from the group consisting of styrenes, acrylates, unsaturated chlorides, esters, acetates, amides, alcohols, polystyrene, high density polystyrene latexes, brominated polystyrene, polymethylmethacrylate and other polyacrylic acids, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidenechloride, polydivinylbenzene, PEGA, SPOCC, POEPOP, HYDRA, PEG-polyacrylate copolymers, polyether-polyamine copolymers, cross-linked polyethylene diamines, and combinations thereof.

18. The method of claim 4, wherein at least some of said one or more peptide(s) are attached to a functional entity by one or more covalent or noncovalent linker residue(s) linking the one or more peptide(s) to the functional entity.

19. The method of claim 18, wherein the linker residue is selected from residues comprising a bond selected from the group consisting of peptide bonds, sulfonamide bonds, ester bonds, saccharide bonds, carbamate bonds, carbonate bonds, urea bonds, phosphonate bonds, urethane bonds, azatide bonds, peptoid bonds, ether bonds, ethoxy bonds, thioether bonds, single carbon bonds, double carbon bonds, triple carbon bonds, disulfide bonds, sulfide bonds, phosphodiester bonds, oxime bonds, imine bonds, imide bonds, including any combination thereof.

20. The method of claim 4, wherein bonds joining individual amino acid residues of the said one or more secondary antigen peptides and/or said primary antigen peptides are selected from the group consisting of peptide bonds, imine bonds and imide bonds.

21. The method of claim 4, wherein said one or more secondary antigen peptides and/or said primary antigen peptides each comprise one or more peptide domains selected from the group consisting of an α-peptide domain, a β-peptide domain, a γ-peptide domain, an w-peptide domain, a mono-, di- and tri-substituted α-peptide domain, a mono-, di- and tri-substituted β-peptide domain, a mono-, di- and tri-substituted γ-peptide domain, a mono-, di- and tri-substituted γ-peptide domain, a peptide domain wherein the amino acid residues are in the L-form, a peptide domain wherein the amino acid residues are in the D-form, a peptide domain wherein the amino acid residues are both in the L-form and in the D-form, a vinylogous peptide domain, a glyco-peptide domain, a vinylogous sulfonamide peptide domain, a polysulfonamide domain, a conjugated peptide domain and a conjugated peptide domain comprising one or more functional group(s), such as one or more prosthetic group(s).

22. The method of claim 4, wherein each said primary antigen peptide and each said secondary antigen peptide contains at least 5 amino acid residues, selected independently from each of the following groups i) to xiii) consisting of
i) Amino acids having polar side chains (Asp, Glu, Lys, Arg, His, Asn, Gin, Ser, Thr, Tyr, and Cys,)
ii) Amino acids having non-polar side chains (Giy, Ala, Val, Leu, Ile, Phe, Trp, Pro, and Met)
iii) Amino acids having aliphatic side chains (Giy, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
(viii) Amino acids having amide side chains (Asn, Gin)
(ix) Amino acids having hydroxy side chains (Ser, Thr)
(x) Amino acids having sulphur-containing side chains (Cys, Met),
(xi) Neutral, weakly hydrophobic amino acids (Pro, Ala, Gly, Ser, Thr)
(xii) Hydrophilic, acidic amino acids (Gin, Asn, Glu, Asp), and
(xiii) Hydrophobic amino acids (Leu, Ile, Val).

23. The method of claim 4 wherein any pair of amino acid residues, of respectively primary and secondary antigens differ in Kyte & Doolittle hydropathy index within +/−2.5 units of one another.

24. The method of claim 1, wherein substantially all of the secondary antigens comprise one or more peptide(s).

25. The method of claim 1, wherein at least some of the secondary antigens consist of one or more peptide(s).

26. The method of claim 1, wherein substantially all of the secondary antigens consist of one or more peptide(s).

27. The method of claim 1, wherein the avian organisms are of the same species.

28. The method of claim 1, wherein the avian organisms are of different species.

29. The method of claim 1, wherein the avian species is a female.

30. The method of claim 29, wherein the female avian species is a hen.

31. The method of claim 1, wherein the avian organism is a bird of the gallinacean type.

32. The method of claim 31, wherein the avian organism is *Gallus gallus* domestica.

33. The method of claim 1, wherein a total of from 1000 to 100000 avian organisms are immunized.

34. The method of claim 33, wherein the number of avian organisms immunized is in the range of from 1000 to 38000.

35. The method of claim 4, wherein different IgY antibodies are generated in substantially each different avian organism.

36. The method of claim 4 comprising the further step of subsequently immunizing the avian organism directly with a plurality of peptides, which can be identical or different from the peptides used for the initial immunization.

37. The method of claim 36, wherein at least some of the peptides used for the initial immunization and the subsequent immunization are identical.

38. The method of claim 37 wherein at least one amino acid residue of said primary antigen peptides is of the formula

wherein N, $C_\alpha$ and C are connected to form the backbone of a peptide bond and R1 is selected from the group consisting of:
hydrido,
substituted and unsubstituted alkyl, substituted and unsubstituted haloalkyl, substituted and unsubstituted hydroxyalkyl, substituted and unsubstituted alkylsulfonyl,
substituted and unsubstituted alkenyl,
halo,
substituted and unsubstituted alkoxy,
substituted and unsubstituted alkoxyalkyl,
substituted and unsubstituted haloalkoxy,
substituted and unsubstituted haloalkoxyalkyl,
substituted and unsubstituted aryl,
substituted and unsubstituted heterocyclic,
substituted and unsubstituted heteroaryl, sulfonyl, substituted and unsubstituted alkylsulfonyl, substituted and unsubstituted arylsulfonyl, sulfamyl, sulfonamidyl, aminosulfonyl, substituted and unsubstituted N-alkylaminosulfonyl, substituted and unsubstituted N-arylaminosulfonyl, substituted and unsubstituted N,N-dialkylaminosulfonyl, substituted and unsubstituted N-alkyl-N-arylaminosulfonyl, substituted and unsubstituted N-alkylaminosulfonyl, substituted and unsubstituted N,N-dialkylaminosulfonyl, substituted and unsubstituted N-arylaminosulfonyl, substituted and unsubstituted N-alkyl-Narylaminosulfonyl, carboxy, substituted and unsubstituted carboxyalkyl, carbonyl, substituted and unsubstituted alkylcarbonyl, substituted and unsubstituted alkylcarbonylalkyl, substituted and unsubstituted alkoxycarbonyl, substituted and unsubstituted alkoxycarbonylalkyl, aminocarbonyl, substituted and unsubstituted aminocarbonylalkyl, substituted and unsubstituted N-alkylaminocarbonyl, substituted and unsubstituted N-arylaminocarbonyl, substituted and unsubstituted N,N-dialkylaminocarbonyl, substituted and unsubstituted N-alkyl-N-arylaminocarbonyl, substituted and unsubstituted N-alkyl-N-hydroxyaminocarbonyl, substituted and unsubstituted N-alkyl-N-hydroxyaminocarbonylalkyl, substituted and unsubstituted N-alkylaminocarbonyl, substituted and unsubstituted N,N-dialkylaminocarbonyl, substituted and unsubstituted N-arylaminocarbonyl, substituted and unsubstituted N-alkyl-N-arylaminocarbonyl, substituted and unsubstituted aminocarbonylalkyl, substituted and unsubstituted N-cycloalkylaminocarbonyl, substituted and unsubstituted aminoalkyl, substituted and unsubstituted alkylaminoalkyl, amidino, cyanoamidino, substituted and unsubstituted heterocyclicalkyl, substituted and unsubstituted aralkyl, substituted and unsubstituted cycloalkyl, substituted and unsubstituted cycloalkenyl, substituted and unsubstituted alkylthio, substituted and unsubstituted alkylsulfinyl, substituted and unsubstituted N-alkylamino, substituted and unsubstituted N,N-dialkylamino, substituted and unsubstituted arylamino, substituted and unsubstituted aralkylamino, substituted and unsubstituted N-alkyl-N-arylamino, substituted and unsubstituted N-aralkyl-N-alkylamino, substituted and unsubstituted N-arylaminoalkyl, substituted and unsubstituted N-aralkylaminoalkyl, substituted and unsubstituted N-alkyl-N-arylaminoalkyl, substituted and unsubstituted N-aralkyl-N-alkyl amino alkyl, acyl, acylamino, substituted and unsubstituted arylthio, substituted and unsubstituted aralkylthio, substituted and unsubstituted aryloxy, substituted and unsubstituted aralkoxy, substituted and unsubstituted haloaralkyl, substituted and unsubstituted carboxyhaloalkyl, substituted and unsubstituted alkoxycarbonylhaloalkyl, substituted and unsubstituted aminocarbonylhaloalkyl, substituted and unsubstituted alkylaminocarbonylhaloalkyl, substituted and unsubstituted alkoxycarbonylcyanoalkenyl, substituted and unsubstituted carboxyalkylaminocarbonyl, substituted and unsubstituted aralkoxycarbonylalkylaminocarbonyl, substituted and unsubstituted cycloalkylalkyl, and substituted and unsubstituted aralkenyl.

39. The method of claim 1, wherein at least some of said primary and/or secondary antigens comprise one or more entities selected from the group consisting of —NHN(R)CO—; —NHB(R)CO—; —NHC(RR')CO—; —NHC(=CHR)CO—; —NHC$_6$H$_4$CO—; —NHCH$_2$CHRCO—; —NHCHRCH$_2$CO—; —COCH$_2$—; —COS—; —CONR—; —COO—; —CSNH—; —CH$_2$NH—; —CH$_2$CH$_2$—; —CH$_2$S—; —CH$_2$SO—; —CH$_2$SO$_2$—; —CH(CH$_3$)S—; —CH=CH—; —NHCO—; NHCONH—; —CONHO—; —C(=CH$_2$)CH$_2$—; —PO$_2$—NH—; —PO$_2$—CH$_2$—; —PO$_2$—CH$_2$W—; —SO$_2$NH—, wherein R is H or an optionally substituted alkyl.

40. The method of claim 1, wherein the avian organisms are immunized by oral administration or injection of the composition comprising the different primary antigens.

41. The method of claim 1, wherein the method for immunizing the avian organisms comprises the initial and optional subsequent step(s) of injecting the different antigens directly into said avian organisms.

42. The method of claim 41, wherein the injection is an intramuscular injection and/or a subcutaneous injection.

43. The method of claim 41, wherein the injection is an intramuscular injection.

44. The method of claim 1, wherein said immunizing comprises administering said primary antigens to said avian organisms in the presence of one or more carriers covalently or non-covalently attached to at least some of said primary antigens.

45. The method of claim 44, wherein said immunizing comprises administering said primary antigens to said avian organisms in the presence of one or more adjuvants covalently or non-covalently attached to at least some of said antigens and in the presence of said one or more carriers.

46. The method of claim 45, wherein the adjuvant is selected from the group consisting of mineral salts, oil emulsions and surfactant based formulations AS04 (Al salt with MPL), ISCOMS (structured complex of saponins and lipids), polyactide co-glycolide (PIG), monophosphoryl lipid A (MPL), Detox (MPL+*M. Phlei* cell wall skeleton), AGP (RC-529 (synthetic acylated monosaccharide)), DC-chol (lipoidal immunostimulators able to self organize into liposomes), OM-174 (lipid A derivative), CpG motifs (synthetic oligonucleotides containing immunostimulatory CpG motifs), modified bacterial toxin with non-toxic adjuvant effects, Endogenous human immunomodulators, gold particles and other inert vehicles.

47. The method of claim 46, wherein the adjuvant is aluminium hydroxide, aluminium phosphate gel, or calcium phosphate gel.

48. The method of claim 46, wherein the adjuvant is MF59 (microfluidised detergent stabilized oil in water emulsion), QS21 (purified saponin), AS02 (SBAS2, oil-in-water emulsion+monophosphoryllipid A (MPL)+QS21), montanide ISA 51 or ISA-720 (stabilized water in oil emulsion), or Adjuvant 65 (containing peanut oil, mannide monooleate and aluminium monostearate).

49. The method of claim 46, wherein the adjuvant is virosomes (unilamellar liposomal vehicles incorporating influenza haemagglutinin).

50. The method of claim 46, wherein the adjuvant is hGM-CSF, hII-12, or immudaptin (C3d tandem array).

51. The method of claim 44, wherein said one or more carriers and said at least some of said primary antigens are both non-conjugated.

52. The method of claim 44 wherein said one or more are conjugated and said at least some of said primary antigens are non-conjugated.

53. The method of claim 44, wherein said one or more carriers are conjugated and said primary antigens are all non-conjugated.

54. The method of claim 44 wherein said one or more carriers are non-conjugated and said at least some of said primary antigens are conjugated.

55. The method of claim 44 wherein said one or more carrier(s) is non-conjugated and said primary antigens are all conjugated.

56. The method of claim 44 wherein said one or more carrier(s) and all of said primary antigens are conjugated.

57. The method of claim 44, wherein said one or more carriers and at least some of said primary antigens are both non-conjugated.

58. The method of claim 44, wherein said one or more carrier(s) and all of said primary antigens are both non-conjugated.

59. The method of claim 44, wherein said one or more carrier(s) is conjugated to at least some of said primary antigens.

60. The method of claim 44 herein said carrier is a scaffold capable of presenting said primary antigens to an HLA complex in said avian.

61. The method of claim 44 wherein the carrier is selected from the group consisting of phosphate, citrate, and other organic acids; antioxidants including ascorbic acid; low molecular weight (less than about 10 amino acid residues) polypeptides; proteins, serum albumin, gelatin, or immunoglobulins; hydrophilic polymers, polyvinylpyrrolidone; amino acids, glycine, glutamine, asparagine, arginine or lysine; monosaccharides, disaccharides, carbohydrates including glucose, mannose, dextrins; chelating agents EDTA; sugar alcohols, mannitol or sorbitol; salt-forming counterions, sodium; nonionic surfactants, and polyethylene glycol (PEG).

62. The method of claim 1 comprising the further step of targeting one or more of the obtained IgY antibodies having a specificity for both one or more of said primary antigens and one or more of said secondary antigens to a ligand having an affinity for one or more of said IgY antibodies.

63. The method of claim 62, wherein the ligand is selected from the group consisting of a protein, a peptide, a carbohydrate, a polysaccharide, a glycoprotein, a hormone, a receptor, an antigen, an antibody, a virus, a substrate, a metabolite, a transition state analogue, a co-factor, an inhibitor, a drug, a dye, a nutrient, a growth factor, a cell, a tissue, angiotensin converting enzyme, renin, cyclooxygenase, 5-lipoxygenase, IL-10 converting enzyme, cytokine receptors, PDGF receptor, type II inosine mono phosphate dehydrogenase, 13-lactamases, fungal cytochrome P-450, bradykinin, neutrophil elastase, HIV proteins, such as tat, rev, gag, int, RT, nucleocapsid, VEGF, bFGF, TGFI3, KGF, PDGF, thrombin, theophylline, caffeine, substance P, IgE, sPLA2, red blood cells, glioblastomas, fibrin clots, PBMCs, hCG, lectins, selectins, cytokines, ICP4 and complement proteins.

64. The method of claim 1 wherein said generated IgY antibodies are obtained using said secondary antigen, which comprises one or more peptides.

65. The method of claim 64 wherein the length of the one or more secondary antigen peptides in the range of 5 amino acid residues to less than 50 amino acid residues.

66. The method of claim 64 wherein the primary and secondary antigen differ in sequence identity as defined by any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85 and BLOSUM 90, all using default parameters.

67. The method of claim 64 wherein the primary and secondary antigens differ in secondary structure elements selected from the group consisting of alpha-helices, $3_{10}$-helices, π-helices, beta-strands, beta-sheets, and beta-hairpins loops; and/or differ in N-terminal and/or C-terminal stretches of amino acids, and/or loops connecting said secondary structure elements.

68. The method of claim 67 wherein at least one secondary structure element of a secondary antigen differs in size by at least 1.5 Å from the corresponding secondary structure element of the primary antigen.

69. The method of claim 64 wherein the primary and secondary antigens differ in tertiary structure.

70. The method of claim 64 wherein the primary and secondary antigens differ in quaternary structure.

71. The method of claim 64 wherein the primary and secondary antigens differ in posttranslational modification.

72. The method of claim 64 wherein any peptide or peptide-like compound comprises 0, 1, 2, 3, 4, 5, 6, 7, 8, 9, 10, 11, 15, 20 or more modifications.

73. The method of claim 64 wherein the primary and secondary antigens differ by only one of them being modified by ISGylation (the covalent linkage to ISG15 protein (Interferon-Stimulated Gene 15)), SUMOylation (the covalent linkage to SUMO (Small Ubiquitin related Modifier) protein), and/or ubiquitination (the covalent linkage to ubiquitin protein).

74. The method of claim 64 wherein the primary and secondary antigens differ by only one of the two being modified by a change of the chemical nature of amino acids, wherein the change comprises citrullination or deimination (the conversion of arginine to citrulline), and/or deamidation (the conversion of glutamine to glutamic acid or asparagine to aspartic acid).

75. The method of claim 64 wherein the primary and secondary antigens differ by only one of them comprising a disulfide bridge (the covalent linkage of two cysteine amino acids) and/or a proteolytic cleavage (cleavage of a protein at a peptide bond) site.

76. The method of claim 64 wherein the primary and secondary antigens differ in at least one structural element from the group consisting of: an α-peptide domain, a β-peptide domain, a γ-peptide domain, an ω-peptide domain, a mono-, di-, or tri-substituted α-peptide domain, a mono-, di-, or tri-substituted β-peptide domain, a mono-, di, or tri-substituted γ-peptide domain, a mono-, di-, or tri-substituted ω-peptide domain, a peptide domain wherein the amino acid residues are in L-form, a peptide domain wherein the amino acid residues are in D-form, a peptide domain wherein the amino acid residues are both in L-form and in D-form, a vinylogous peptide domain, a glyco-peptide domain, a vinylogous sulfonamide peptide domain, a polysulfonamide domain, a conjugated peptide domain, and a conjugated peptide domain comprising one or more functional group(s) or one or more prosthetic group(s).

77. The method of claim 64 wherein said primary and secondary antigen peptides differ in the number of linked peptides, wherein the linked peptides form di-, tri-, tetra-, penta-, hexa-, hepta-, octa-, nona- or deca-polypeptides or larger peptide polymers.

78. The method of claim 64 wherein the primary antigens are linked to a carrier selected from the group consisting of slowly metabolized macromolecules, polysaccharides, polylactic acids, polyglycolic acids, polymeric amino acids, amino acid copolymers, lipid aggregates (including oil droplets and liposomes), inactive virus particles and proteins including the keyhole limpet hemocyanin (KLH) and bovine serum albumin (BSA), ovalbumin (OVA), rabbit serum albumin (RSA) and chicken serum albumin (CSA).

79. The method of claim 64 where said primary and secondary antigens differ in conjugation pattern.

80. The method of claim 79 where said conjugation comprises an oxidatively induced cross-link or is catalyzed by a chemical cross-linking reagent selected from the group consisting of glutaraldehyde, carbodiimide and formaldehyde.

81. The method of claim 64 performed one or more times.

82. An assay for testing the specificity of a plurality of different IgY antibodies by using a primary antigen as a secondary antigen, comprising the steps of:
 i) immunizing an avian organism with a plurality of primary antigens;
 ii) generating an antibody library according to steps i)-ii) of claim 1;
 iii) harvesting from said antibody library IgY antibodies directed against the primary antigens used for immunization by using a secondary antigen; and
 iv) analyzing the affinity of the harvested antigen:antibody complex.

83. The method of claim 1 wherein one or more of the antibodies generated in step ii) is utilized for targeting a specific epitope of a secondary antigen.

84. The method of claim 83 wherein said targeted epitope is a part of a pathological entity or process of a mammalian organism.

85. A method for treating a disease in a mammalian organism, said method comprising:
 performing the steps of claim 1, thereby providing IgY antibodies specific for said one or more primary antigens and said one or more secondary antigens, and
 treating said disease by administering said IgY antibodies to an individual having contracted said disease, or at risk of doing so unless treated prophylactically.

86. The method of treating a disease according to claim 85, wherein said one or more secondary antigens used for the isolation of said one or more IgY antibodies is a marker for the disease.

87. The method of claim 85, wherein said treating comprises treating *Streptococcus mutans* serotype c infection in said mammalian organism.

88. The method of claim 85, wherein said mammalian organism is diagnosed as having cystic fibrosis, or has a prognosis for developing cystic fibrosis.

89. A method for treating an upper respiratory infection in a subject comprising
 producing one or more IgY antibodies by performing steps i)-v) of claim 1;
 preparing a nasal spray composition comprising said one or more IgY antibodies; and
 administering to the subject said nasal spray composition, thereby treating the upper respiratory infection.

90. The method of claim 85, wherein the disease is an upper respiratory infection.

91. The method of claim 85 wherein the disease is selected from the group of: diarrhea, dysentery, cholera, and transmissible gastroenteritis.

92. The method of claim 85, wherein the mammalian organism is selected from a human, a pig and a cow.

93. A method for treating or controlling plaque in a subject by
 producing one or more IgY antibodies by performing steps i)-v) of claim 1;
 preparing a mouth rinse or a tooth hygiene composition comprising said one or more IgY antibodies; and
 administering to the subject said mouth rinse or tooth hygiene composition, thereby treating or controlling the plaque or the disease.

94. A method of targeting a toxic xenobiotic in a mammalian organism by
 producing one or more IgY antibodies by performing steps i)-v) of claim 1;
 administering to the mammalian organism said one or more IgY antibodies wherein the IgY antibodies have the ability to specifically bind to the toxic xenobiotic, thereby targeting the toxic xenobiotic in the mammalian organism.

95. A method of detecting a compound comprising
 producing one or more IgY antibodies having an affinity for the compound by performing steps i)-v) of claim 1;
 incorporating said one or more IgY antibodies into a device; and
 using said device to detect the compound.

96. The method of claim 95 that is carried out in a process of water sampling, testing of chemicals or polluting agents in seawater or lakes, or detection of explosives or drug testing.

* * * * *

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Control sequence

<400> SEQUENCE: 1

Cys Arg Glu Gly Pro Thr Lys Gly Met His Thr Ala Val Gln Gly Leu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Control sequence

<400> SEQUENCE: 2

Met Ala Pro Gly Ser Thr Val Gly Thr Leu Val Ala Asn Met Thr Cys
1               5                   10                  15

<210> SEQ ID NO 3
```

```
<211> LENGTH: 20
<212> TYPE: PRT
<213> ORGANISM: Artificial Sequence
<220> FEATURE:
<223> OTHER INFORMATION: Control sequence

<400> SEQUENCE: 3

Cys Asp Lys Ile Asp Ser Tyr Ala Gln Gln Asp Leu Lys Lys Gly Leu
1               5                   10                  15

His Leu Tyr Gly
            20

<210> SEQ ID NO 4
<211> LENGTH: 16
<212> TYPE: PRT
<213> ORGANISM: Artificial Sequence
<220> FEATURE:
<223> OTHER INFORMATION: Control sequence

<400> SEQUENCE: 4

Cys Phe Phe Ala Tyr Ser Asp Lys Ile Asp Ser Tyr Ala Gln Gln Asp
1               5                   10                  15
```